US009669224B2

(12) United States Patent
Carney et al.

(10) Patent No.: US 9,669,224 B2
(45) Date of Patent: Jun. 6, 2017

(54) TRIGGERED PACING SYSTEM

(71) Applicant: Medtronic, Inc., Minneapolis, MN (US)

(72) Inventors: James K Carney, Roseville, MN (US); Can Cinbis, Salt Lake City, UT (US); Jonathan L Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/695,004

(22) Filed: Apr. 23, 2015

(65) Prior Publication Data
US 2015/0321011 A1  Nov. 12, 2015

Related U.S. Application Data

(60) Provisional application No. 61/989,302, filed on May 6, 2014.

(51) Int. Cl.
| A61N 1/00 | (2006.01) |
|---|---|
| A61N 1/365 | (2006.01) |
| A61N 1/362 | (2006.01) |
| A61N 1/39 | (2006.01) |
| A61N 1/372 | (2006.01) |

(52) U.S. Cl.
CPC ......... *A61N 1/36514* (2013.01); *A61N 1/362* (2013.01); *A61N 1/3727* (2013.01); *A61N 1/37252* (2013.01); *A61N 1/37276* (2013.01); *A61N 1/37288* (2013.01); *A61N 1/3987* (2013.01)

(58) Field of Classification Search
CPC .... A61N 1/3605; A61N 1/362; A61N 1/3622; A61N 1/3684; A61N 1/3712; A61N 1/3708; A61N 1/37211; A61N 1/37288; A61N 1/3727; A61N 1/37252; A61N 1/37276
See application file for complete search history.

(56) References Cited

U.S. PATENT DOCUMENTS

| 4,280,502 A | 7/1981 | Baker, Jr. et al. |
| 4,343,311 A | 8/1982 | Markowitz |

(Continued)

FOREIGN PATENT DOCUMENTS

| EP | 1541191 | 6/2005 |
| EP | 2471452 A1 | 7/2012 |

(Continued)

OTHER PUBLICATIONS (PCT/US2015/029458) PCT Notification of Transmittal of the International Search Report and the Written Opinion of the International Searching Authority, mailed Aug. 25, 2015, 8 pages.

(Continued)

*Primary Examiner* — Scott Getzow

(57) ABSTRACT

A medical device system is configured to sense physiological events by a first device and control a transducer to emit trigger signals in response to the sensed physiological events. A second device detects the trigger signals and delivers therapeutic stimulation pulses in response to the trigger signals. The therapeutic stimulation pulses have a combined total time duration over the sensed physiological events that is greater than the combined total time duration of the trigger signals.

14 Claims, 21 Drawing Sheets

(56) References Cited

U.S. PATENT DOCUMENTS

| | | |
|---|---|---|
| 4,374,382 A | 2/1983 | Markowitz |
| 4,481,950 A | 11/1984 | Duggan |
| 4,543,955 A | 10/1985 | Schroeppel |
| 4,787,389 A | 11/1988 | Tarjan |
| 4,830,006 A | 5/1989 | Haluska et al. |
| 4,865,037 A | 9/1989 | Chin et al. |
| 5,113,859 A | 5/1992 | Funke |
| 5,117,824 A | 6/1992 | Keimel et al. |
| 5,139,020 A | 8/1992 | Koestner et al. |
| 5,144,950 A | 9/1992 | Stoop et al. |
| 5,174,289 A | 12/1992 | Cohen |
| 5,193,539 A | 3/1993 | Schulman et al. |
| 5,255,692 A | 10/1993 | Neubauer et al. |
| 5,312,445 A | 5/1994 | Nappholz |
| 5,331,966 A | 7/1994 | Bennett et al. |
| 5,354,316 A | 10/1994 | Keimel |
| 5,402,070 A | 3/1995 | Shelton et al. |
| 5,411,535 A | 5/1995 | Fujii et al. |
| 5,545,186 A | 8/1996 | Olson et al. |
| 5,620,474 A | 4/1997 | Koopman |
| 5,683,426 A | 11/1997 | Greenhut et al. |
| 5,749,909 A | 5/1998 | Schroeppel et al. |
| 5,814,089 A | 9/1998 | Stokes et al. |
| 5,817,130 A | 10/1998 | Cox et al. |
| 5,855,593 A | 1/1999 | Olson et al. |
| 5,893,882 A | 4/1999 | Peterson et al. |
| 5,902,326 A | 5/1999 | Lessar et al. |
| 5,928,271 A | 7/1999 | Hess et al. |
| 5,954,649 A | 9/1999 | Chia et al. |
| 6,016,448 A | 1/2000 | Busacker et al. |
| 6,108,579 A | 8/2000 | Snell et al. |
| 6,206,847 B1 | 3/2001 | Edwards et al. |
| 6,208,894 B1 | 3/2001 | Schulman et al. |
| 6,256,534 B1 | 7/2001 | Dahl |
| 6,298,261 B1 | 10/2001 | Rex |
| 6,393,316 B1 | 5/2002 | Gillberg et al. |
| 6,442,426 B1 | 8/2002 | Kroll |
| 6,477,420 B1 | 11/2002 | Struble et al. |
| 6,505,067 B1 | 1/2003 | Lee |
| 6,508,771 B1 | 1/2003 | Padmanabhan et al. |
| 6,522,915 B1 | 2/2003 | Ceballos et al. |
| 6,526,311 B2 | 2/2003 | Begemann |
| 6,592,519 B1 | 7/2003 | Martinez |
| 6,622,046 B2 | 9/2003 | Fraley et al. |
| 6,628,989 B1 | 9/2003 | Penner et al. |
| 6,631,290 B1 | 10/2003 | Guck et al. |
| 6,738,668 B1 | 5/2004 | Mouchawar et al. |
| 6,754,528 B2 | 6/2004 | Bardy et al. |
| 6,760,615 B2 | 7/2004 | Ferek-Petric |
| 6,764,446 B2 | 7/2004 | Wolinsky et al. |
| 6,788,971 B1 | 9/2004 | Sloman et al. |
| 6,810,283 B2 | 10/2004 | Suribhotla |
| 6,904,315 B2 | 6/2005 | Panken et al. |
| 6,934,585 B1 | 8/2005 | Schloss et al. |
| 7,024,248 B2 | 4/2006 | Penner et al. |
| 7,027,858 B2 | 4/2006 | Cao |
| 7,160,258 B2 | 1/2007 | Imran et al. |
| 7,181,284 B2 | 2/2007 | Burnes et al. |
| 7,198,603 B2 | 4/2007 | Penner et al. |
| 7,272,448 B1 | 9/2007 | Morgan et al. |
| 7,283,874 B2 | 10/2007 | Penner |
| 7,392,085 B2 | 6/2008 | Warren et al. |
| 7,532,929 B2 | 5/2009 | Mussig et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,630,767 B1 | 12/2009 | Poore et al. |
| 7,634,313 B1 | 12/2009 | Kroll et al. |
| 7,706,879 B2 | 4/2010 | Burnes et al. |
| 7,742,812 B2 | 6/2010 | Ghanem |
| 7,848,815 B2 | 12/2010 | Brisken et al. |
| 7,881,791 B2 | 2/2011 | Sambelashvili et al. |
| 7,890,173 B2 | 2/2011 | Brisken et al. |
| 7,904,153 B2 | 3/2011 | Greenhut et al. |
| 7,930,027 B2 | 4/2011 | Prakash et al. |
| 7,930,031 B2 | 4/2011 | Penner |
| 7,937,148 B2 | 5/2011 | Jacobson |
| 7,941,218 B2 | 5/2011 | Sambelashvili et al. |
| 7,945,064 B2 | 5/2011 | O'Brien, Jr. et al. |
| 7,953,493 B2 | 5/2011 | Fowler et al. |
| 7,991,467 B2 | 8/2011 | Markowitz et al. |
| 7,996,087 B2 | 8/2011 | Cowan et al. |
| 8,002,718 B2 | 8/2011 | Buchholtz et al. |
| 8,032,219 B2 | 10/2011 | Neumann et al. |
| 8,095,207 B2 | 1/2012 | Belalcazar |
| 8,145,308 B2 | 3/2012 | Sambelashvili et al. |
| 8,160,684 B2 | 4/2012 | Ghanem et al. |
| 8,160,686 B2 | 4/2012 | Allavatam et al. |
| 8,204,590 B2 | 6/2012 | Sambelashvili et al. |
| 8,214,041 B2 | 7/2012 | Van Gelder et al. |
| 8,275,432 B2 | 9/2012 | Kuhn et al. |
| 8,315,701 B2 | 11/2012 | Cowan et al. |
| 8,352,025 B2 | 1/2013 | Jacobson |
| 8,364,276 B2 | 1/2013 | Willis |
| 8,391,964 B2 | 3/2013 | Musley et al. |
| 8,428,716 B2 | 4/2013 | Mullen et al. |
| 8,433,409 B2 | 4/2013 | Johnson et al. |
| 8,452,402 B2 | 5/2013 | Ecker et al. |
| 8,457,742 B2 | 6/2013 | Jacobson |
| 8,521,268 B2 | 8/2013 | Zhang et al. |
| 8,532,785 B1 | 9/2013 | Crutchfield et al. |
| 8,538,524 B2 | 9/2013 | Rosenberg |
| 8,540,631 B2 | 9/2013 | Penner et al. |
| 8,541,131 B2 | 9/2013 | Lund et al. |
| 8,617,082 B2 | 12/2013 | Zhang et al. |
| 8,639,333 B2 | 1/2014 | Stadler et al. |
| 8,652,048 B2 | 2/2014 | Skerl et al. |
| 8,666,505 B2 | 3/2014 | O'Brien et al. |
| 8,718,773 B2 | 5/2014 | Willis et al. |
| 8,718,793 B2 | 5/2014 | O'Connor |
| 8,744,572 B1 | 6/2014 | Greenhut et al. |
| 8,768,459 B2 | 7/2014 | Ghosh et al. |
| 8,886,307 B2 | 11/2014 | Sambelashvili et al. |
| 8,886,311 B2 | 11/2014 | Anderson et al. |
| 8,923,963 B2 | 12/2014 | Bonner et al. |
| 9,008,776 B2 | 4/2015 | Cowan et al. |
| 9,168,380 B1 | 10/2015 | Greenhut et al. |
| 2004/0204744 A1 | 10/2004 | Penner et al. |
| 2004/0215308 A1 | 10/2004 | Bardy et al. |
| 2005/0010120 A1 | 1/2005 | Jung |
| 2005/0043761 A1 | 2/2005 | Connelly et al. |
| 2005/0277990 A1 | 12/2005 | Ostroff et al. |
| 2006/0009818 A1 | 1/2006 | Von Arx et al. |
| 2006/0085041 A1 | 4/2006 | Hastings et al. |
| 2006/0116593 A1 | 6/2006 | Zhang |
| 2006/0161205 A1 | 7/2006 | Mitrani et al. |
| 2006/0235478 A1 | 10/2006 | Van Gelder et al. |
| 2006/0241705 A1 | 10/2006 | Neumann et al. |
| 2007/0049975 A1 | 3/2007 | Cates et al. |
| 2007/0088394 A1 | 4/2007 | Jacobson |
| 2007/0088398 A1 | 4/2007 | Jacobson |
| 2007/0293900 A1 | 12/2007 | Sheldon et al. |
| 2007/0299475 A1 | 12/2007 | Levin et al. |
| 2008/0119911 A1 | 5/2008 | Rosero |
| 2008/0154322 A1 | 6/2008 | Jackson et al. |
| 2008/0269816 A1 | 10/2008 | Prakash et al. |
| 2008/0269823 A1 | 10/2008 | Burnes et al. |
| 2008/0288039 A1 | 11/2008 | Reddy |
| 2009/0036940 A1 | 2/2009 | Wei et al. |
| 2009/0036941 A1 | 2/2009 | Corbucci |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0042108 A1 | 2/2010 | Hibino |
| 2010/0106210 A1 | 4/2010 | Hedberg et al. |
| 2010/0152798 A1 | 6/2010 | Sanghera et al. |
| 2010/0198291 A1 | 8/2010 | Sambelashvili et al. |
| 2010/0228308 A1 | 9/2010 | Cowan et al. |

(56) References Cited

U.S. PATENT DOCUMENTS

| | | |
|---|---|---|
| 2010/0286541 A1 | 11/2010 | Musley et al. |
| 2011/0071586 A1 | 3/2011 | Jacobson |
| 2011/0125078 A1 | 5/2011 | Denison et al. |
| 2011/0184492 A1 | 7/2011 | Martens et al. |
| 2011/0190841 A1 | 8/2011 | Sambelashvili et al. |
| 2011/0196444 A1 | 8/2011 | Prakash et al. |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0172892 A1 | 7/2012 | Grubac et al. |
| 2012/0263218 A1 | 10/2012 | Dal Molin et al. |
| 2012/0296228 A1 | 11/2012 | Zhang et al. |
| 2012/0303084 A1 | 11/2012 | Kleckner |
| 2012/0316613 A1 | 12/2012 | Keefe et al. |
| 2013/0013017 A1 | 1/2013 | Mullen et al. |
| 2013/0066169 A1 | 3/2013 | Rys et al. |
| 2013/0103109 A1 | 4/2013 | Jacobson |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0138006 A1 | 5/2013 | Bornzin |
| 2013/0197599 A1 | 8/2013 | Sambelashvili et al. |
| 2013/0226259 A1 | 8/2013 | Penner |
| 2013/0231710 A1 | 9/2013 | Jacobson |
| 2013/0268017 A1 | 10/2013 | Zhang et al. |
| 2013/0274828 A1 | 10/2013 | Willis |
| 2013/0282073 A1 | 10/2013 | Cowan et al. |
| 2014/0114372 A1 | 4/2014 | Ghosh et al. |
| 2014/0257421 A1 | 9/2014 | Sanghera et al. |
| 2014/0330208 A1 | 11/2014 | Christie et al. |
| 2014/0330326 A1 | 11/2014 | Thompson-Naumann et al. |
| 2014/0358135 A1 | 12/2014 | Sambelashvili et al. |
| 2015/0142070 A1 | 5/2015 | Sambelashvili |
| 2016/0113536 A1 | 4/2016 | Greenhut et al. |

FOREIGN PATENT DOCUMENTS

| | | |
|---|---|---|
| WO | 95/02995 | 2/1995 |
| WO | WO 03003905 A2 | 1/2003 |

OTHER PUBLICATIONS (PCT/US2014/066792) PCT Notification of Transmittal of the International Search Report and the Written Opinion of the International Searching Authority.

(PCT/US2013/013601) PCT Notification of Transmittal of the International Search Report and the Written Opinion of the International Searching Authority.

Rodney Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

U.S. Appl. No. 14/801,049, filed Jul. 16, 2015.

(PCT/US2015/029464) PCT Notification of Transmittal of the International Search Report and the Written Opinion of the International Searching Authority, Mailed Jul. 13, 2015, 9 pages.

Greenhut, et al., Method and Apparatus for Selection and Use of Virtual Sensing Vectors, U.S. Appl. No. 14/524,090, filed Oct. 27, 2014, 57pp.

U.S. Appl. No. 13/665,601 to Bonner et al., entitled, "Leadless Pacemaker System," and filed on Oct. 31, 2012.

U.S. Appl. No. 14/261,460, filed Apr. 25, 2014, entitled "Implantable Medical Device System Having Implantable Cardiac Defibrillator System and Substernal Leadless Pacing Device".

U.S. Appl. No. 14/257,462, filed Apr. 21, 2014 entitled "Anchoring an Implantable Medical Device Within a Substernal Space".

(PCT/US2014/036782) PCT Notification of Transmittal of the International Search Report and the Written Opinion of the International Searching Authority, Mailed Aug. 22, 2014, 12 pages.

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failure in S-ICD patients," Clinical Research Cardiology, Published On-line Oct. 2, 2014, 3 pages.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.

(PCT/US2015/029495) PCT Notification of Transmittal of the International Search Report and the Written Opinion of the International Searching Authority, mailed Aug. 12, 2015, 9 pages.

TRIGGERED PACING SYSTEM

REFERENCE TO RELATED APPLICATIONS

This application claims priority to U.S. Pat. Application No. 61/989,302 filed provisionally on May 6, 2014 and incorporated herein by reference in its entirety. This application also cross-references U.S. Pat. Application No. 61/989,114 and U.S. Pat. Application No. 61/989,123, filed provisionally on May 6, 2014; and U.S. patent application Ser. No. 14/694,990 and U.S. patent application Ser. No. 14/695,013, filed on even date herewith, all of which are incorporated herein by reference in their entirety.

TECHNICAL FIELD

The disclosure relates to an implantable medical device system and associated method for delivering therapeutic stimulation pulses using a triggered therapy delivery device.

BACKGROUND

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, leadless intracardiac pacemakers have been introduced which can be implanted directly in a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of a leadless, intracardiac pacemaker.

New challenges arise, however, in controlling an intracardiac pacemaker to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in whom one or more heart chambers are electrically paced to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g., an atrio-ventricular (AV) interval and/or an inter-ventricular (VV) interval. The AV interval controls the timing of ventricular pacing pulses relative to a preceding atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

SUMMARY

In general, the disclosure is directed to an implantable medical device (IMD) system including a therapy delivery device and a sensing device and an associated method for triggering the therapy delivery device to deliver therapy. The sensing device senses a physiological signal to determine a need for therapy and generates a control signal passed to a trigger signal emitting device when therapy delivery by the therapy delivery device is required. The trigger signal emitting device emits a trigger signal that is detected by the therapy delivery device. In response to detecting the trigger signal, the therapy delivery device delivers at least a portion of a therapy.

In one example, the disclosure provides a method for controlling automated delivery of therapeutic stimulation pulses by a medical device system. The method comprises sensing a plurality of physiological events by a first device and controlling a transducer by the first device to emit a plurality of trigger signals in response to the sensed plurality of physiological events. The plurality of trigger signals have a first combined total time duration over the plurality of physiological events. The method further comprises detecting the plurality of trigger signals by a second device and delivering a plurality of therapeutic stimulation pulses by the second device in response to detecting the plurality of trigger signals. The plurality of therapeutic stimulation pulses have a second combined total time duration over the plurality of physiological events that is greater than the first combined total time duration.

In another example, the disclosure provides an implantable medical device (IMD) system for controlling automated delivery of therapeutic stimulation pulses. The system comprises a transducer for emitting a trigger signal, a first device configured to sense a plurality of physiological events and control the transducer to produce a plurality of trigger signals in response to the sensed plurality of physiological events. The plurality of trigger signals have a first combined total time duration over the plurality of physiological events. The system further includes a second device configured to detect the plurality of trigger signals and deliver a plurality of therapeutic stimulation pulses in response to detecting the plurality of trigger signals. The plurality of therapeutic stimulation pulses have a second combined total time duration over the plurality of physiological events that is greater than the first combined total time duration.

In yet another example, the disclosure provides a non-transitory, computer-readable storage medium storing a set of instructions that, when executed by a processor of an implantable medical device system, cause the system to sense a plurality of physiological events by a first device and control a transducer to emit a plurality of trigger signals in response to the sensed plurality of physiological events. The plurality of trigger signals having a first combined total time duration over the plurality of physiological events. The executed instructions further cause the system to detect the plurality of trigger signals by a second device and deliver a plurality of therapeutic stimulation pulses by the second device in response to detecting the plurality of trigger signals. The plurality of therapeutic stimulation pulses have a second combined total time duration over the plurality of physiological events that is greater than the first combined total time duration.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
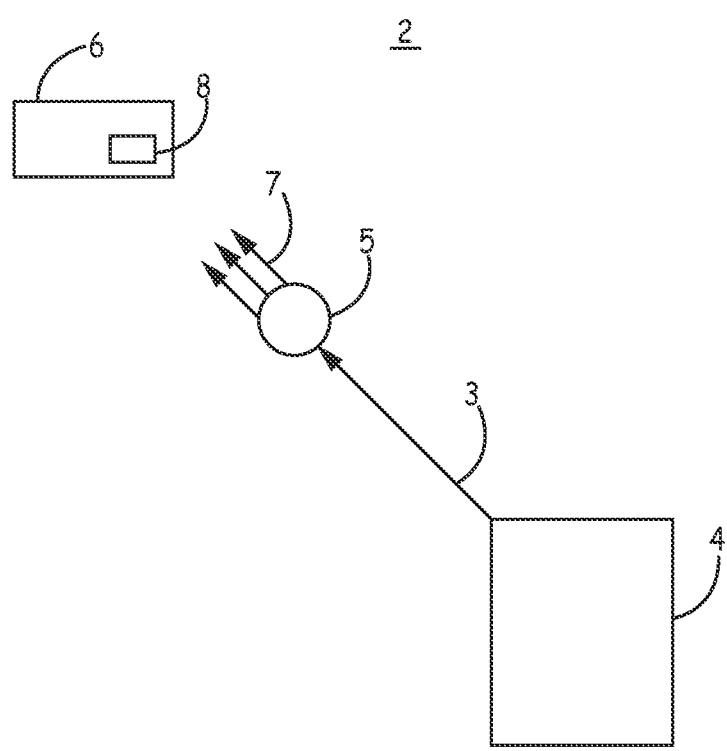
FIG. 1 is a conceptual diagram of an IMD system in which a triggered therapy delivery device may be implemented.

IMD systems and associated techniques are disclosed herein for sensing physiological signals using a sensing device implanted at one location and triggering a therapy delivery device to deliver an automatic therapy to a targeted patient tissue at a second location. A trigger signal is initiated by the sensing device and detected by a transducer included in the therapy delivery device. Automatic therapy delivery is achieved by the separate sensing and therapy delivery devices without requiring the two devices to be physically connected to each other. Among other things, elimination of the physical connection between the sensing and therapy delivery components of an IMD system enables minimally invasive implant procedures to be used, downsizing of IMD system components and power supply, and/or elimination of some components such as medical leads, sensing capability in the therapy delivery device, and a radio frequency (RF) transmitter in the therapy delivery device.

The trigger signal is a command, which is generated by and sent from a sensing device to a therapy delivery device via an emitting device to trigger the delivery of therapy by the therapy delivery device upon detection of the trigger signal. As used herein, a "trigger signal" is a signal emitted by a transducer when an electrical signal is applied to the transducer. Examples of a trigger signal include an acoustical signal, e.g., sound waves having a frequency in the ultrasonic range produced an acoustical transducer. Another example of a trigger signal is an optical signal produced by a light emitting diode (LED), vertical cavity surface emitting laser (VCSEL) or other optical transducer. In some systems, an RF signal emitted by an RF antenna is the trigger signal that is detected by the therapy delivery device and causes the therapy delivery device to deliver therapy.

A "triggered therapy delivery device" as used herein is a device that is triggered by the trigger signal to deliver a therapy to a targeted patient tissue. In the illustrative embodiments described herein, the therapy is an electrical stimulation therapy, such as cardiac pacing pulses, though other types of therapy, such as drug delivery, are contemplated. The triggered therapy delivery device includes a transducer that produces an electrical signal in response to being subjected to the trigger signal. The electrical signal is compared to a trigger signal detection threshold and causes the therapy delivery device to deliver a therapeutic stimulation pulse to a targeted tissue of the patient when the detection threshold is exceeded. The "triggered therapy delivery device" as disclosed herein, therefore, is not making a decision to deliver therapy based on sensing and processing of a physiological signal using a transducer such as a pressure transducer, optical transducer, electrode or other transducer that produces a time-varying signal waveform (e.g., ECG, blood pressure, etc.) correlated to a physiological condition or physiological events. The decision to deliver therapy is made by a sensing device that is controlling the transducer that emits the trigger signal. The sensing device and the therapy delivery device need not be in wired connection with each other.

FIG. 1 is a conceptual diagram of an IMD system 2 in which a triggered therapy delivery device may be implemented. System 2 includes a sensing device 4, a trigger signal emitting device 5, and a therapy delivery device 6. Sensing device 4 is capable of sensing a physiological signal for determining when a therapy is needed. Sensing device 4 may or may not be capable of delivering a therapy directly to the patient. Sensing device 4 is at least capable of sensing a physiological signal, determining need for therapy based on the physiological signal, and producing a control signal 3 passed to emitting device 5. In various examples, sensing device 4 may be a pacemaker, ICD, ECG monitor, hemodynamic monitor, neurostimulator, drug pump, or other IMD.

Sensing device 4 is in wired or wireless communication with trigger signal emitting device 5. Sensing device 4 sends a control signal 3 to emitting device 5 to cause emitting device 5 to emit a trigger signal 7, shown as a directionally focused signal in FIG. 1. In other embodiments, trigger signal 7 may be multi-directional (e.g., non-focused).

In the diagram, emitting device 5 is shown as a separate device from sensing device 4, however in some examples emitting device 5 is incorporated in sensing device 4. In some applications, sensing device 4 incorporating emitting device 5 may be implanted (or located externally) at a location that is within a trigger signal receiving range of therapy delivery device 6. In other applications, the physical locations of sensing device 4 and therapy delivery device 6 may be too far apart or separated by highly reflective tissues or attenuating structures that would prohibit reliable reception of a trigger signal by therapy delivery device 6. In these situations, the emitting device 5 is located at a spaced apart location from sensing device 4 and positioned to reliably transmit a trigger signal to therapy delivery device 6.

In various embodiments, sensing device 4 may sense any physiological signal or combination of physiological signals used in a particular application for determining a need for therapy. Such signals may include, but are not limited to, an electrical signal such as an ECG (electrocardiogram), EGM (cardiac electrogram), EMG (electromyogram), or EEG (electroencephalogram) or nerve action potentials. Additionally or alternatively, sensing device 4 may be configured to sense a mechanical or chemical physiological signal that may include, without limitation, a blood or other pressure signal, an optical signal such as an optical signal used to determine blood or tissue oxygen saturation, an acoustical signal such as heart sounds, an activity signal, or a posture signal.

The physiological signals may be used to determine a need for therapy and for controlling the time that therapy delivery device 6 is triggered to deliver therapy relative to sensed physiological events. As such, sensing device 4 is configured to determine a time that therapy is needed according to programmed therapy delivery algorithms and therapy delivery control parameters for a given application. Sensing device 4 controls the timing of therapy delivery by therapy delivery device 6 via trigger signal emitting device 5.

When sensing device 4 determines that it is time for a therapy to be delivered, control signal 3 is passed to signal emitting device 5. Emitting device 5 may be physically coupled to sensing device 4 by a medical lead for passing the control signal as an electrical signal to emitting device 5. Alternatively, the control signal 3 is a communication signal transmitted wirelessly to emitting device 5, from sensing device 4, such as a radio frequency (RF) command signal that causes emitting device 5 to emit a trigger signal 7.

Therapy delivery device 6 includes a trigger signal receiver 8, which includes a transducer that receives the trigger signal 7 and coverts it to an electrical signal. The electrical signal is compared to a threshold to detect the trigger signal 7. In response to detecting the trigger signal 7, therapy delivery device 6 delivers a therapy, such as one or more electrical stimulation pulses.

In some embodiments, the trigger signal 7 is an "acoustical trigger signal" which refers to a vibrational sound signal produced by an acoustical transducer in the emitting device 5 and is received by transducer 8 implemented as an acoustical transducer in the therapy delivery device 6. The acoustical trigger signal is not a sensed physiological signal that is produced, for example, by sound vibrations of the patient's heart, muscle, lungs, or other moving body part acting on a transducer. The acoustical trigger signal is generated by emitting device 5 when an electrical control signal 3, such as a logic signal, is produced by the circuitry of the sensing device 4. The electrical control signal 3 may be generated based on physiological signals, including physiological acoustical signals, sensed by the sensing device. The acoustical trigger signal itself, however, is originated by a device-generated electrical control signal 3 produced by sensing device 4 to activate the transducer of emitting device 5. The acoustical trigger signal 7 is not a signal produced by physiological body or vibration acting directly on the transducer 8 configured to detect the trigger signal.

In other embodiments, the trigger signal 7 is an "optical trigger signal" which refers to a light signal produced by an optical transducer in the emitting device 5 and is received by a transducer 8 implemented as an optical transducer in the therapy delivery device 6. The optical trigger signal is not a sensed physiological signal that is produced, for example, by sensing remitted light from a patient's body tissue or blood for determining a physiological parameter such as tissue color, oxygen saturation, hemoglobin concentration, or other chromophore concentration. The optical trigger signal is generated when electrical control signal 3, such as a logic signal, is produced by the circuitry of the sensing device 4. The electrical control signal 3 is generated based on physiological signals that are sensed by the sensing device 4, which may include physiological optical signals. The optical trigger signal itself is originated by a device-generated electrical control signal 3 activating the emitting device transducer. The optical trigger signal 7 is not a signal produced by measuring light attenuation by body tissue or blood using the transducer 8. Rather, transducer 8 is configured to detect the device-generated trigger signal 7 but not a physiological signal.

Other types of trigger signals are contemplated including radio frequency (RF) signals that are emitted by a transmitting antenna of the emitting device 5 and received by a receiving antenna in the therapy delivery device 6. The therapy delivery device 6, however, may not include a standard RF transceiver for high fidelity wireless communication. For example, therapy delivery device 6 may include an antenna, a rectifier and filter and a digital comparator for receiving and detecting trigger signal 7 (generated as an RF signal in this example) without amplification.

Therapy delivery device 6 is generally a miniaturized device that is adapted for implantation at a targeted therapy delivery site. In some applications, the target therapy delivery site requires a minimized device size in order to avoid complications, minimize patient discomfort, and/or facilitate minimally invasive implantation procedures. As such, therapy delivery device 6 may have reduced functionality for sensing physiological signals, collecting and storing data, radio frequency or other bi-directional, high fidelity telemetry communication, or other functions that may normally be present in a pacemaker, ICD, neurostimulator or other type of IMD configured to automatically deliver a therapy to a patient.

For example, therapy delivery device 6 may be a transcatheter pulse generator having electrodes positioned along the housing of the device. In some examples, a short lead carrying one or more electrodes may extend from device 6. In the illustrative embodiments described in greater detail below, the therapy delivery device 6 is a transcatheter, intracardiac pacemaker that is triggered by a signal from emitting device 5 to deliver one or more cardiac pacing pulses. As used herein, a "transcatheter" pacemaker or other transcatheter device is a device that can be implanted at a target location via a catheter or other elongated, tubular delivery tool to advance the device to a target location without necessarily having direct line of sight at the target location. Therapy delivery device 6 is not limited to being a cardiac pacemaker. Device 6 may be embodied as other types of electrical stimulation therapy delivery devices, such as devices configured for delivering electrical stimulation to any excitable tissue, including the central nervous system, peripheral nervous system, smooth muscle tissue and/or skeletal muscle tissue.

Furthermore, it is recognized that triggered therapy delivery device 6 is not limited to an electrical stimulation therapy delivery device. In alternative embodiments, therapy delivery device 6 may be configured to deliver other types of therapies using mechanical, optical, pharmaceutical or other therapeutic means. For example, therapy delivery device 6 may be a fluid delivery device for delivering a drug or biological agent.

Figure 2A:
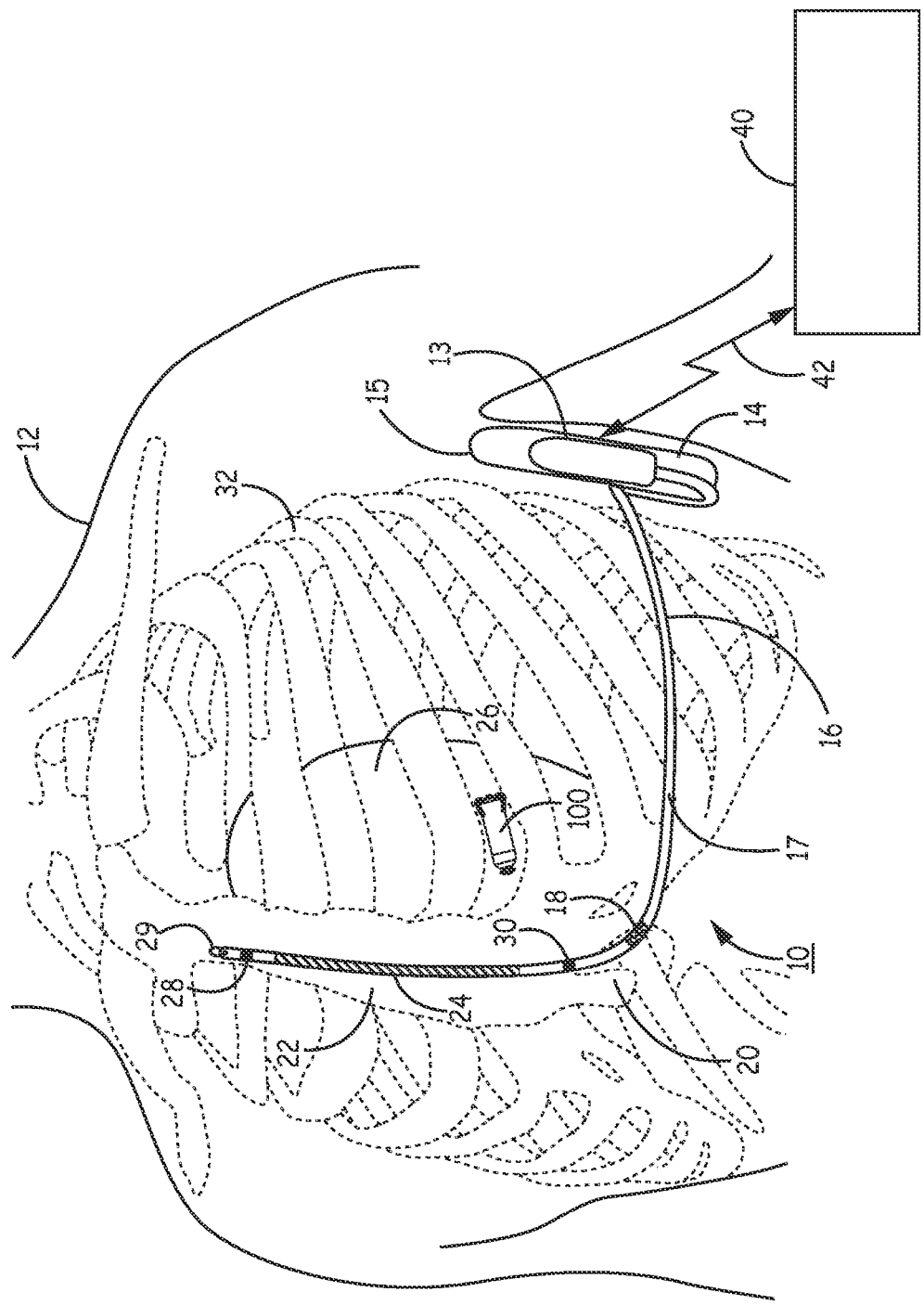
FIG. 2A is a conceptual diagram illustrating an implantable medical device (IMD) system that may be used to sense cardiac electrical signals and provide therapy to a patient.

FIG. 2A is a conceptual diagram illustrating an implantable medical device (IMD) system 10 that may be used to sense cardiac electrical signals in patient 12 and provide therapy to heart 26. IMD system 10 includes an intracardiac pacemaker 100 and a sensing device embodied as an ICD 14 coupled to an extravascular lead 16. ICD 14 is implanted subcutaneously on the left side of patient 12. Defibrillation lead 16 includes a defibrillation electrode 24, which may be an elongated coil electrode, a pair of sensing electrodes 28 and 30, illustrated as ring electrodes but may be or other types of electrodes, and a trigger signal emitting device 18. Trigger signal emitting device 18 includes a transducer that is controlled by ICD 14 to emit trigger signals to cause pacemaker 100 to deliver one or more pacing pulses.

ICD 14 is shown implanted subcutaneously on the left side of patient 12. Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is over sternum 22 or offset laterally to the left or right side of the body of sternum 22 and may be implanted subcutaneously, e.g., between the skin and the ribs or sternum. Defibrillation lead 16 may be implanted at other locations or angles relative to sternum 22 or positioned further superior or inferior depending on the location of ICD 14, position of electrodes 24, 28, and 30 and trigger signal emitting device 18 along lead 16 and the location of pacemaker 100, or other factors. In other instances, lead 16 may be implanted at other extravascular locations. In one example, lead 16 may be implanted at least partially in a substernal location or within ribcage 32, within the thoracic cavity and within or outside the pericardium, not necessarily in direct contact with heart 26.

Defibrillation lead 16 is placed along sternum 22 such that a therapy vector between defibrillation electrode 24 and a second electrode (such as a portion of the housing 15 of ICD 14 or an electrode placed on a second lead) is substantially across one or both ventricles of heart 26. The therapy vector may, in one example, be viewed as a line that extends from a point on the defibrillation electrode 24 to a point on the housing 15 (sometimes referred to as "can electrode") of ICD 14. In another example, defibrillation lead 16 may be placed along sternum 22 such that a therapy vector between defibrillation electrode 24 and housing 15 of ICD 14 (or other electrode) is substantially across an atrium of heart 26. In this case, system 10 may be used to provide atrial therapies, such as therapies to treat atrial fibrillation.

Trigger signal emitting device 18 is positioned to establish a trigger signal transmission pathway that does not excessively attenuate the trigger signal transmitted from emitting device 18 to a receiver or detector included in intracardiac pacemaker 100. For example, the location of emitting device 18 may be selected so that a direct pathway between emitting device 18 and pacemaker 100 avoids, as much as possible, tissues that are highly reflective, scattering or absorbing of the type of trigger signal being used. When lead 16 is positioned extra-thoracically, emitting device 18 may be positioned inferior to the xyphoid process 20 in a position approximately as shown. Emitting device 18 is positioned relative to pacemaker 100 to establish an efficient trigger signal transmission pathway, which may be a direct or indirect pathway that takes into account the trigger signal properties and the transmission or attenuation properties of the surrounding and intervening tissues for the type of trigger signal being used.

For example, the location of emitting device 18, when embodied as an acoustical emitting device, may be selected so that a direct acoustical pathway between emitting device 18 and pacemaker 100 avoids lung tissue as much as possible. In another example, the location of emitting device 18, when embodied as an optical emitting device, may be selected so that a direct optical pathway between emitting device 18 and pacemaker 100 avoids a large blood volume and is directed primarily through lung tissue.

Defibrillation lead 16 may include an attachment feature 29 at or toward the distal end of lead 16. The attachment feature 29 may be a loop, link, or other attachment feature useful to aid in implantation of lead 16 and/or for securing lead 16 to a desired implant location. In some instances, defibrillation lead 16 may include a fixation mechanism in addition to or instead of the attachment feature 29. For example, defibrillation lead 16 may include a suture sleeve or other fixation mechanism (not shown) located proximal to electrode 30 or near emitting device 18 that is configured to fixate lead 16 near the xiphoid process 20 or lower sternum location. The fixation mechanism (e.g., suture sleeve or other mechanism) may be integral to the lead or may be added by the user prior to implantation. The fixation mechanism may be used to stably locate emitting device 18 inferior to the xyphoid process 20, along an intercostal space, or other desired location to prevent rotation or shifting of the emitting device 18 that may cause trigger signal misdirection or trigger signal loss due to interference or attenuation by body tissues.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 22. When the ICD 14 is implanted in the pectoral region, the system 10 may include a second lead including a defibrillation electrode, and optionally a trigger signal emitting device, that extends along the left side of the patient such that the defibrillation electrode of the second lead is located along the left side of the patient to function as an anode or cathode of the therapy vector for defibrillating heart 26.

ICD 14 includes a housing 15 that forms a hermetic seal that protects components within ICD 14. The housing 15 of ICD 14 may be formed of a conductive material, such as titanium or other biocompatible conductive material or a combination of conductive and non-conductive materials. Housing 15 may enclose one or more components, including processors, memories, transmitters, receivers, sensors, sensing circuitry, therapy circuitry and other appropriate components (often referred to herein as modules). In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

ICD 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing 15. Depending on the intended implant location of ICD 14, a trigger signal emitting device may be included in connector assembly 13 and/or housing 15 in addition to or in place of the emitting device 18 carried by lead 16 for transmitting trigger signals to pacemaker 100.

Lead 16 includes a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly 13 of ICD 14. The lead body 17 of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

Defibrillation lead 16 includes elongated electrical conductors (not illustrated) that extend within the elongated lead body 17 from the connector on the proximal end of defibrillation lead 16 to the respective electrodes 24, 28 and 30 and emitting device 18. Although defibrillation lead 16 is illustrated as including three electrodes 24, 28 and 30, defibrillation lead 16 may include more or fewer electrodes. When the connector at the proximal end of defibrillation lead 16 is connected to connector assembly 13, the respective conductors electrically couple to circuitry of ICD 14, such as a therapy delivery module, a sensing module, or trigger signal drive signal circuit, via connections in connector assembly 13, including associated feedthroughs.

The electrical conductors transmit electrical stimulation pulses from a therapy module within ICD 14 to one or more of electrodes 24, 28 and 30 and transmit sensed electrical signals from one or more of electrodes 24, 28 and 30 to the sensing module within ICD 14. An electrical conductor extending from the proximal lead connector to emitting device 18 conducts an electrical control signal to emitting device 18 to cause emitting device 18 to emit a trigger signal at appropriate times for causing intracardiac pacemaker 100 to deliver one or more pacing pulses to heart 26.

ICD 14 may sense electrical activity of heart 26 via one or more sensing vectors that include combinations of electrodes 28 and 30 and housing 15. For example, ICD 14 may obtain cardiac electrical signals sensed using a sensing vector between electrodes 28 and 30, between electrode 28 and the conductive housing 15, between electrode 30 and the conductive housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15 of ICD 14.

ICD 14 determines a need for pacing therapy in response to the sensed cardiac electrical signals, which may include P-waves and R-waves for example, and controls emitting device 18 to emit trigger signals based on that determination. The need for pacing pulses may be determined according to programmed single chamber, dual chamber or multi-chamber bradycardia or CRT control parameters or other cardiac pacing therapy parameters. ICD 14 may also analyze the sensed electrical signals to detect tachyarrhythmia, such as ventricular tachycardia or ventricular fibrillation, and in response to detecting tachyarrhythmia may generate and deliver an electrical stimulation therapy to heart 26. For example, ICD 14 may deliver one or more defibrillation shocks via a therapy vector that includes defibrillation electrode 24 of defibrillation lead 16 and the housing 15.

Electrodes 24, 28, 30 and housing 50 may be used for sensing ECG signals for use in controlling the timing of an R-wave synchronized shock delivered by ICD 14 and for controlling timing of pacing pulses delivered by pacemaker 100. In some instances, one or more pacing therapies may be delivered prior to or after delivery of a defibrillation shock by ICD 14, such as anti-tachycardia pacing (ATP) or post shock pacing. In these instances, ICD 14 may generate and deliver pacing pulses via therapy vectors that include electrodes 24, 28, 30 and/or housing 15. Alternatively, ICD 14 causes trigger signal emitting device 18 to emit trigger signals to cause pacemaker 100 to deliver pacing pulses to heart 26 at appropriate times when ATP or post-shock pacing is needed as well as when bradycardia or CRT pacing therapy is needed.

The example ICD 14 illustrated in FIG. 2A is illustrative in nature and should not be considered limiting of the sensing device used in a triggered therapy delivery system and associated techniques described in this disclosure. For instance, in addition to sensing ECG signals, ICD 14 may include shock therapy capabilities only without pacing therapy capabilities. In other examples, ICD 14 may be coupled to more than one lead for sensing ECG signals and/or sending trigger signals to pacemaker 100. In still other examples, a sensing device may be substituted for ICD 14 that is a single chamber or dual chamber subcutaneous pacemaker without cardioversion/defibrillation capabilities or a sensing-only device without therapy delivery capabilities, e.g., as shown in FIG. 3C. Any of these sensing devices may be coupled to housing-based electrodes and/or electrodes carried by a transvenous, intracardiac or extravascular, extracardiac lead for sensing a cardiac electrical signal and determining appropriate times for triggering pacemaker 100 to delivery therapy.

Pacemaker 100 is a transcatheter intracardiac pacemaker adapted for implantation wholly within a heart chamber, e.g., wholly within the RV, wholly within the LV, wholly within the right atrium (RA) or wholly within the left atrium (LA) of heart 26. In the example of FIG. 2A, pacemaker 100 is positioned proximate to an inner wall of the LV to provide left ventricular pacing. In other examples, pacemaker 100 is positioned proximate to an inner wall of the right ventricle to provide right ventricular pacing. In other examples, pacemaker 100 may be positioned at any other location outside or within heart 26, including epicardial locations. For example, pacemaker 100 may be positioned outside or within the right atrium or left atrium, e.g., to provide respective right atrial or left atrial pacing. In other embodiments, pacemaker 100 may be embodied as therapy delivery device for delivering an electrical stimulation therapy at another body location. Pacemaker 100 is shown as a leadless device in FIG. 2A. It is contemplated, however that in other embodiments pacemaker 100 may be coupled to a lead extending from pacemaker 100 to position therapy delivery electrodes at a location spaced apart from pacemaker 100.

Depending on the implant location, pacemaker 100 may be configured to deliver an electrical stimulation therapy to target therapy site(s) other than the myocardium. For example, pacemaker 100 may provide atrioventricular nodal stimulation, fat pad stimulation, vagal stimulation, or other types of neurostimulation. In other examples, system 10 may include a plurality of pacemakers 100, e.g., to deliver electrical stimulation therapy at multiple sites of heart 26 such as within multiple heart chambers for multi-chamber pacing therapies.

Pacemaker 100 is capable of producing electrical stimulation pulses delivered to heart 26 via one or more electrodes on the outer housing of pacemaker 100. Pacemaker 100 includes a receiving transducer for receiving a trigger signal emitted by emitting device 18. In response to detecting the trigger signal, pacemaker 100 delivers one or more pacing pulses.

In one embodiment, pacemaker 100 includes a pulse generator configured to deliver one or more pacing pulses upon receiving the trigger signal from emitting device 18. Pacemaker 100 may not be configured to sense cardiac signals. Cardiac signal sensing is performed by ICD 14. ICD 14 senses ECG signals through lead 16 and controls pacing delivered by pacemaker 100 via trigger signals emitted by emitting device 18 under the control of ICD 14.

An intracardiac pacemaker 100 may or may not be configured to sense cardiac signals. Pacemaker 100 may rely solely on a trigger signal from emitting device 18 for controlling the timing of pacing pulse delivery without sensing any other cardiac electrical event signals or any other physiological signals. In order to minimize the size of pacemaker 100, some functions such as cardiac signal sensing and radio frequency telemetry functions may be omitted such that pacemaker 100 includes a pulse generator with limited memory, processing, and other functions directed to therapy delivery.

In other embodiments, pacemaker 100 senses EGM signals in the heart chamber in which it is implanted. Since pacemaker 100 is positioned wholly within a heart chamber, however, the EGM signal sensed by pacemaker 100 will be less sensitive or insensitive to P-waves and/or R-waves occurring in other heart chambers. In past practice, a subcutaneous pacemaker might be coupled to one or more leads that position sense electrodes in or along multiple heart chambers such that multiple sensing channels can be monitored. By monitoring multiple sensing channels, coordinated pacing pulses can be delivered to one or more heart chambers at specified time intervals, e.g., AV or VV intervals.

Since pacemaker 100 may have no or limited sensing capabilities, pacemaker 100 may be "blinded" to intrinsic events, such as intrinsic R-waves, occurring in the same heart chamber and to paced or intrinsic events occurring in other heart chambers. Delivery of CRT, dual chamber pacing, or other multi-chamber pacing therapies may require delivering a pacing pulse at a predetermined time interval after an event, sensed or paced, in another heart chamber. As such, emitting device 18 provides a trigger signal to pacemaker 100 in response to ECG signals sensed by ICD 14 to cause pacing pulses to be delivered by pacemaker 100 at desired time intervals relative to other heart chamber events. Pacemaker 100 (for generating pacing pulses) combined with ICD 14 (for sensing physiological signals and making therapy delivery decisions) provides the functionality required to deliver various therapies that may require synchronization or coordination with cardiac events occurring in the same or a different heart chamber without physical connection between pacemaker 100 and ICD 14 implanted at separate implant sites.

FIG. 2A further depicts programmer 40 in wireless communication with ICD 14 via communication link 42. In some examples, programmer 40 comprises a handheld computing device, computer workstation, or networked computing device. Programmer 40 includes a user interface that presents information to and receives input from a user. It should be noted that the user may also interact with programmer 40 remotely via a networked computing device.

A user, such as a physician, technician, surgeon, electrophysiologist, other caregiver, or patient, interacts with programmer 40 to communicate with ICD 14. For example, the user may interact with programmer 40 to retrieve physiological or diagnostic information from ICD 14. A user may also interact with programmer 40 to program ICD 14, e.g., select values for operational parameters of the ICD 14, including parameters used to control trigger signal emitting device 18 for controlling pacemaker 100. A user may use programmer 40 to retrieve information from ICD 14 regarding the rhythm of heart 26, heart rhythm trends over time, or arrhythmic episodes.

As indicated, ICD 14 and programmer 40 communicate via wireless communication. Examples of communication techniques may include low frequency or radiofrequency (RF) telemetry, but other techniques may be used. In some examples, programmer 40 may include a programming head that is placed proximate to the patient's body near the ICD 14 implant site in order to improve the quality or security of communication between ICD 14 and programmer 40.

The embodiment illustrated in FIG. 2A is an example configuration of an IMD system 10 and should not be considered limiting of the techniques described herein. In other embodiments, ICD 14 may be coupled to a transvenous intracardiac lead extending into the right ventricle (RV) for positioning RV sensing and pacing electrodes and a defibrillation coil electrode within the RV. An example of an RV lead that could be adapted to carry an emitting device 18 is generally disclosed in commonly-assigned, U.S. Pat. No. 5,545,186 (Olson, et al.). In this example, emitting device 18 may be positioned more distally than the position shown on lead 16 such that the emitting device 18 is positioned in the RV, opposite pacemaker 100 in the LV. Emitting device 18 may then be enabled to emit a trigger signal from the RV to the pacemaker 100 in the LV to coordinate timing of the LV pacing pulse relative to a right atrial event or a right ventricular event. It is contemplated that numerous configurations of a lead-based emitting device 18 may be conceived and emitting device 18 may be positioned along the lead body 17 at relatively more proximal or more distal locations than shown on lead 16 to position emitting device 18 at a desired location relative to pacemaker 100.

Figure 2B:
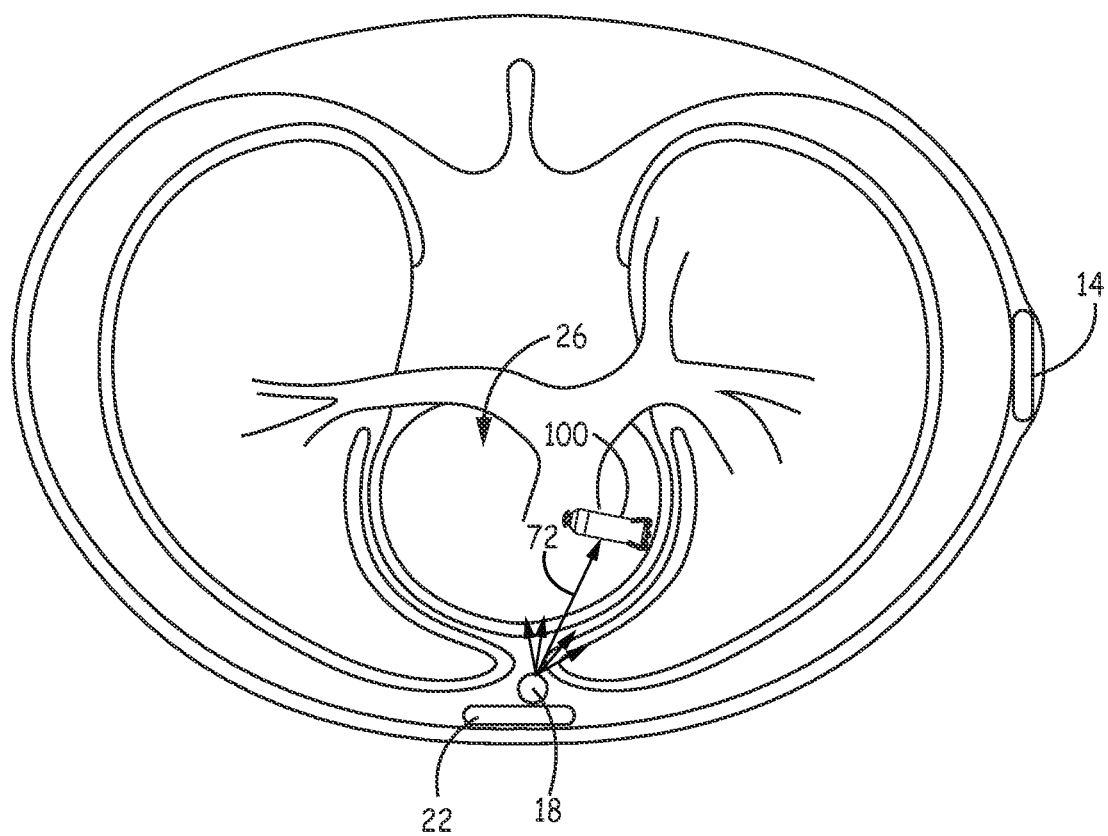
FIG. 2B is a sectional view of the patient's anatomy depicting an alternative configuration of system 10 of FIG. 2A.

FIG. 2B is a sectional view of the patient's anatomy depicting an alternative configuration of system 10 of FIG. 2A. Emitting device 18 is shown in a substernal position on lead 16 (not seen in the sectional view of FIG. 2B). Instead of being positioned suprasternally, inferior to the xyphoid process, emitting device 18 may be positioned substernally and relatively more superior by advancing the distal end of lead 16 to a substernal location. Emitting device 18 may be configured for directional trigger signal emission with emitting device 18 oriented to generally direct the trigger signal toward the implant position of pacemaker 100, e.g., along a signal pathway to pacemaker 100 as represented by arrow 72.

Lead 16 may be placed under or below the sternum in the mediastinum and, more particularly, in the anterior mediastinum. The anterior mediastinum is bounded laterally by pleurae, posteriorly by pericardium, and anteriorly by sternum. Lead 16 may be at least partially implanted in other extra-pericardial locations, i.e., locations in the region around, but not necessarily in direct contact with, the outer surface of heart 26. These other extra-pericardial locations may include in the mediastinum but offset from sternum 22, in the superior mediastinum, in the middle mediastinum, in the posterior mediastinum, in the sub-xiphoid or inferior xiphoid area, near the apex of the heart, or other location not in direct contact with heart 26 and not subcutaneous. In other embodiments, lead 16 may extend within the pericardium and in direct contact with heart 26. In any of these illustrative implant locations, lead 16 may be positioned to optimally position trigger signal emitting device 18 for reliably transmitting a trigger signal to pacemaker 100.

Figure 3A:
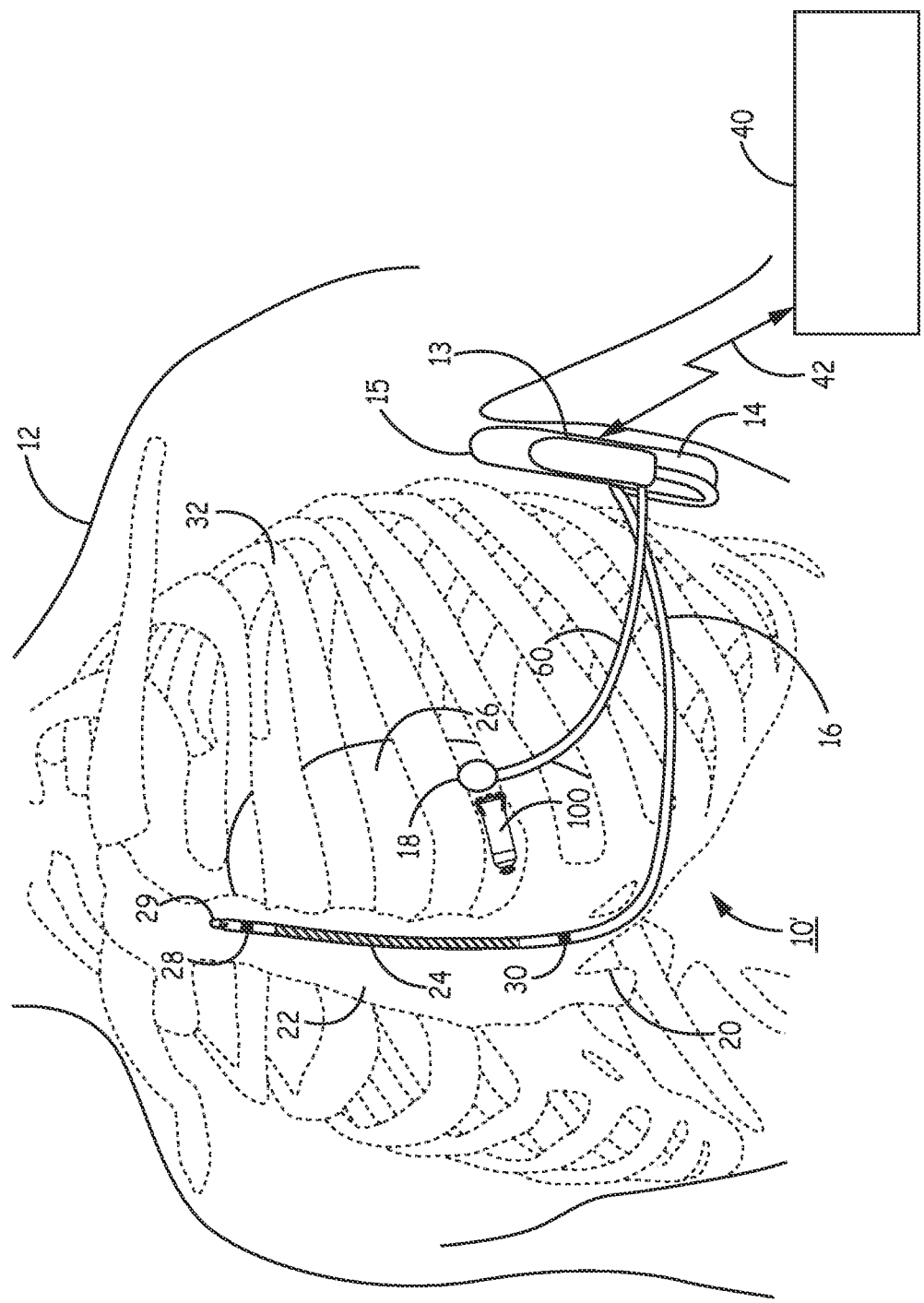
FIG. 3A is a conceptual diagram illustrating an IMD system according to an alternative example.

FIG. 3A is a conceptual diagram illustrating an IMD system 10' according to an alternative example. ICD 14 coupled to lead 16 is used to sense cardiac electrical signals in patient 12 and provide therapy to heart 26 as described above. Intracardiac leadless pacemaker 100 is implanted within the LV and delivers pacing pulses to the LV in response to receiving a trigger signal. In this embodiment, trigger signal emitting device 18 is carried by a separate lead 60 coupled to ICD 14 and positioned extrathoracically, e.g., along an intercostal space, to direct a trigger signal toward pacemaker 100 through the intercostal space and intervening muscle, blood, myocardial tissue, etc. Emitting device 18 is capable of receiving an electrical control signal from ICD 14 conducted along lead 60. Upon receipt of the control signal, emitting device 18 emits a trigger signal to cause pacemaker 100 to deliver an LV pacing pulse.

A dedicated lead 60 carrying emitting device 18 may be provided to position emitting device 18 at an optimal location for transmitting a trigger signal to pacemaker 100. An optimal location is a location of emitting device 18 relative to pacemaker 100 that allows a trigger signal to reach pacemaker 100 with adequate signal intensity and signal-to-noise ratio that it is reliably detected by pacemaker 100. A trigger signal path between emitting device 18 and pacemaker 100 may include tissues that attenuate the trigger signal through absorption, scattering or reflection of the signal. The location of emitting device 18 is selected such that signal losses along the path do not reduce the intensity of the trigger signal below a threshold level that is detectable by pacemaker 100.

In some examples, emitting device 18 may have its own battery, which may be rechargeable, such that the power required by ICD 14 for sensing and therapy delivery functions and the power required for trigger signal emission is distributed across two devices and two (or more) batteries or other power sources.

Emitting device 18 may alternatively be embodied as a leadless device capable of receiving a wireless control signal from ICD 14 to cause trigger signal emission. For example, emitting device 18 may include an RF receiver for receiving a wireless RF control signal from ICD 14.

Emitting device 18 carried by a dedicated lead 60, or a leadless emitting device, may be positioned at an optimal location for transmitting a trigger signal to pacemaker 100 without limitations associated with optimal positioning of electrodes 24, 28 and 30 for sensing ECG signals and delivering shock therapy. A leadless emitting device may be implanted at a desired site without requiring lead tunneling. The emitting device 18 may act as a relay device for transmitting the control signal from ICD 14 to pacemaker 100 by converting the control signal to a trigger signal that is transmitted to and detected by pacemaker 100.

Emitting device 18 may be positioned external to the ribcage 32 such that the trigger signal is directed through an intercostal space toward heart 26. Transmission of a trigger signal along a path through blood and muscle tissue may be more efficient than a path through lung tissue or vice versa depending on the type of trigger signal being emitted. The intensity or amplitude and frequency of the trigger signal and/or other trigger signal properties may be selected to provide efficient transmission through the tissues along the pathway between the trigger signal emitting device 18 and the receiving pacemaker 100.

In some examples, multiple emitting devices may be included in systems 10 or 10'. Depending on the final implant position of pacemaker 100 and shifting that may occur over time, pacemaker 100 may be more sensitive to a trigger signal emitted by one device than by another device at a different location. Multiple emitting devices positioned at different, spaced apart locations may be selected individually or in combination by ICD 14 to emit a trigger signal to achieve reliable trigger signal detection by pacemaker 100 using the greatest power efficiency.

Furthermore, it is contemplated that a trigger signal emitting device can be located in the ICD 14, e.g., along its housing 15 and/or connector assembly 13. In some embodiments, ICD 14 may be implanted relative to pacemaker 100 so that a trigger signal may be reliably transmitted from ICD 14 to pacemaker 100. The implant location of ICD 14 is selected to establish a defibrillation vector between electrode 24 and ICD housing 15.

Figure 3B:
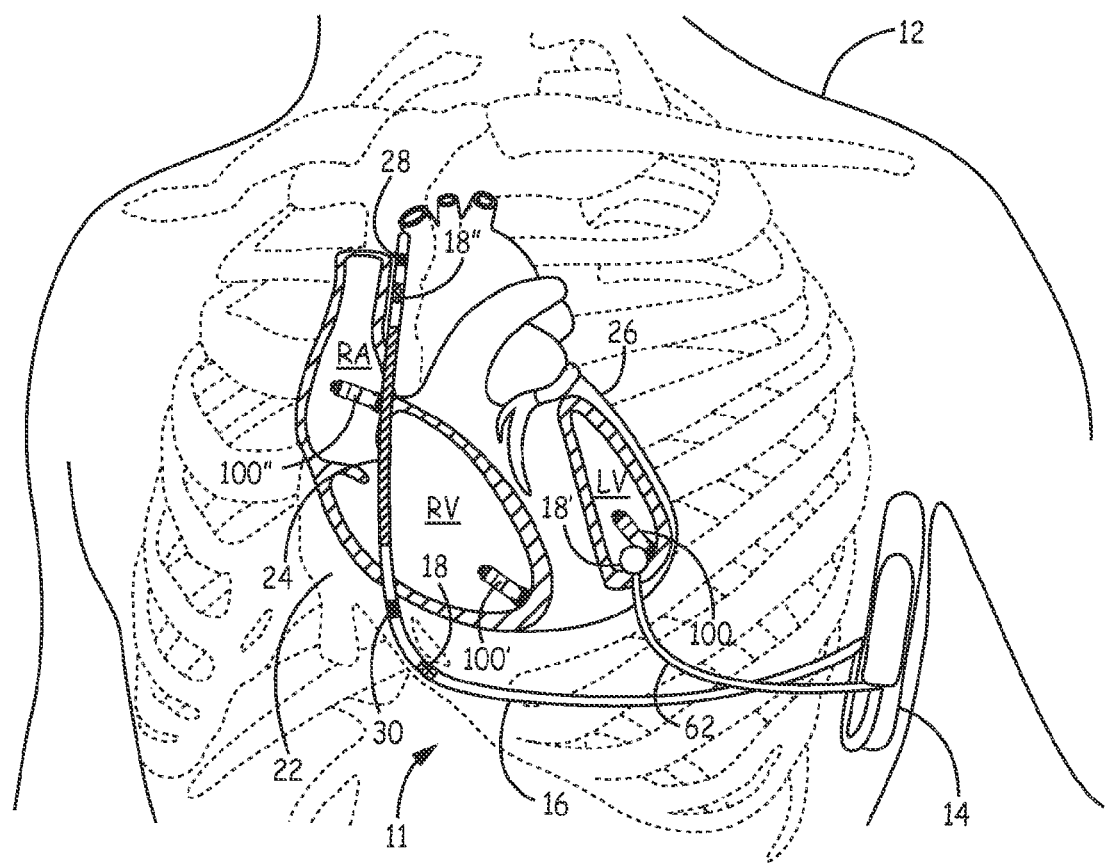
FIG. 3B is a conceptual diagram illustrating an IMD system including multiple therapy delivery devices.
Figure 3C:
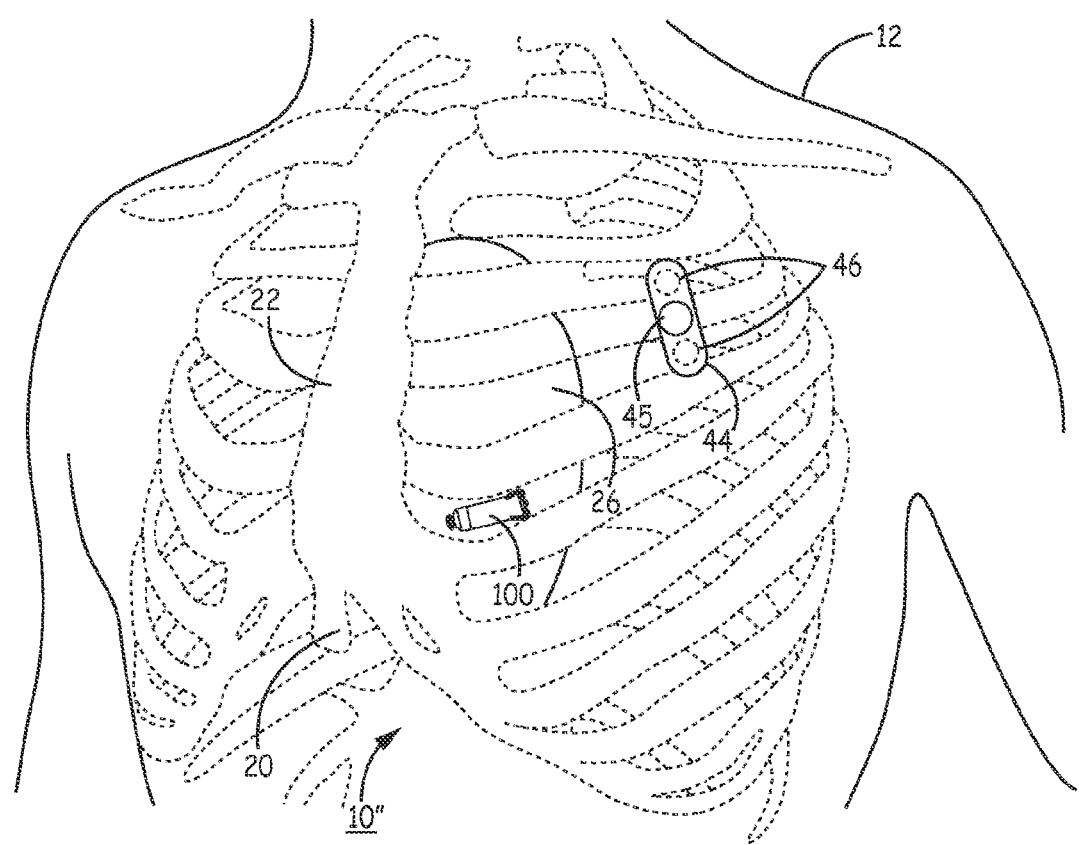
FIG. 3C is a conceptual diagram illustrating an IMD system having an alternative sensing device.

FIG. 3B is a conceptual diagram illustrating an IMD system 11 including multiple therapy delivery devices 100, 100', and 100". In the example shown, one pacemaker 100 is shown in the LV, pacemaker 100' is shown in the RV and pacemaker 100" is shown in the RA. In embodiments including multiple intracardiac pacemakers 100, 100' and 100", the receiving transducers in each pacemaker 100, 100' and 100" may be configured to be sensitive to different trigger signal frequencies, signal amplitudes, signal pulse numbers or other trigger signal characteristic. In the example shown, and as described in conjunction with FIG. 2A, the sensing device may be embodied as an ICD 14 that controls lead-based emitting device 18. Emitting device 18 may be controlled to emit a trigger signal at a first frequency, wavelength, or other signal characteristic for triggering an RV pacemaker 100' configured to detect trigger signals having the first frequency, wavelength or other characteristic (and ignore other trigger signals not having the first frequency, wavelength or other characteristic) and to emit a second trigger signal at a second frequency, wavelength or other characteristic for triggering an LV pacemaker 100 configured to detect trigger signals having the second frequency, wavelength or other characteristic. The emitting device 18 may be controlled by ICD 14 to emit a trigger signal according to the first characteristic to cause delivery of a triggered RV pacing pulse and emit a second trigger signal according to the second characteristic to trigger an LV pacing pulse at a controlled time interval (positive or negative) relative to the triggered pace in the RV. Similarly, RA pacemaker 100" may be triggered to deliver a pacing pulse in response to a third wavelength.

Alternatively, when two or more therapy delivery devices 100, 100' and 100" are included in the IMD system 11, multiple emitting devices 18, 18' and 18", each configured to target a trigger signal at one specific therapy device 100, 100' or 100" may be used. For example, paired emitting devices 18, 18' and 18" and therapy delivery devices 100, 100' and 100" may be implanted relative to each other so that each emitting device 18, 18' and 18" is positioned and controlled to focus an emitted trigger signal at a respective therapy delivery device 100, 100' and 100". To illustrate, lead-based emitting device 18 may be configured to transmit a trigger signal to pacemaker 100' positioned in the RV, a second lead-based emitting device 18' may be configured to transmit a trigger signal to pacemaker 100 positioned in the LV, and a third lead-based emitting device 18" may be configured to emit a trigger signal to pacemaker 100" positioned in the RA.

Depending on the transducer used in the emitting device 18, trigger signals may be sequentially steered or focused toward different targeted therapy delivery devices 100, 100' and 100" by a single emitting device 18. For example, if an acoustic trigger signal emitting device is used, an array of transducers may be controlled to focus the trigger signal at one therapy delivery device 100 and then controlled to focus the trigger signal at another therapy delivery device 100' and so on.

In still other examples, other trigger signal parameters besides frequency or wavelength may be used to transmit mutually exclusive trigger signals that are recognized and detected by the appropriate therapy delivery device 100, 100' or 100". For example, mutually exclusive trigger signal patterns, such as different pulse numbers, different interpulse intervals, different pulse widths, different rising and/or falling slope of a trigger signal pulse or any combination thereof may be used to exclusively trigger different therapy delivery devices 100, 100' and 100". To illustrate, one therapy delivery device 100 may detect a trigger signal having more than two pulses as invalid while another therapy delivery device 100' may require detection of a minimum of three pulses to recognize a valid trigger signal. In another example, one therapy delivery device 100 may detect a valid trigger signal having a short-long-short interpulse interval pattern and another therapy delivery device 100" may detect a valid trigger signal as one having a long-short-long interpulse interval pattern.

In other applications, as shown by system 10" in FIG. 3C, a different type of sensing device 44 may be substituted for ICD 14 that may implanted at a variety of locations that facilitate trigger signal transmission from the sensing device 44 to pacemaker 100 without requiring a lead-based or leadless emitting device spaced apart from the sensing device 44. The emitting device 45 may be incorporated along the housing of the sensing device 44. Sensing device 44 may be embodied as a sensing-only device without therapy delivery capabilities and is shown as an ECG monitor having a pair of housing-based electrodes 46 for sensing an ECG signal. Based on cardiac events sensed from the ECG signal, sensing device 44 controls emitting device 45 to emit a trigger signal to cause pacemaker 100 to deliver one or more pacing pulses.

It is recognized that a triggered therapy delivery system including any combination and arrangement of one or more therapy delivery devices, one or more emitting devices, and one or more sensing devices may be conceived to meet the needs of a particular therapeutic application based on the teachings of the present disclosure. The systems 2, 10, 10', 11 and 10" shown in FIGS. 1, 2A, 2B, 3A, 3B, and 3C, respectively, are intended to illustrate various possible combinations and arrangements of a triggered therapy delivery IMD system with no limitation intended. A therapy delivery system employing the techniques disclosed herein may include different combinations and arrangements of at least one therapy delivery device, at least one sensing device and at least one trigger signal emitting device than the combinations and arrangements shown in the accompanying drawings.

Figure 4:
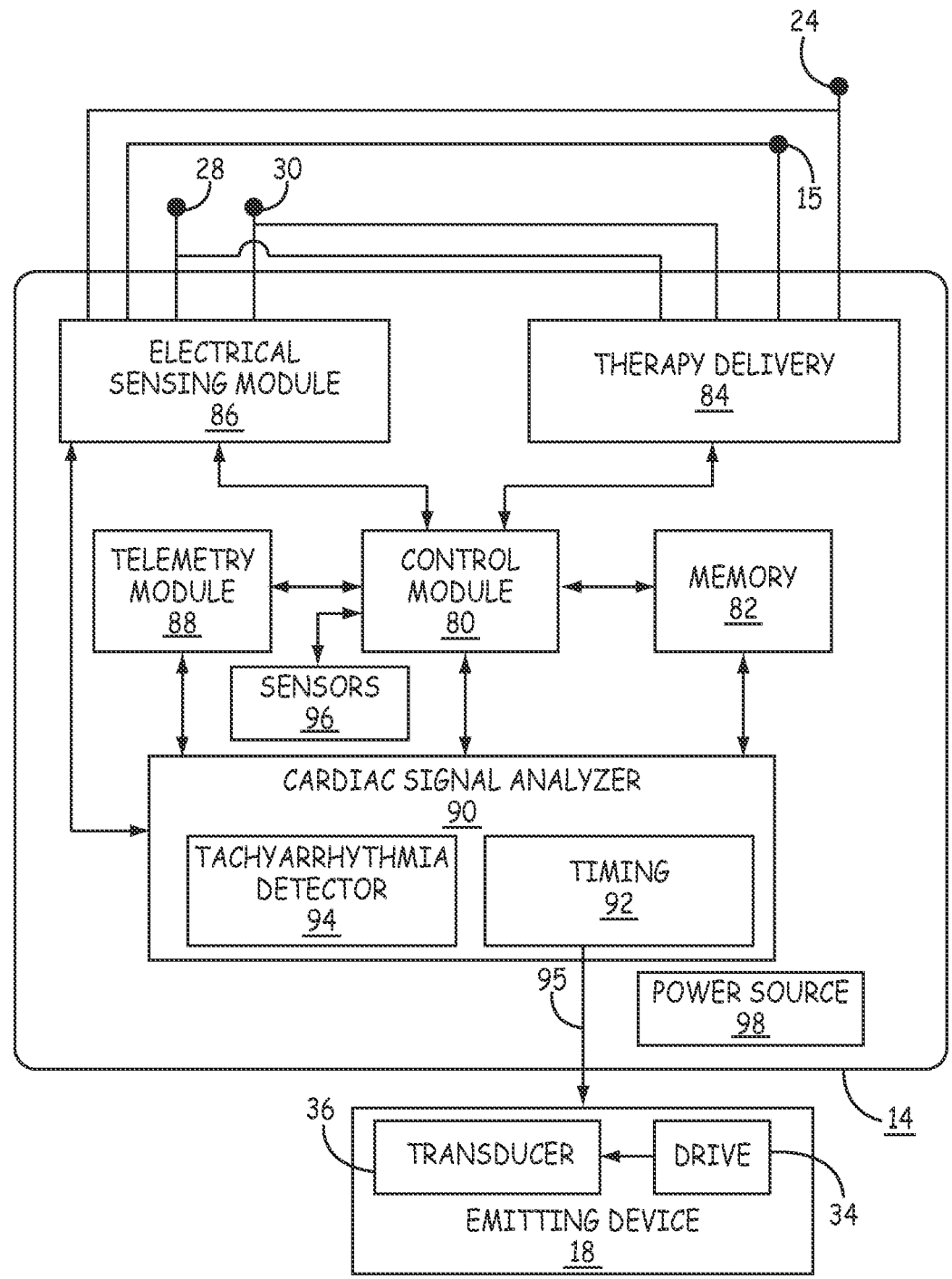
FIG. 4 is a functional block diagram of electronic circuitry that is included in one embodiment of the ICD shown in FIGS. 2A, 2B and 3.

FIG. 4 is a functional block diagram of electronic circuitry that is included in one embodiment of ICD 14 shown in FIGS. 2A, 2B and 3. ICD 14 includes processing and control module 80, also referred to as "control module" 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, 90. Power source 98 may include one or more energy storage devices, such as one or more chargeable or non-re-chargeable batteries.

The functional blocks shown in FIG. 4 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 and/or pacemaker 100 may be implemented in processing and control module 80 executing instructions stored in memory 82.

Processing and control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16, e.g., as shown in FIG. 2A, and housing 15, at least a portion of which also serves as a common or ground electrode.

Electrical sensing module 86 is coupled to electrodes 28 and 30 in order to monitor electrical activity of the patient's heart. Electrical sensing module 86 may optionally be coupled to electrodes 24 and 15 and enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers included in sensing module 86. Switching circuitry may include a switch array, switch matrix, multiplexer, or any other type of switching device suitable to selectively couple sense amplifiers to selected electrodes. A sensing vector between electrodes 28 and 30 may be selected for sensing an ECG signal, although it is recognized that in some embodiments sensing vectors may be selected that utilize coil electrode 24 and/or housing electrode 15, e.g., from electrode 28 to housing 15 or electrode 30 and housing 15.

One or more ECG signals are received by an input of sensing module 86. Sensing module 86 includes one or more sense amplifiers or other cardiac event detection circuitry for sensing cardiac events, e.g., P-waves or R-waves, from the ECG signal(s). Sensing module 86 passes sense event signals to cardiac signal analyzer 90 in response to sensing cardiac events. For example P-wave sense event signals and R-wave sense event signals are passed to cardiac signal analyzer 90 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 92. In response to the pacing escape interval expiring, a control signal 95 is passed to the trigger signal emitting device 18. The pacing escape interval is restarted upon a trigger signal or a sense event signal.

The control signal 95 in the illustrative examples presented herein may be referred to as a pacing control signal because it causes pacemaker 100 to deliver a pacing pulse to a heart chamber. In other examples, the control signal 95 may be produced by cardiac signal analyzer 90 to cause other types of therapy pulses to be delivered by pacemaker 100 (or another therapy delivery device). For example control signal 95 may be produced to cause pacemaker 100 or another therapy delivery device to deliver an ATP pulse, a vagal nerve stimulation pulse, or other type of electrical stimulation pulse.

The control signal 95 is an electrical signal that is passed to emitting device 18 along lead 16 or 60 (or another lead carrying emitting device 18) when emitting device 18 is coupled to ICD 14 in a wired connection. The control signal 95 is alternatively a wireless telemetry signal that is transmitted via telemetry module 88, to emitting device 18. Emitting device 18 may be carried by a lead but configured to wirelessly receive a control signal 95 from telemetry module 88. Alternatively, the emitting device 18 is not a lead-based emitting device and receives control signal 95 wirelessly, e.g., as an RF telemetry signal, from telemetry module 88. It is understood that in some embodiments, drive signal circuit 34 may be included within the housing 15 of ICD 14 and coupled to transducer 36 located external to housing 15.

Trigger signal emitting device 18 includes a drive signal circuit 34 that receives the control signal 95, either as a wired electrical signal or a wireless signal from telemetry module 88. Drive signal circuit 34 passes an electrical signal to transducer 36 to enable transducer 36 to emit the trigger signal. Transducer 36 may be an optical transducer or an acoustical transducer in various examples. In other examples, the drive signal circuit 34 is coupled to an antenna for transmitting the trigger signal as an RF signal.

The trigger signal is received and detected by pacemaker 100 causing pacemaker 100 to deliver one or more pacing pulses to the patient's heart. In some examples, the trigger signal is generated according to predetermined frequency, amplitude, duration and other characteristics that are not intentionally varied by emitting device 18 under the control signal 95. In other words, the trigger signal merely signals pacemaker 100 to deliver therapy without any information relating to how many pacing pulses, what pulse amplitude or pulse width or other pacing pulse control parameters. Pacemaker 100 is programmed to deliver a predetermined number of pacing pulses according to predefined pulse control parameters when the trigger signal is detected.

Alternatively, control signal 95 may include encoded pacing pulse control information. The control signal 95 generated by drive circuit 34 may cause transducer 36 to emit a trigger signal according to a frequency, duration, amplitude or other intentionally varied characteristics of the trigger signal to include pacing pulse control parameter information. As described below, a parameter of the trigger signal emitted by transducer 36 may be controllably varied by control signal 95 and drive circuit 34 to cause pacemaker 100 to adjust a pacing pulse control parameter such as pacing pulse width, pulse number, etc. Trigger signal parameters that may be varied under the control of signal 95 and drive circuit 34 include, without limitation, trigger signal amplitude, signal frequency, pulse width, pulse number and interpulse interval.

Transducer 36 may be embodied as one or more transducers configured to emit sound or light, for example, upon receiving a drive signal from circuit 34. Transducer 36 may include any combination of one or more of a ceramic piezoelectric crystal, a polymer piezoelectric crystal, capacitive micromachined ultrasonic transducer (CMUT), piezoelectric micromachined ultrasonic transducer (PMUT), or other ultrasonic transducer, a light emitting diode (LED), a vertical cavity surface emitting laser (VCSEL) or other light source having a high quantum efficiency at a selected light wavelength. Transducer 36 may include multiple transducers arranged in an array and/or configured to emit signals in multiple directions from emitting device 18 to promote reception of the trigger signal by pacemaker 100 despite shifting, rotation or other changes of the relative orientations of emitting device 18 and pacemaker 100 with respect to each other. The multiple transducers may be selectable by drive circuit 34 such that a single one or combination of transducers producing the best signal-to-noise ratio at the pacemaker receiving transducer is selected.

In one example, transducer 36 may include multiple acoustic transducers activated by drive signal circuit 34 to emit sound waves that constructively interfere to improve the efficiency of acoustical signal transmission. Emitting device 18 is shown as a single device but may be implemented as more than one emitting device such that transmission of the trigger signal is distributed over two or more emitting devices. When two or more emitting devices are used, emitting device 18 may include one or more lead-based emitting devices, one or more leadless emitting devices, and/or one or more emitting devices incorporated in ICD 14. Two or more emitting devices may be activated synchronously to produce ultrasound waves that superimpose at the receiver of pacemaker 100 to increase transmission efficiency and/or improve signal reception. A phased array of transducers that can be independently pulsed to emit sound can be used to focus the acoustical signal toward the intended receiving transducer in pacemaker 100. When multiple pacemakers 100 or other therapy delivery devices are included, a phased array of transducers included in transducer 36 may be controlled by drive signal circuit 34 to pulse the transducers in a programmed time relationship to focus the trigger signal on the receiver of an intended therapy delivery device.

Transducer 36 may include multiple transducers having different properties for emitting different frequencies of sound, light or RF signal. The different transducers are selectable by drive circuit 34 to enable transmission of different frequencies of trigger signals. For example, different frequencies or different patterns of amplitude, frequency, pulse number, etc. may be emitted for triggering different responses by pacemaker 100 or for triggering different intracardiac pacemakers when multiple pacemakers are implanted. As indicated above, different trigger signals may be used to cause pacemaker 100 to deliver pacing pulses according to different pacing pulse control parameters, such as different pulse shape, pulse amplitude, pulse width, pulse rate or pulse number.

The transducer 36 is configured to emit a trigger signal at an amplitude and frequency that is detectable by a receiving transducer of pacemaker 100, after attenuation by body tissues along the pathway between the transducer 36 and the pacemaker 100. In one example, transducer 36 is configured to emit sounds in the range of approximately 40 kHz to over 1 MHz. An optical trigger signal may be emitted with a wavelength greater than approximately 1000 nm. An RF signal can be radiated from an antenna at frequencies between 400 MHz and 3 GHz. The frequency of the trigger signal is selected in part based on the types and thicknesses of body tissues encountered along the signal pathway.

Timing circuit 92 may generate control signal 95 to trigger pacemaker 100 to provide bradycardia pacing, anti-tachycardia pacing, cardiac resynchronization therapy, AV nodal stimulation, or other pacing therapies according to pacing algorithms and timing intervals stored in memory 82. Bradycardia pacing may be delivered by pacemaker 100 temporarily to maintain cardiac output after delivery of a cardioversion-defibrillation shock by ICD 14 as the heart recovers back to normal function post-shock.

Cardiac signal analyzer 90 includes a tachyarrhythmia detector 94 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 (Greenhut, et al.), hereby incorporated herein by reference in its entirety. The timing of R-wave sense event signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized ECG signals to cardiac signal analyzer 90 for use in detecting tachyarrhythmia. Examples of ICDs that may be adapted for use with a triggered pacemaker 100 and operations that may be performed by tachyarrhythmia detector 94 for detecting, discriminating and treating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316 (Gillberg et al.), U.S. Pat. No. 5,545,186 (Olson, et al.), and U.S. Pat. No. 5,855,593 (Olson, et al.), all of which patents are incorporated herein by reference in their entirety.

The detection algorithms are highly sensitive and specific for the presence or absence of life threatening VT and VF. Therapy delivery module 84 includes a HV therapy delivery module including one or more HV output capacitors. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using coil electrode 24 and housing electrode 15.

It should be noted that implemented arrhythmia detection algorithms may utilize not only ECG signal analysis methods but may also utilize supplemental sensors 96, such as tissue color, tissue oxygenation, respiration, patient activity, heart sounds, and the like, for contributing to a decision by processing and control module 80 to apply or withhold a therapy. Sensors 96 may also be used in determining the need and timing for pacing by pacemaker 100. For example, an activity sensor signal or other rate responsive sensor signal, such as a minute ventilation signal, may be used for determining a pacing rate meeting a patient's metabolic demand. Timing circuit 92 produces a control signal 95 to cause emitting device 18 to generate trigger signals that cause pacemaker 100 to deliver pacing pulses at an appropriate rate based on the rate responsive signal. Sensors 96 may include one or more sensors carried by a lead extending from ICD 14 or within or along housing 15 and/or connector block 13.

Telemetry module 88 includes a transceiver and antenna for communicating with another device, such as an external programmer 40 and emitting device 18 when it is configured to receive control signal 95 wirelessly. Under the control of control module 80, telemetry module 88 may receive downlink telemetry from and send uplink telemetry to programmer 40 or another external device. Telemetry module 88 may transmit a control signal wirelessly to emitting device 18, e.g., as an RF signal.

Figure 5:
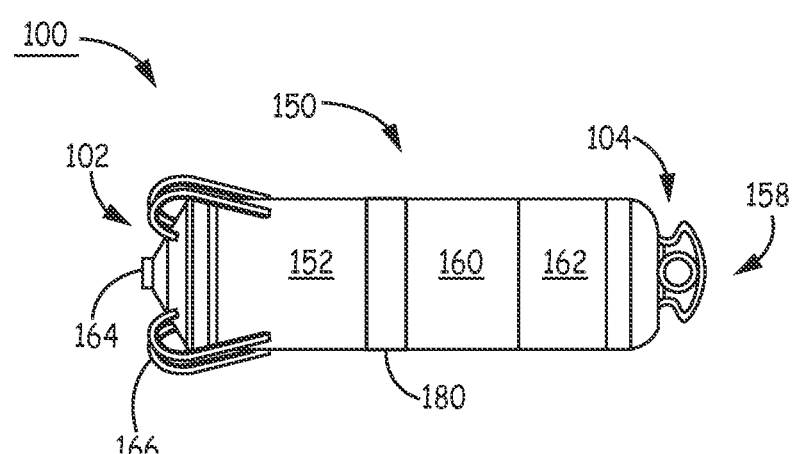
FIG. 5 is a conceptual diagram of a triggered pacemaker.

FIG. 5 is a conceptual diagram of pacemaker 100. Pacemaker 100 includes electrodes 162 and 164 spaced apart along the housing 150 of pacemaker 100. Electrode 164 is shown as a tip electrode extending from a distal end 102 of pacemaker 100, and electrode 162 is shown as a ring electrode along a mid-portion of housing 150, for example adjacent proximal end 104. In alternative embodiments, pacemaker 100 may include two or more ring electrodes or other types of electrodes exposed along pacemaker housing 150 for delivering electrical stimulation to heart 26. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

The housing 150 includes a control electronics subassembly 152, which houses the electronics for producing stimulation pulses and performing therapy delivery functions of pacemaker 100. As one example, control electronics subassembly 152 may include a pulse generator and a receiving transducer for receiving the trigger signal from emitting device 18 and triggering the pulse generator to deliver a pacing pulse via pacing tip electrode 164 and return anode electrode 162 in response to the trigger signal.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety. Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150. Electrodes 162 and 164 form an anode and cathode pair for bipolar cardiac pacing.

Pacemaker 100 may include a set of active fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. In some embodiments, electrodes 162 and 164 are also used for sensing cardiac EGM signals, in which case control electronics subassembly 152 includes sensing circuitry. Numerous types of active and/or passive fixation members may be employed for anchoring or stabilizing pacemaker 100 in an implant position. Pacemaker 100 may include a set of active fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 is located at the proximal end of pacemaker 100 and is configured to connect to a delivery device, such as a catheter, used to position pacemaker 100 at an implant location during an implantation procedure, for example within a heart chamber.

Pacemaker 100 includes a coupling member 180 for coupling a trigger signal from emitting device 18 to a receiving transducer enclosed within housing 150. For example, coupling member 180 may be an acoustic coupling member for transferring sound waves to an acoustic receiving transducer (not shown) enclosed within housing 150 along an inner surface of coupling member 180. In another example, coupling member 180 may be a transparent window for transferring light emitted by emitting device 18 to an optical receiving transducer enclosed within housing 150 along an inner surface of member 180.

When pacemaker 100 is advanced transvenously into a heart chamber, the final orientation of pacemaker 100 may vary. The final orientation of coupling member 180 relative to the patient's anatomy, and therefore the final orientation relative to emitting device 18 may be unknown. Furthermore, the orientation of coupling member 180 relative to the emitting device 18 may fluctuate over time due to shifting of either pacemaker 100 or emitting device 18 or due to cardiac motion, respiratory motion, or other body motion. As such, coupling member 180 may be a continuous member circumscribing housing 150 to receive a trigger signal from multiple sides of pacemaker 100. In other embodiments coupling member 180 may be discontinuous and include multiple segmented members along the circumference of housing 150. It is contemplated that numerous configurations for one or more coupling members along distal end 102, proximal end 104 and/or along the outer circumference of housing 150 may be conceived.

Figure 6:
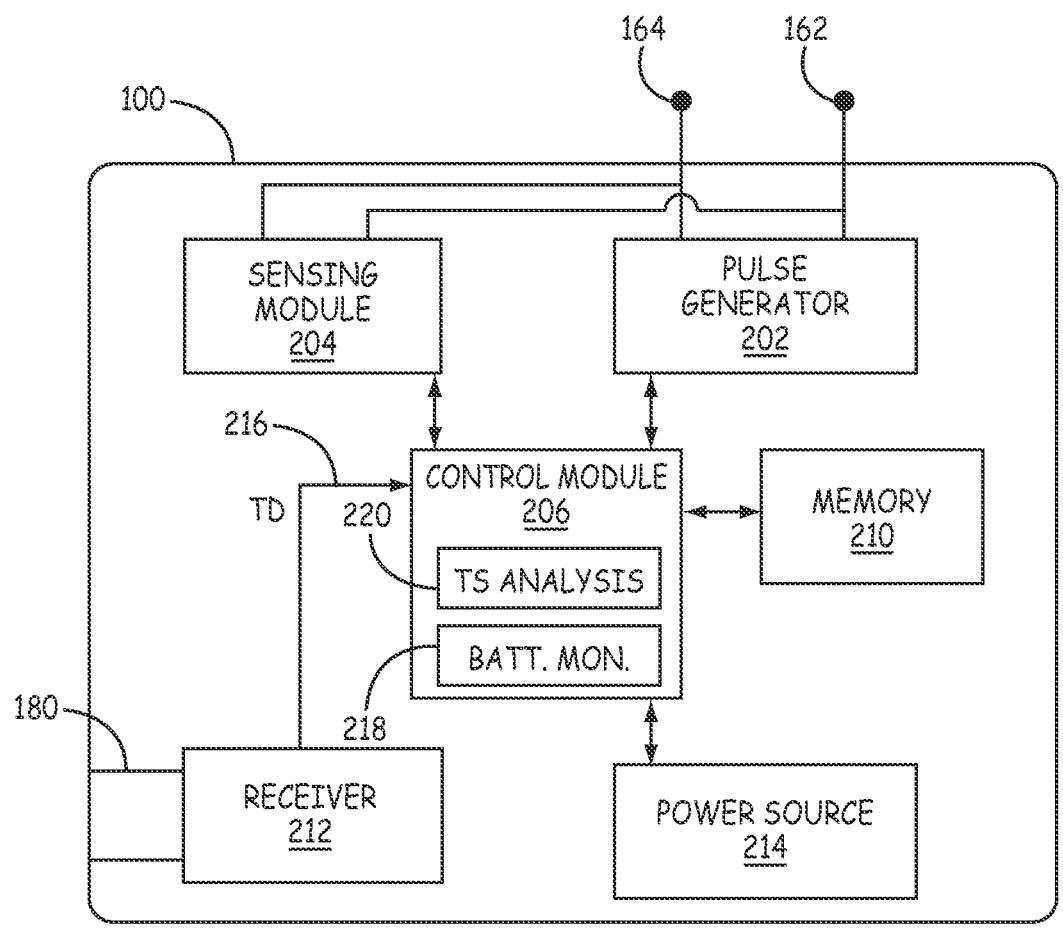
FIG. 6 is a functional block diagram of a triggered pacemaker according to one example.

FIG. 6 is a functional block diagram of an example configuration of pacemaker 100. Pacemaker 100 includes a pulse generator 202, an optional sensing module 204, a control module 206, memory 210, trigger signal receiver 212 and a power source 214. Pulse generator 202 generates electrical stimulation pulses that are delivered to heart tissue via electrodes 162 and 164. Control module 206 controls pulse generator 202 to deliver a stimulation pulse in response to receiving a trigger detect (TD) signal 216 from receiver 212. In other embodiments, pulse generator 202 may be configured to be enabled to deliver a stimulation pulse directly by an input signal received from receiver 212. For example, a switch responsive to a trigger detect signal 216 produced by receiver 212 may enable pulse generator 202 to deliver a stimulation pulse to a targeted tissue via electrodes 162 and 164.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from receiver 212. Upon detecting the trigger signal, the capacitor is coupled to pacing electrodes 162, 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in pacemaker 100 for charging a pacing capacitor to a predetermined pacing pulse amplitude under the control of control module 206 and delivering a pacing pulse.

Alternatively, pulse generator 202 may include a switch that connects power source 214 to pacing electrodes 162 and 164 to deliver the pacing pulse. The switch is opened by trigger detect signal 216 or by a control signal from control module 206, and power source 214 delivers energy to pulse generator 202 for generating a pacing pulse.

As described below, control module 206 may determine a pacing pulse control parameter from the trigger detect signal 216 and use the determined pacing pulse control parameter to control pulse generator 202 to deliver one or more pacing pulses in accordance with the determined control parameter. For example, the pulse width or other aspect of the trigger signal may be determined by control module 206 and used to set the pulse width (or another aspect) of the pacing pulse.

Receiver 212 receives trigger signals through coupling member 180. Receiver 212 includes one or more receiving transducers, which may be mounted directly along an inner surface of coupling member 180, e.g., for receiving sound waves or light. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal 216 is passed to control module 206, or directly to pulse generator 202, to cause pacing pulse delivery.

The receiver 212 is configured to detect only the emitting device-generated trigger signal in some embodiments. For example, receiver 212 may be "tuned" to detect an acoustical or optical signal of a particular signal frequency or bandwidth that is outside a normal physiological range of acoustical or optical signal sensing. In some examples, receiver 212 is not configured to sense and process any physiological acoustical signals or optical signals for determining a physiological event, condition or state.

Control module 206 controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving a trigger detect signal 216, either directly from receiver 212 or via control module 206. Alternatively, the pacing pulse may be delivered after a predetermined time delay.

In some examples, pacemaker 100 is solely a therapy delivery device without sensing capabilities. In other examples, pacemaker 100 may include a sensing module 204 coupled to electrodes 162 and 164 for sensing near-field EGM signals for use in controlling the delivery of pacing pulses. For example, when pacemaker 100 is implanted in the LV, R-waves in the LV may be sensed by sensing module 204. Sensing module 204 generates an R-wave sense event signal that is provided to control module 206. Control module 206 may start a pacing timing interval upon receiving a trigger detect signal 216 from receiver 212. If an R-wave sense event signal is received by control module 206 from sensing module 204 prior to the pacing timing interval expiring, the scheduled pacing pulse is inhibited. No pacing pulse is delivered by pulse generator 202. If the pacing timing interval expires prior to receiving an R-wave sense event signal from sensing module 204, control module 206 enables pulse generator 202 to deliver the scheduled pacing pulse at the expiration of the pacing timing interval.

The pacing timing interval may be, for example, a VV interval to control delivery of a pacing pulse to the LV (or RV) relative to an intrinsic R-wave sensed by ICD 14. The pacing timing interval may be an AV interval to control delivery of a pacing pulse in a ventricle relative to an intrinsic P-wave sensed by ICD 14. The pacing timing interval may be relative to a pacing pulse that is delivered in another heart chamber that may also be delivered by another leadless intracardiac pacemaker that is triggered to deliver a pacing pulse by a trigger signal from emitting device 18. For example, ICD 14 may control emitting device 18 to produce a trigger signal. Two different pacemakers implanted in two different heart chambers may detect the trigger signal. One pacemaker implanted in one heart chamber may deliver a pacing pulse first, immediately upon detecting the trigger signal. The other pacemaker implanted in a different heart chamber may start a pacing time interval upon detecting the trigger signal. The pacemaker in the second heart chamber delivers a pacing pulse second, upon expiration of the pacing timing interval as long as the sensing module 204 does not produce an intrinsic sensed event signal prior to the expiration of the pacing timing interval. The second pacemaker delivers the second pacing pulse at a desired delay after the first pacing pulse. In this way, ICD 14 may control multiple intracardiac pacemakers to delivery pacing pulses in timed coordination with each other using a common trigger signal or using separate, time-delayed trigger signals.

Receiver 212 may include multiple receiving transducers for sensing the trigger signal. The voltage signal produced by multiple transducers may be summed, for example, for comparison to a trigger signal detection threshold. In some embodiments, multiple receiving transducers may be included that are responsive to different frequency bandwidths. Providing detection of different signal frequencies may enable different trigger signals to be transmitted for causing pacemaker 100 to perform different pacing functions and/or improve trigger signal detection.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries.

Control module 206 may also be configured to perform diagnostic testing of pacemaker 100, which may include monitoring the remaining charge of power source 214 and providing a replacement or end-of-life indicator. Control module 206 is shown to include a battery monitoring module 218 for monitoring power source 214. When a remaining battery voltage of power source 214 reaches a threshold level, control module 206 is configured to adjust a parameter of the pacing pulses delivered by pulse generator 202 as described below in conjunction with FIG. 17. The connections between power source 214 and other pacemaker modules and components are not shown in FIG. 6 for the sake of clarity.

In some examples, control module 206 includes a trigger signal (TS) analysis module 220 for analyzing a detected trigger signal to determine pacing pulse parameter information included in the trigger signal. The trigger detect signal 216 may be a logic signal that is set high whenever a receiver transducer voltage signal exceeds a trigger detect threshold. The TS analysis module 220 may analyze the width, number of pulses, and/or time intervals between trigger signal pulses to determine a pacing pulse control parameter from the trigger signal. Control module 206 controls pulse generator 202 to deliver pacing pulse according to the determined pacing pulse control parameter. Examples of trigger signals that include pacing pulse control information are described below, for example in conjunction with FIGS. 11-15.

Circuitry represented by the block diagram shown in FIG. 6 may include any discrete and/or integrated electronic circuit components that implement analog and/or digital circuits capable of producing the functions attributed to pacemaker 100 herein. The functions attributed to pacemaker 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of pacemaker 100 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal received by receiver 212.

In one embodiment, pacemaker 100 includes only receiver 212, pulse generator 202 including low voltage charging circuitry and a pacing capacitor, power source 214 and control module 206, which may be implemented as a logic circuit for controlling pacing pulse delivery in response to trigger signal detection. The pacemaker 100 in this example is minimized in size and functionality and does not include sensing module 204 for receiving physiological signals and does not include an RF transceiver or amplifier included in standard bi-directional telemetry circuitry.

Figure 7:
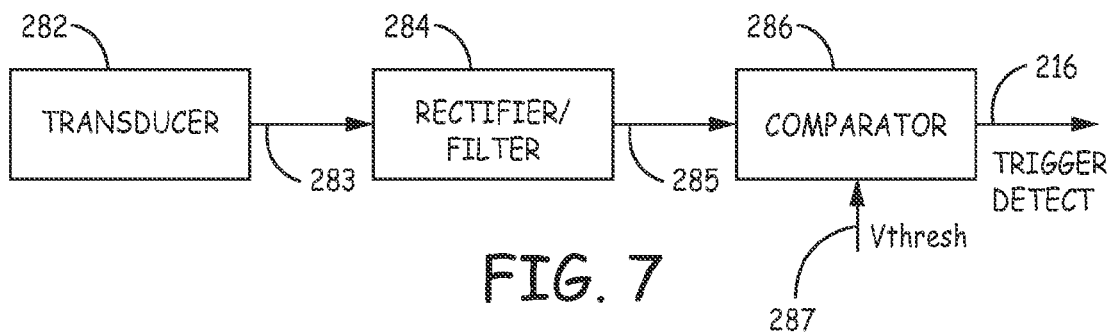
FIG. 7 is a block diagram of one example of a receiver included in a triggered pacemaker for detecting trigger signals.

FIG. 7 is a block diagram of one example of receiver 212 of pacemaker 100. A receiving transducer 282, which may include one or more of the transducers listed above or an RF antenna, produces a voltage output signal 283 when subjected to a trigger signal emitted by emitting device 18. Receiving transducer 282 may have a relatively narrow or wide bandwidth characterized by a center frequency or wavelength that approximately matches the center frequency or wavelength of the transmitting transducer included in the trigger signal emitting device 18.

A rectifier and filter circuit 284 receives the voltage output signal 283 and produces a rectified and filtered signal 285 correlated to the trigger signal converted to an electrical signal by transducer 282. The rectified and filtered signal 285 is provided as input to comparator 286. Comparator 286 receives a detection threshold signal Vthresh 287, e.g., from power source 214, that is compared to rectified and filtered signal 285. When signal 285 exceeds Vthresh 287, a trigger detect signal 216 is produced and passed to the pacemaker control module 206 for triggering pacing pulse delivery. In some examples, trigger detect signal 216 is solely a trigger signal that causes pacing pulse delivery.

In other examples, trigger detect signal 216 includes pacing pulse control parameter information, in which case control module 206 analyzes the trigger detect signal 216 to determine a pacing control parameter. The trigger detect signal 216 output from receiver 212 may be a logic signal that is high as long as the filtered rectified signal 285 is greater than Vthresh 287. The characteristics of pulses included in trigger detect signal 216, such as pulse number, pulse width, interpulse interval, etc., may be interpreted by TS analysis module 220 of pacemaker 100 for setting pacing pulse parameters and controlling pacing pulse delivery by pulse generator 202.

Figure 8:
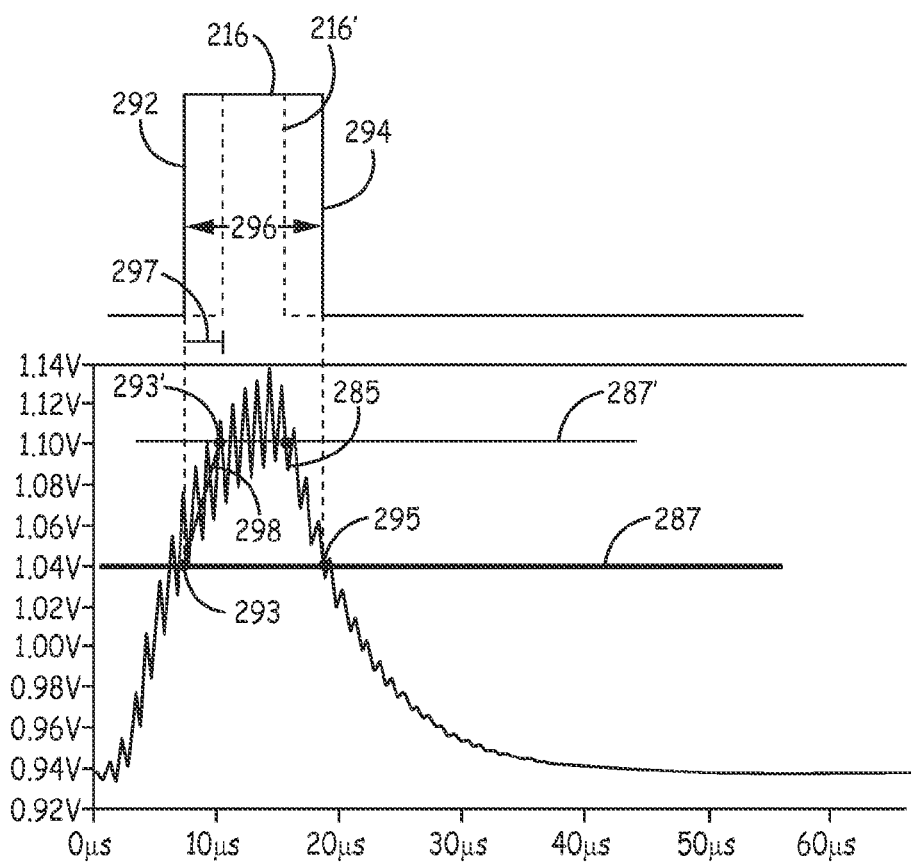
FIG. 8 is a plot of a rectified and filtered voltage signal provided to a comparator for detecting a trigger signal.

FIG. 8 is a plot of a rectified and filtered voltage signal 285 provided to comparator 286 of the receiver 212 shown in FIG. 7. As long as the rectified filtered signal 285 is greater than Vthresh 287, the comparator 286 passes a trigger detect signal 216 to the pacemaker control module 206. The leading edge 292 of trigger detect signal 216 starts upon the rising crossing 293 of Vthresh 287 by signal 285. The trailing edge 294 of trigger detect signal 216 occurs upon the falling crossing 295 of Vthresh 287 by signal 285. The trigger detect signal 216 has a width (time duration) 296 equal to the time that the rectified filtered voltage signal 285 is greater than Vthresh 287. Control module 206 may determine this signal width 296 and set a pacing pulse control parameter, such as pacing pulse width, in response to the signal width 296 in some examples. In other examples, as described below, control module 206 may control the onset and/or offset of a pacing pulse upon receiving trigger detect signal 216 without determining the signal width 296. In still other examples, the control module may count a number of trigger detect signals 216 for use in selecting a pacing pulse control parameter and controlling pacing pulse delivery.

In another embodiment, a second threshold 287' in addition to Vthresh 287 may be added to determine a time interval 297 between a first threshold crossing 293 and a second threshold crossing 293'. The second threshold crossing 293' may be detected by implementing a second comparator in comparator 286 of receiver 212 to produce a second trigger detect output signal 216'. The time interval 297 between two different threshold crossings 293 and 293' is determined by TS analysis module 220 of pacemaker 100 to determine a rising and/or falling slope 298 of trigger signal 285. The determined slope 298 may be used to validate a detected trigger signal 285, distinguish between mutually exclusive trigger signals intended for different therapy delivery devices when multiple therapy delivery devices are implanted, and/or indicated a pacing pulse parameter setting encoded in the trigger signal 285.

Figure 9:
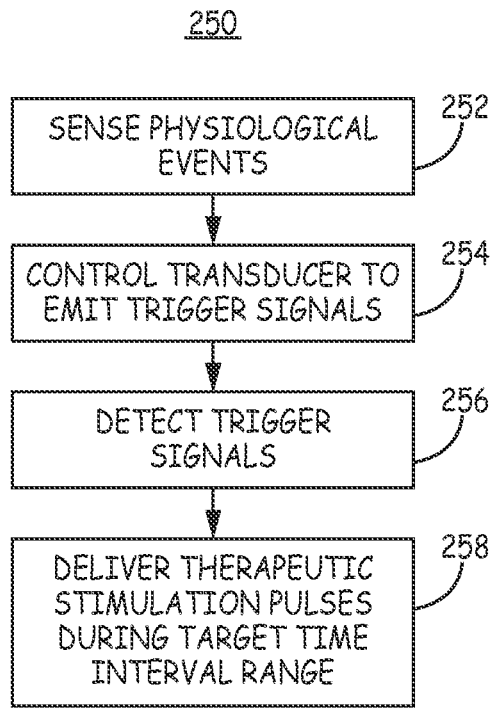
FIG. 9 is a flow chart of a method for controlling therapeutic stimulation pulses delivered by an implantable medical device system.

FIG. 9 is a flow chart 250 of a method for controlling therapeutic stimulation pulses delivered by an implantable medical device system, such as system 2, 10, 10', 10" or 11 shown in FIGS. 1 through 3C. Flow chart 250 and other flow charts presented herein are intended to illustrate the functional operation of the system, and should not be construed as reflective of a specific form of software or hardware necessary to practice the methods described. It is believed that the particular form of software, hardware and/or firmware will be determined primarily by the particular system architecture employed in the sensing device 4 and the therapy delivery device 6 and by the particular sensing and therapy delivery methodologies employed by the system 2. Providing software, hardware, and/or firmware to accomplish the described functionality in the context of any modern pacemaker system, given the disclosure herein, is within the abilities of one of skill in the art. Methods described in conjunction with flow charts presented herein may be implemented in a computer-readable medium that includes instructions for causing a programmable processor to carry out the methods described. The instructions may be implemented as one or more software modules, which may be executed by themselves or in combination with other software.

At block 252, and with reference to system 2 of FIG. 1, a sensing device 4, senses physiological events that are used to coordinate therapeutic stimulation pulses. The physiological events may be R-waves or P-waves sensed from an ECG signal. At block 254, the sensing device 4 controls emitting device 5 to emit trigger signals 7 by applying a drive signal to an emitting device transducer. The trigger signals are detected by therapy delivery device 6 at block 256, which may be a pacemaker such as pacemaker 100. The therapy delivery device 6 delivers therapeutic stimulation pulses in response to detecting the trigger signal 7. The trigger signal 7 is emitted at time intervals that cause the therapeutic stimulation pulses to be delivered at block 258 within a range of a target time interval relative to the sensed physiological events. For example, a ventricular pacing pulse may be delivered by therapy delivery device 6 within a range of a target AV delay following a P-wave sensed by sensing device 4.

One trigger signal 7 may be delivered following each sensed event to coordinate a therapeutic stimulation pulse with each sensed event, e.g., one ventricular pacing pulse for each P-wave sensed event. The trigger signal 7 is emitted at a time interval relative to the sensed physiological event to cause the therapy delivery device 6 to deliver the therapeutic stimulation pulse within a range of a targeted time interval from the sensed physiological event. In other words, the trigger signals emitted by emitting device 5 and therapeutic stimulation pulses have a 1:1 correspondence.

The trigger signals emitted over a time interval including two or more sensed physiological events may have a total combined time duration that is equal to the total combined time duration of the associated triggered therapeutic stimulation pulses. In other words, for each trigger signal, one pacing pulse may be delivered and the trigger signal and the pacing pulse may have the same signal width. However, since trigger signal emission may require significant battery consumption, in other examples the total combined time duration of the trigger signals is less than the total combined time duration of the therapeutic pulses invoked by the trigger signals. The trigger signals may be emitted at a rate that is less than the rate of the therapeutic stimulation pulses. The trigger signals may be emitted at a signal width that is less than the pulse width of the therapeutic stimulation pulses. In some examples, the trigger signals are emitted at a rate and signal width that is less than the rate and pulse width of the therapeutic stimulation pulses. In other words, in some examples the trigger signals may have less than a 1:1 correspondence with the therapeutic stimulation pulses in duration and/or number (rate). For example, one trigger signal may trigger therapy delivery device 6 to deliver a series of therapeutic stimulation pulses so that a trigger signal is not delivered every time a stimulation pulse is delivered. To illustrate, one trigger signal may be emitted by emitting device 5 in response to a P-wave sensed by sensing device 4, causing therapy delivery device 6 to deliver a series of 2, 4, 6, 8 or other number of pacing pulses at a fixed rate in response to the one trigger signal.

In another example, the trigger signal may have a pulse duration that is less than a stimulation pulse duration (width). Therapeutic stimulation pulses may be delivered by therapy delivery device 6 in a 1:1 correspondence with detected trigger signals 7, but trigger signals 7 may be emitted with a shorter signal width than the pulse width of the stimulation pulses. Battery energy is saved by using techniques that reduce the total combined time of the trigger signals compared to the total combined time of the therapeutic stimulation pulses.

Figure 10:
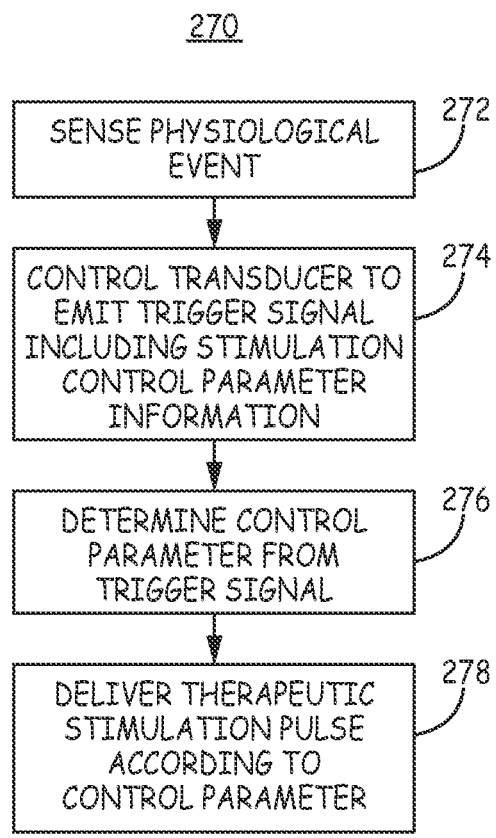
FIG. 10 is a flow chart of a method for controlling triggered therapeutic stimulation pulses according to another example.

FIG. 10 is a flow chart 270 of a method for controlling triggered therapeutic stimulation pulses according to another example. With reference to system 2 of FIG. 1, a physiological event is sensed by sensing device 4 at block 272. A transducer of emitting device 5 is controlled at block 274 by control signal 3 from sensing device 4 to emit a trigger signal 7 that includes stimulation pulse control parameter information. The therapy delivery device 6 may not include a transceiver for standard RF communication capability that enables bi-directional communication with amplification of a received signal to enable programming of therapy delivery control parameters using an external programmer. As such, the trigger signal 7 may be used to transfer therapy control parameter information to the therapy delivery device (in addition to triggering stimulation pulse timing). Therapy control parameter information may include, without limitation, stimulation pulse amplitude, stimulation pulse width, stimulation pulse train frequency, number of stimulation pulses in a pulse train, or other stimulation pulse characteristics.

At block 276, the therapy delivery device 6 detects the trigger signal 7 and determines the control parameter from the trigger signal 7. The control parameter information is included in the trigger signal 7 by coding the trigger signal pulse width, signal frequency, signal amplitude, pulse number, pulse interval, or other aspect of the trigger signal 7 that is detectable by the therapy delivery device 7, e.g., as determined by TS analysis module 220 shown in FIG. 6.

In response to the trigger signal, the therapy delivery device 6 delivers one or more therapeutic stimulation pulses to a targeted tissue at a targeted time interval according to the control parameter determined from the trigger signal 7. The stimulation pulse is delivered immediately or after a predetermined time delay after detecting trigger signal 7 such that the stimulation pulse is delivered within a targeted time interval range from the physiological event sensed by sensing device 4. The stimulation pulse itself is defined at least in part by the determined control parameter. For example, the pulse width or pulse amplitude may be set based on the determined control parameter coded in the trigger signal 7. In this way, the trigger signal 7 controls both the timing and a feature of the pulse delivered by therapy delivery device 6.

Figure 11:
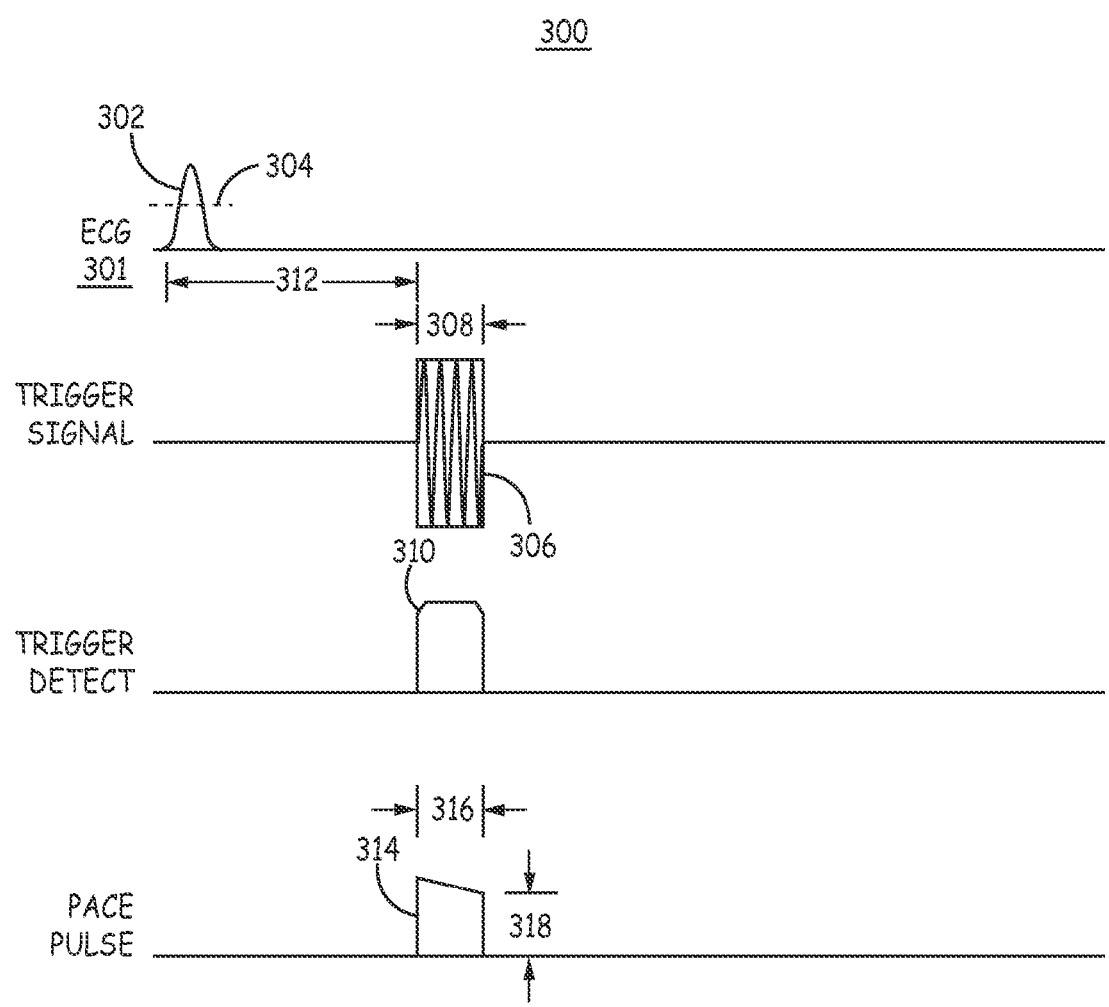
FIG. 11 is a timing diagram of a trigger signal and resulting pacing pulse according to one example.

FIG. 11 is a timing diagram 300 of a trigger signal 306 and resulting pacing pulse 314 according to one example. A sensing device 4 (or ICD 14), monitors an ECG signal 301 for sensing a cardiac event 302, e.g., a P-wave or an R-wave. When the ECG signal 301 crosses a sensing threshold 304, a cardiac event 302 is sensed. Sensed cardiac event 302 is a P-wave in one illustrative example. The sensing device 4 starts a pacing timing interval 312, e.g., an atrioventricular (AV) interval, upon sensing event 302. The pacing timing interval 312 is set based on a desired time interval between the sensed cardiac event 302 and a pacing pulse 314 less any system delay between initiating a trigger signal 306, producing a trigger detect signal 310 and delivering the pacing pulse 314.

At expiration of the pacing timing interval 312, the emitting device 18 is enabled to emit a trigger signal 306 at a predetermined frequency or wavelength for a time duration that defines the trigger signal pulse width 308. A trigger detect signal 310 is produced by a receiver of the therapy delivery device 6, e.g., the pacemaker receiver 212 shown in FIG. 6, for the entire trigger signal width 308 over which the rectified trigger signal 306 exceeds a trigger detection threshold (not illustrated in FIG. 11).

The therapy delivery device 4 starts the therapeutic stimulation pulse 314, which is a pacing pulse in this example, in response to the trigger detect signal 310. For example, a pacing capacitor of pacemaker 100 may be discharged through the pace electrodes 162 and 164 until the rectified trigger signal 306 falls below the trigger signal detection threshold. The pacing pulse 314 may be terminated with the trailing edge of the trigger detect signal 310, i.e., when the rectified trigger signal 306 falls below the trigger detection threshold, by disconnecting the pacing capacitor from the pacing electrodes 162 and 164. The pacing pulse width 316 is equal to the time interval that the trigger detect signal 310 is high, which matches the width 308 of the emitted trigger signal 306. In other examples, the therapy delivery device 6 may be configured to start the leading edge of pacing pulse 314 after a time delay following the onset of trigger detect signal 310 and have a pulse width equal to the width 308 of the trigger signal 306. In the example shown in FIG. 11, there is a 1:1 correspondence between the width 308 of trigger signal 306 and pacing pulse width 316.

The pacing pulse amplitude 318 may be a fixed parameter in some examples. The pacing pulse amplitude may be set at a fixed voltage, for example 1.5 V. Alternatively, the pacing pulse amplitude 318 may set to a fixed fraction of the therapy delivery device battery voltage, for example one half the battery voltage of power source 214 of FIG. 6. The pacing pulse width 316 is controlled by the trigger signal width 308 to deliver a pacing pulse energy that successfully captures the cardiac tissue (or other targeted tissue).

Figure 12:
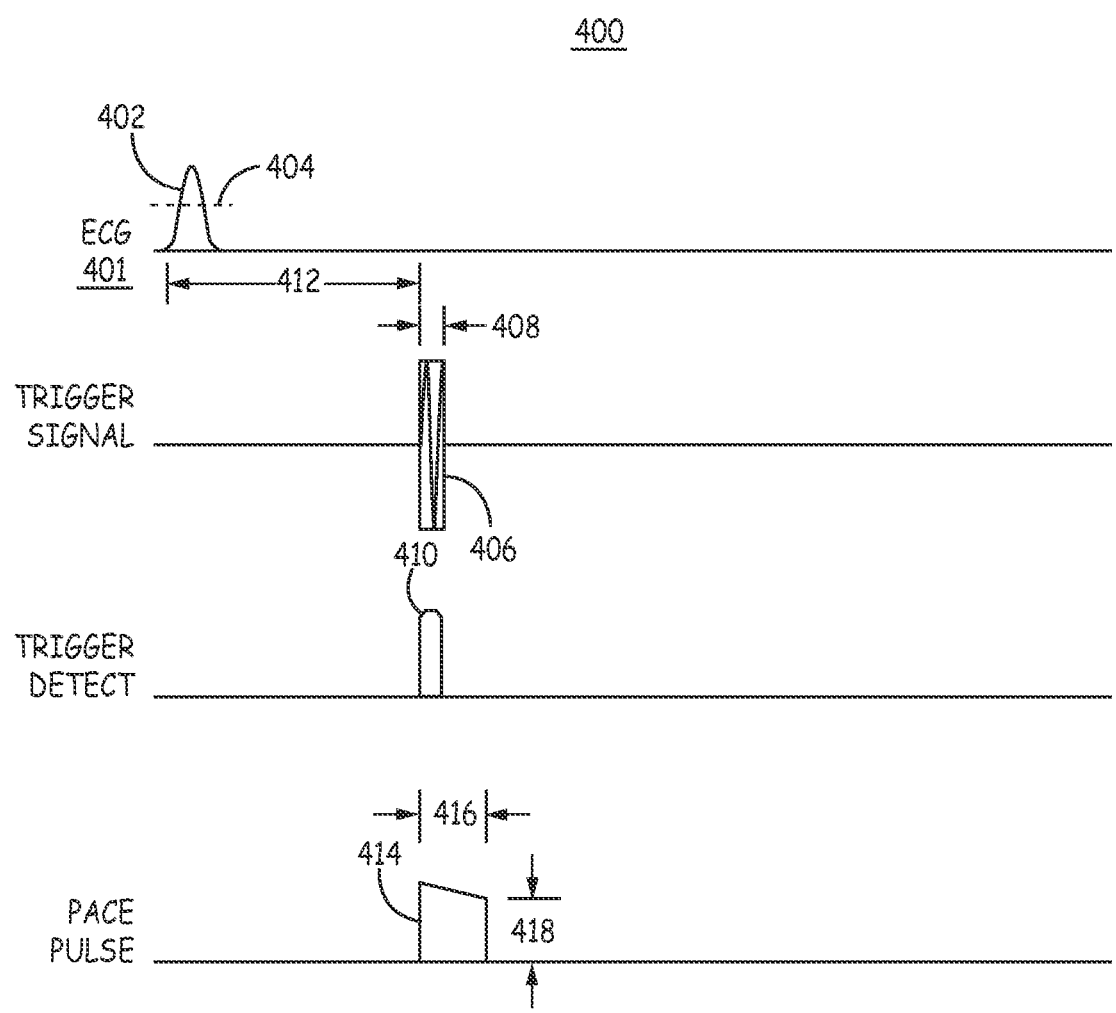
FIG. 12 is a timing diagram of an alternative method for controlling a pacing pulse parameter using a trigger signal.

FIG. 12 is a timing diagram 400 of an alternative method for controlling a pacing pulse parameter using a trigger signal. With reference to system 10 of FIG. 2A, the ECG signal 401 is monitored by ICD 14 to detect a cardiac event 402. In one example, sensed event 402 is a P-wave sensed by ICD 14 based on a sensing threshold 404. One method for sensing a P-wave by ICD 14 is generally disclosed in commonly-assigned U.S. patent application Ser. No. 14/524, 090, filed on Oct. 27, 2014 (Greenhut, et al.), incorporated herein by reference in its entirety. A pacing timing interval 412, which is an AV interval in this example, is started by control module 80 of ICD 14. Upon expiration of the AV interval 412, timing module 92 sends a control signal 95 to the emitting device 18. Emitting device 18 emits a trigger signal 406 at a predefined trigger signal frequency or wavelength for a relatively short signal width 408. Receiver 212 detects the trigger signal 406 and produces a trigger detect signal 410. The trigger detect signal 410 is passed to pacemaker control module 206, as long as the rectified, trigger signal 406 remains above a trigger detection threshold (not illustrated).

The pacemaker trigger signal analysis module 220 determines the trigger signal width 408 based on the duration of the trigger detect signal 410 and controls the pulse generator 202 to deliver pacing pulse 414 with a pulse width 416 that is a multiple of the trigger signal width 408. Trigger signal 406 may be emitted at a rate having a 1:1 ratio with the number of pacing pulses 414 that are delivered by pacemaker 100, but the time that each trigger signal 406 is transmitted, i.e., the signal width 408, is shorter than the pacing pulse width 416 to conserve battery energy supplied to emitting device 18 from ICD 14 and/or conserve a dedicated emitting device battery. Alternatively, the rate of trigger signal 406 may be less than a 1:1 rate with pacing pulses 414 such that for each trigger signal 406, more than one pacing pulse 414 is delivered at a fixed rate.

The pacing pulse amplitude 418 may be fixed as described above. The trigger signal 406 can be controlled by the control signal 3 to be emitted for different, incremental signal widths 408. The width of the detected trigger signal 410 is used by pacemaker 100 to control the pacing pulse width 416 as a fixed multiple of the trigger signal width 408. In this way, the trigger signal width 408 is not required to be equal to the pacing pulse width 416 but the trigger signal 408 contains pacing pulse control parameter information.

To illustrate, a multiple N may be stored as a fixed value, e.g. 8, in pacemaker memory 210. The emitting device 18 is controlled by control signal 95 to emit trigger signal 406 for 0.05 ms, e.g. 50 cycles of a 1 MHz signal frequency. The trigger detect signal 410 is produced by the pacemaker receiver 212 having a width substantially equal to the time that the trigger signal 406 is greater than the trigger detection threshold, e.g., Vthresh 287 as shown in FIG. 10. The pacemaker control module 206 measures the width of the trigger detect signal 410, e.g., using a digital timer or counter included in TS analysis module 220 of control module 206. The control module 206 includes a multiplier for multiplying the trigger detect signal width by the stored multiple N to set the pacing pulse width 416. Control module 206 enables pulse generator 202 to deliver pacing pulse 414 at a fixed pulse amplitude 418 and the determined pulse width 416 of 0.4 ms in this example (0.05 ms multiplied by 8).

Figure 13:
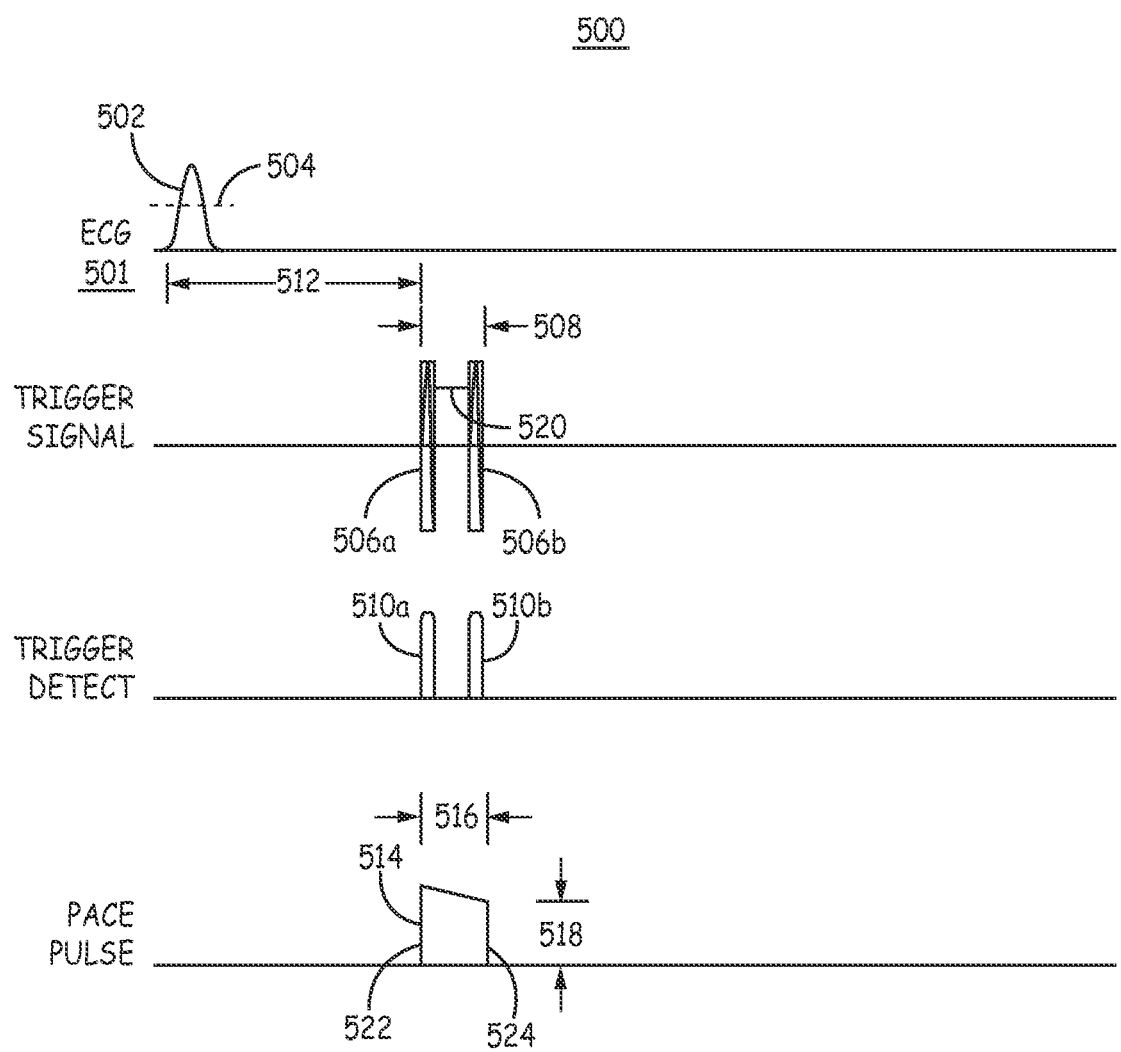
FIG. 13 is a timing diagram illustrating another example method for controlling pacing pulse delivery using trigger signals.

FIG. 13 is a timing diagram 500 illustrating another example method for controlling pacing pulse delivery using trigger signals. A cardiac event 502 is sensed by ICD 14 from the ECG signal 501 based on a sensing threshold 504. ICD 14 starts the pacing timing interval 512 upon sensing event 502, and controls emitting device 18 to transmit a first trigger signal pulse 506a upon expiration of the pacing timing interval 512.

In this example, the trigger signal includes a pair of pulses 506a and 506b, collectively 506. ICD control module 80 sends a first control signal to emitting device 18 to cause emission of the first trigger signal pulse 506a, waits a timed interpulse interval 520, and then sends a second control signal to emitting device 18 to cause emission of the second trigger signal pulse 506b. The total trigger signal width 508 of the trigger signal 506 is defined by the first pulse 506a, the interpulse interval 520, and the second pulse 506b. The duration of each individual pulse 506a and 506b may be minimized to reduce battery consumption required for producing trigger signal pulses 506a and 506b.

The pacemaker receiver 212 produces a pair of trigger detect signals 510a and 510b when the respective trigger signal pulses 506a and 506b are greater than the trigger detection threshold (e.g., Vthresh 287 of FIG. 8). Receiver 212 detects each trigger signal pulse 506a and 506b, spaced apart by inter-pulse interval 520. In response to trigger detect signal 510a, the pulse generator 202 starts pacing pulse 514 by coupling the pacing capacitor to the pace electrodes 162, 164. In some cases, the pacing capacitor of pulse generator 202 is pre-charged. In other cases, pacing capacitor charging is started upon trigger detect signal 510a such that a short system delay between trigger detect signal 510a and pacing pulse 514 may exist.

In response to the second trigger detect signal 510b, the pulse generator 202 uncouples the pacing capacitor from the pace electrodes 162 and 164 to terminate the pacing pulse 514. The pacemaker control module 206 controls pulse generator 202 to deliver pacing pulse 514 with a leading edge 522 coincident with trigger detect pulse 510a and a trailing edge 524 coincident with trigger detect pulse 510b.

In this way, pacing pulse 514 is delivered with a pacing pulse width 516 substantially equal to the trigger signal width 508 without requiring trigger signal emission for the entire duration of signal width 508. The pacing pulse amplitude 518 may be fixed as described previously. The pacing pulse energy delivered to capture the heart is controlled by varying the trigger signal interpulse interval 520, and thereby varying the timing of the second trigger detect signal 510b and coincident trailing edge 524 of pacing pulse 514.

In another example, pacemaker 100 may be configured to measure the interpulse interval 520 by determining the time interval between trigger detect signals 510a and 510b and multiplying the interpulse interval 520 by a fixed value to obtain pacing pulse width 516. The trigger signal pulses 506a and 506b may be delivered at an interpulse interval 520 that is a fraction of the total pacing pulse width 516.

The pulses 506a and 506b may be identical pulses. In other examples, pulse 506b may have at least one pulse characteristic different than pulse 506a to be distinguishable as the terminating pulse 506b and the starting pulse 506a. For example, starting pulse 506a may have a pulse width that is greater than or less than pulse 506b, a frequency that is greater than or less than 506b, or an amplitude that is greater than or less than pulse 506b. In this way, if a terminating pulse 506b is detected without a preceding starting pulse 506a, the pacemaker 100 will not initiate a pacing pulse. Likewise, if a starting pulse 506a is detected but a terminating pulse 506b is not detected within some maximum time interval, the pacing pulse 514 may be automatically truncated as a predefined maximum pulse width.

Figure 14:
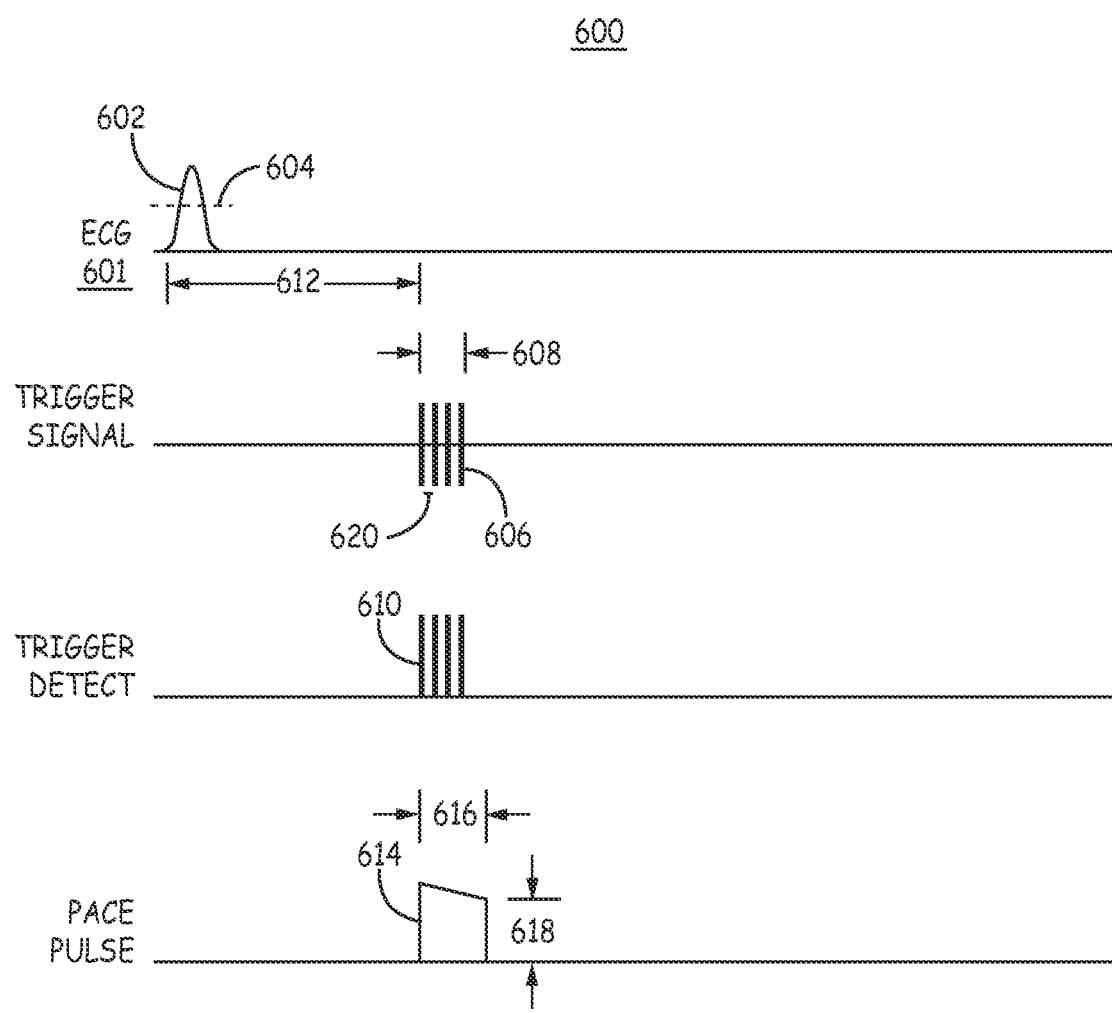
FIG. 14 is a timing diagram of another method for controlling pacing pulses using a trigger signal.

FIG. 14 is a timing diagram 600 of another method for controlling pacing pulses using a trigger signal. The cardiac event 602 is sensed by the ICD 14 when the ECG signal 601 crosses a sensing threshold 604. The pacing timing interval 612 is started by ICD control module 80 upon sensing event 602. Upon expiration of the pacing timing interval 612, ICD 14 sends a control signal 95 to emitting device 18 that causes emitting device 18 to emit a trigger signal 606 having a variable number of pulses. The number of pulses N is set by control signal 95.

The pacemaker receiver 212 detects the trigger signal pulses and produces a trigger detect signal 610 having N pulses equal to the number of pulses in the trigger signal 606 that exceed the trigger detection threshold. The TS analysis module 220 of pacemaker control module 206 counts the number of pulses in the trigger detect signal 610 and multiplies that number by a fixed time interval, e.g. 0.10 ms, stored in memory 208 to determine the pacing pulse width 616.

Control module 206 controls pulse generator 202 to deliver pacing pulse 614 having a fixed pulse amplitude 618 and a variable pulse width 616 set equal to the number of pulses of trigger detect signal 610 multiplied by the time interval stored in memory 208. ICD 14 thereby controls pacing pulse width 616 by controlling how many pulses are emitted by emitting device 18 in each trigger signal 606. The pacing pulse width 616 may be incremented or decremented by the time interval stored in pacemaker memory 208 by increasing or decreasing the number of pulses in the trigger signal 606. In the example, shown four pulses in trigger signal 606 are detected as four pulses in trigger detect signal 608. The pacemaker control module 206 multiples four by a stored time interval, e.g. 0.1 ms, to obtain a pacing pulse width 616 of 0.4 ms.

The pulses in trigger signal 606 are delivered at the trigger signal frequency, (for example 1 MHz) or wavelength (for example 1100 nm) for an individual pulse width that can be minimized to reduce battery consumption. The individual pulse width, however, must be detectable by the pacemaker receiver 212. The interpulse interval 620 is long enough that the individual pulses of trigger signal 606 can be detected by pacemaker receiver 212. The total width 608 of trigger signal 606 defined by the N individual pulses and the interpulse interval 620 is not greater than pacing pulse width 616 and will typically be shorter than the pacing pulse width 616 so that the pacing pulse 614 can be terminated at the correct width 616.

In the example of FIG. 14, the interpulse interval 620 is equal between all pulses of trigger signal 606. The pacemaker control module 206 may wait for at least two interpulse intervals 620 before determining the pacing pulse width so that if one pulse is missed (not detected) the next pulse, occurring at twice the expected trigger signal pulse interval 620 may be counted twice to account for the missed pulse.

In the examples of FIGS. 13 and 14 that require the pacemaker 100 to determine the pacing pulse width from the trigger signal width or the trigger signal pulse number, the onset of the pacing pulse 514, 614 may be set to occur after a delay interval from the onset of the trigger detect signal 506, 606 to allow processing time required to determine the final pacing pulse width. It is understood that an inherent signal processing delay between the time that the ICD 14 sends the control signal 95 to the emitting device 18 and the earliest time that the pacing pulse 514 or 614 can be initiated or terminated may exist. The various timing intervals, such as the pacing timing intervals 512 and 612 and the interpulse intervals 520 and 620 and any pacemaker applied delay time before delivering pacing pulse 514 or 614 will be selected to account for this signal processing delay required to determine a pacing pulse parameter from the trigger detect signal 510 or 610 and still provide accurate timing of pacing pulses 514 and 614 relative to the sensed cardiac event 502 and 602, respectively.

Figure 15:
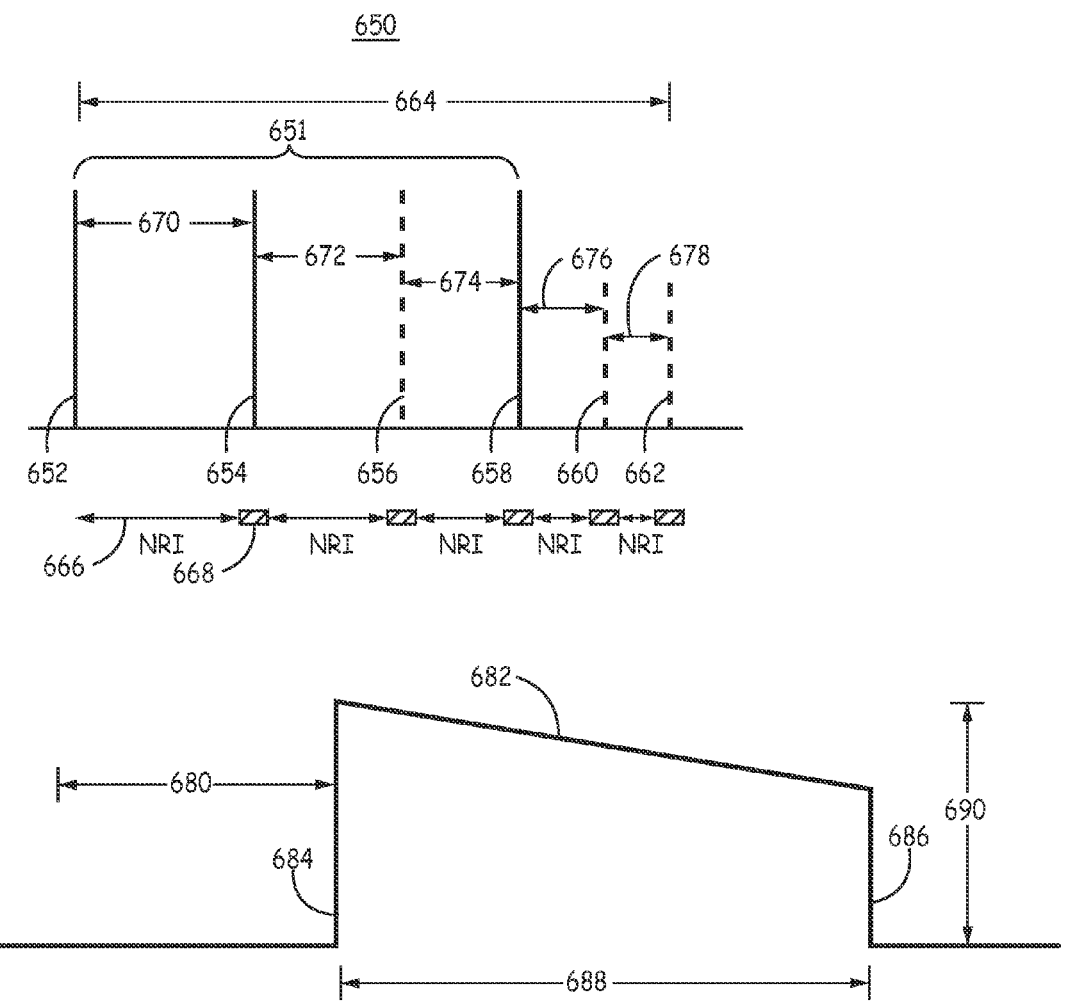
FIG. 15 is a timing diagram of a trigger signal.

FIG. 15 is a timing diagram 650 of a trigger signal 651 that includes a train of four pulses 652, 654, 656 and 658. Each pulse 652, 654, 656 and 658 is delivered at a selected trigger signal frequency or wavelength for an individual pulse duration that is at least a minimum pulse duration detectable by the pacemaker receiver 212. In this example, the interpulse intervals 670, 672 and 674 are different from each other in contrast to the equal interpulse intervals 620 shown in the example of FIG. 14. Predetermined interpulse intervals 670, 672, and 674 that are different from each other can facilitate correct counting of the number of trigger signal pulses 652, 654, 656, and 658 by the pacemaker 100. The interpulse intervals 670, 672 and 674 may decrease by a predetermined decrement between consecutive pulses. Alternatively interpulse intervals may increase or vary bi-directionally between consecutive pulses.

The first pulse 652 and second pulse 654 of trigger signal 651 are separated by an interpulse interval 670, which may correspond to a minimum pacing pulse width or a fraction of the minimum pacing pulse width. Upon detecting the first pulse 652, the pacemaker 100 increments a pulse counter included in trigger signal analysis module 220 and waits for a second pulse 654 at the interval 670. Upon detecting the second pulse 654, the pulse counter is incremented by one to a count of two. The next pulse 656 is expected at the decremented interval 672. If pulse 656 is not detected by pacemaker 100, as indicated by dashed line, the pacemaker 100 may wait for at least one next interpulse interval 674 to determine if any additional trigger signal pulses are detected. If pulse 658 is detected by pacemaker 100 at a combined interval equal to interval 672 plus interval 674, the pacemaker 100 determines that pulse 656 was missed. Pacemaker 100 will increment the pulse counter by two (to a count of four) based on the detected pulse 674 and the determination that pulse 656 was missed. Pacemaker 100 then waits for the next decremented interval 676.

In this example, the trigger signal 651 is four pulses (670 through 674) long. The short dashed lines 660 and 662 represent additional trigger signal pulses that may be present if the trigger signal is more than four pulses long. All six pulses 652 through 662 may represent a maximum number of trigger signal pulses and correspond to a maximum pacing pulse width. If no pulse is detected at interval 676, pacemaker 100 may wait at least one more interval 678 to determine if pulse 660 was missed. If two expected interpulse intervals 676 and 678 expire without detecting any additional pulses, the pacemaker control module 206 counts a total of four pulses, even though pulse 656 was not detected, based on three detected pulses 652, 654 and 658 and the total time of intervals 672 and 674 between detected pulses 654 and 658 that indicates pulse 656 was missed.

The pacemaker control module 206 controls pulse generator 202 to deliver pacing pulse 682, which may have a fixed amplitude 690, with a pulse width 688 determined as a multiple of the number of counted pulses in trigger signal 651. The pacing pulse 682 is terminated at trailing edge 686 based on the determined pulse width 688.

In this example, the leading edge 684 of pulse 682 is started after a delay interval 680 to allow the pacemaker receiver 212 time to receive the first three pulses 652, 654 and 656. If only one pulse 652 is detected after waiting for the second and third pulses 654 and 656, the pacing pulse width can be set to a minimum pulse width (one detected pulse times a fixed time interval stored in memory 210). Thus the delay interval 680 allows pacemaker 100 time to detect at least the first three trigger signal pulses 652, 654 and 656 before determining and setting the pacing pulse width 688.

In other examples, the interpulse intervals 670, 672, 674, 676, and 678 may be short enough that the leading edge 684 of pacing pulse 682 may be started upon detection of the first trigger signal pulse 652, and pacemaker 100 determines the pacing pulse width 688 during pacing pulse 682 by counting the total number of trigger signal pulses and multiplying that number by a fixed interval stored in memory 210. In still other examples, the delay interval 680 may be set to a value that is greater than a maximum trigger signal width 664 to enable pacemaker 100 to detect all pulses up to a maximum number of pulses, six in this example, and determine the pacing pulse width 688 prior to starting pacing pulse 682.

Additionally, the pacemaker signal receiver 212 may apply noise rejection intervals (NRIs) 666 during the interpulse intervals 670 through 678. NRIs 666 are time intervals during which a detected signal pulse is rejected as noise. The preceding signal pulse detected outside the NRI 666 may also be rejected as an invalid pulse. For example, if signal pulse 652 is detected, the pacemaker signal receiver may start a NRI 666. If another signal pulse is detected during NRI 666, it is rejected as noise and the signal pulse 652 that caused the NRI 666 to be started is also rejected as noise and not part of a valid trigger signal. The next time a signal pulse is detected, a new NRI 666 is started.

If no signal pulse is detected during the NRI 666, a detection interval 668 is started upon the expiration of the NRI 666. The detection interval 668 is a short time interval that starts at or just prior to the end of the interpulse interval 670, which may be stored in pacemaker memory 210. A signal pulse 654 detected during the detection interval 668, along with the prior detected signal pulse 652 without any intervening pulses detected during the NRI 666 is evidence of a valid trigger signal. Subsequent NRIs 666 are started following each detected trigger signal pulse (or each detection interval 668 in case of a missed pulse, e.g., pulse 656). Any signal pulse detected during any of the NRIs 666 will cause any previously detected pulses during detection intervals 668 to be determined as noise and not counted as trigger signal pulses and will not lead to the detection of a valid trigger signal.

As shown in FIG. 15, the NRIs may decrease in duration as the interpulse intervals 670 through 678 decrease in duration. Each NRI 666 may be a portion or percentage of a known interpulse interval. Each detection interval 668 may be a multiple of the width of each trigger signal pulse 652 through 662. A trigger signal pulse detected during any of the NRIs 666 may cause rejection of all detected pulses, including those detected during a detection interval 668. Pulses detected during the detection intervals 668, when no pulses are detected during any of the NRIs 666, are counted and lead to the detection of a valid trigger signal by pacemaker 100.

The pacemaker 100 may count the number of trigger signal pulses of a valid trigger signal 651 for multiplying by a stored factor to determine the pacing pulse width 688 as described above. Alternatively, the pacemaker 100 may count the number of trigger signal pulses of a valid trigger signal 651 to cause an adjustment of a previously delivered pacing pulse parameter, such as pulse width. For example, if the maximum possible number of pulses in a valid trigger signal 651 is four, detection of a trigger signal having exactly two pulses may cause the pacemaker 100 to deliver a pacing pulse 682 at the same pulse parameter as a previous pulse, e.g., the same pulse width 688. If exactly three trigger signal pulses are counted, the pacemaker 100 may increase the pacing pulse parameter by a stored increment, e.g., increase pacing pulse width by 100 µs. If all four possible trigger signal pulses are counted in a valid trigger signal 651, the pacemaker 100 may decrease a pacing pulse parameter by a stored decrement, e.g., decrease pacing pulse width 682 by 100 µs.

Figure 16:
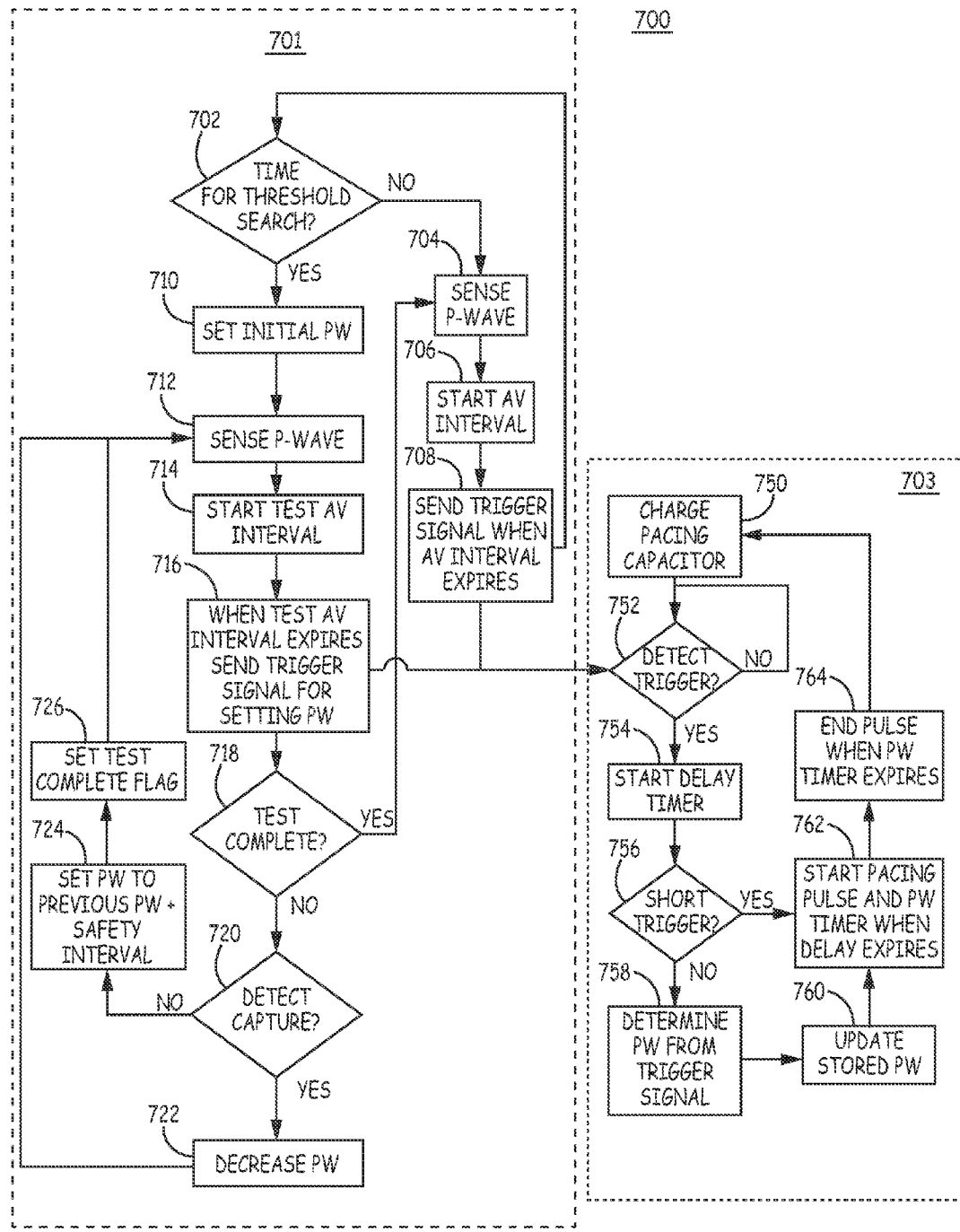
FIG. 16 is a flow chart of a method for setting a pacing pulse width by performing a pacing threshold search in a triggered pacemaker system according to one example.

FIG. 16 is a flow chart 700 of a method for setting a pacing pulse width by performing a pacing threshold search in a triggered pacemaker system, such as system 2, 10, 10', 10" or 11, according to one example. Decisions and blocks shown in dashed box 701 represent operations performed by the sensing device that is producing a control signal passed to the emitting device. In the examples described herein, box 701 represents functions performed by ICD 14 and emitting device 18. Decisions and steps shown in dotted box 703 represent operations performed by the therapy delivery device that is detecting the trigger signal and delivering therapeutic stimulation pulses. In the illustrative example, box 703 represents functions performed by pacemaker 100.

In one example, the threshold search is performed according to flow chart 700 for determining the capture threshold of the LV. In this example, the LV is paced by pacemaker 100 at a target AV interval following a P-wave for delivering CRT. It is recognized, however, that the methods of the threshold search can be applied to other pacing or electrical stimulation therapy applications. The particular cardiac events sensed by the sensing device for starting a pacing timing interval may be atrial or ventricular, paced or sensed events, for example. The pacing timing interval started upon a cardiac event may correspond to an AV interval, a VV interval or a VA interval. The targeted tissue receiving the pacing pulse or electrical stimulation therapy may be any cardiac or neural tissue. Further, it is recognized that the threshold search and method for controlling the pacing pulse width as generally described in conjunction with FIG. 16 may be adapted to other non-cardiac therapies, such as stimulation of the phrenic nerve or other therapies which require capture of a targeted muscle or nerve.

At decision block 702, the ICD 14 determines if it is time to perform a threshold search. A threshold search may be performed at a scheduled time of day, in response to a user command, or in response to a change in a physiological signal that the ICD 14 is monitoring that may indicate that loss of capture has occurred. If it is time for a threshold search, the ICD 14 enters a threshold search mode of operation by advancing to block 710, where an initial test pulse width (PW) is set. In the examples described herein, pacing pulse amplitude is fixed and the PW is adjusted to achieve capture of the targeted tissue, e.g., the LV myocardium. The initial PW may be set to a maximum PW or a PW previously known to cause capture. The threshold search is performed to determine a minimum PW that achieves capture of the LV when the pacing pulse amplitude is set to a fixed value.

At block 712, the ICD 14 senses a P-wave and starts a test AV interval at block 714. The test AV interval may be a shortened AV interval compared to an AV interval used during normal LV pacing. A shortened AV interval may be used during the threshold search to promote pacing pulse delivery earlier than an intrinsically conducted depolarization to the LV to avoid false capture detection due to an intrinsic depolarization arriving ahead of, or simultaneously with, a pacing-induced depolarization. To illustrate, the AV interval may be set to 80 ms for delivering LV pacing during CRT. The AV interval may be shortened to 50 ms during a threshold search.

When the test AV interval expires, the ICD 14 sends a control signal 95 to the emitting device 18 at block 716 to cause the emitting device 18 to send a trigger signal that includes PW information. The trigger signal may have a signal width equal to the PW set at block 710 as described in conjunction with FIG. 11, include a starting and terminating pulse that indicate the time of the leading and trailing edges of the pacing pulse as described in conjunction with FIG. 13, or have a signal width or number of pulses that are used by the pacemaker 100 to determine the initial pacing pulse width as described in conjunction with FIGS. 12, 14 and 15.

Now referring to pacemaker operations 701, the pacemaker receiver 212 detects the trigger signal at block 752. The pacemaker 100 may charge the pacing capacitor at block 750 while waiting to receive the trigger signal. Upon receiving the trigger signal, a delay timer is started at block 754. A delay time may be set by the pacemaker between a trigger detect signal produced by the pacemaker receiver 212 and delivery of the triggered pacing pulse, e.g., delay time 680 shown in FIG. 15. The delay timer is optional or may be set to zero during the threshold search.

The trigger detect signal may be analyzed by TS analysis module 220 of control module 206 to determine if the trigger signal is a threshold search trigger signal or a therapy trigger signal. For example, at block 756, the pacemaker 100 determines if the trigger signal is shorter than a threshold signal width used to discriminate between a therapy pace trigger signal and a threshold search trigger signal. A therapy pace trigger signal may be set a minimum duration that is reliably detectable by the pacemaker. The detected trigger signal may be determined to be a "short" trigger signal at block 756 by determining the width of the trigger detect signal produced by the pacemaker receiver 212 and comparing the trigger detect signal width to a threshold width. If the detected trigger signal is less than the threshold width, the trigger signal is a therapy trigger signal not a threshold search trigger signal. If the trigger detect signal width is greater than the threshold width, the trigger signal is a threshold search trigger signal and includes information used by the pacemaker 100 to set the pacing PW to a test PW for determining capture.

In response to detecting a threshold search trigger signal at block 756, the pacemaker 100 determines the pacing PW from the detected trigger signal at block 758. As discussed above, the threshold search trigger signal may be controlled to include PW information according to any of the methods described in conjunction with FIGS. 11 through 15.

A previously-used pacing PW stored by the pacemaker 100 is updated at block 760 as the PW determined at block 758 from the threshold search trigger signal. At block 762, upon expiration of the delay timer if set, a pacing pulse is started by coupling a stored charge to pacing electrodes 162 and 164, and a PW timer is started. The PW timer is set to the PW stored at block 760. When the PW timer expires, the pacing pulse is terminated at block 764. The pacing capacitor is recharged at block 750 while the pacemaker 100 waits for the next trigger signal.

Meanwhile, referring again to ICD operation 701, the ICD 14 monitors the ECG signal at block 720 to determine if capture of the LV occurred after sending the trigger signal at block 716. Capture may be detected by the ICD 14 based on sensing an R-wave by sensing module 86 at the test AV interval or based on detection of a paced R-wave morphology different than an intrinsic R-wave morphology by cardiac signal analyzer 90 or a combination thereof.

If capture is detected at block 720, the pacing PW is decreased at block 722. The process returns to block 712, to sense a P-wave and start another test AV interval at block 714. When the test AV interval expires, the emitting device 18 is controlled to send a trigger signal for setting a new, decreased pacing PW at block 716. The pacemaker 100 receives the trigger signal and detects it as a threshold search trigger signal at block 756 as described above. The pacemaker 100 determines the new, decreased PW by analysis of the trigger signal at block 758 (e.g., analysis of the trigger signal width or pulse number as described above), updates the previously stored PW at block 760, and delivers a pacing pulse at the new PW at blocks 762 and 764.

This process continues until the ICD 14 does not detect capture at block 720. Failure to detect capture indicates that the currently stored PW in the pacemaker 100 is less than the capture threshold. The PW needs to be reset to a suprathreshold interval. At block 724, the PW is set to the previous PW that did result in capture plus a nominal safety interval, e.g. 0.10 ms. The previous PW that did result in capture is determined as the capture threshold PW. The pacing PW for therapy delivery is set to the capture threshold PW plus a safety margin interval to reduce the likelihood of loss of capture due to small fluctuations in the capture threshold.

At block 726, a test complete flag is set indicating that the threshold search is complete. At the next sensed P-wave (block 712), the test AV interval is started again (block 714) and the trigger signal is sent at block 716 for setting the PW at the threshold PW plus the safety margin. With the test complete flag set, as determined at block 718, the ICD 14 now transitions into a therapy delivery mode of operation by advancing to block 704 to wait for the next P-wave.

Meanwhile the pacemaker 100 receives the final threshold search trigger signal that is setting the PW to the threshold PW plus the safety margin. At block 752, the trigger signal setting the threshold PW plus the safety margin is detected by pacemaker 100. A delay timer is optionally started at block 754, and the trigger signal is detected as a threshold search trigger signal at block 756 for use in setting a PW. The PW is determined from the trigger signal at block 758. At block 760, the PW stored in pacemaker memory 210 is updated to the PW determined from this final threshold search trigger signal, i.e., the threshold PW plus the safety margin. A pacing pulse is delivered at the updated stored PW at block 762 and 764. The ICD 14 may monitor the ECG signal to verify that capture occurred in response to this pacing pulse delivered at the updated PW.

Now operating in a therapy delivery mode, the ICD 14 starts the AV interval at block 706 after sensing a P-wave at block 704. In the therapy delivery mode, the AV interval is set at block 706 to an optimal interval for promoting synchrony between the heart chambers. When the AV interval expires, the ICD 14 controls the emitting device 18 to emit a short therapy trigger signal at block 708. The therapy trigger signal is delivered for a minimum duration (signal width) that is reliably detectable by the pacemaker and does not include pacing PW information.

At block 752, the pacemaker 100 detects the trigger signal and starts the optional delay timer at block 754. At block 756, the pacemaker control module 206 compares the duration of the trigger detect signal 216 produced by the receiver 212 to a threshold search interval. If the trigger detect signal 216 is determined to be a "short" trigger, i.e., less than a threshold search interval, the trigger signal is recognized as a pacing therapy trigger signal and not a threshold search trigger signal. The pacemaker 100 does not determine a PW from the trigger signal. The pacing pulse is started at block 762, and a PW timer is started using the stored PW, which was last updated based on the threshold PW determined during the previous threshold search.

Upon expiration of the PW timer, the pacing pulse is terminated at block 764. The pacing capacitor is recharged at block 750. The system continues to operate in the pacing therapy mode (blocks 704 through 708 for the ICD 14 and blocks 750 through 756, 762 and 764 for the pacemaker 100) until it is time for the next threshold search. During the pacing therapy mode, minimal energy is used to generate the trigger signal, and the pacing pulses are delivered with the PW that is stored in pacemaker memory 210 without determining a PW from the trigger signal on a beat-by-beat basis. The trigger signal is transmitted with PW information only during the threshold search mode (blocks 710 through 726 for the ICD). Otherwise the trigger signal is a timing signal only, without PW information, for the pacemaker 100 to use for delivering the pacing pulse at the therapeutic AV interval.

Figure 17:
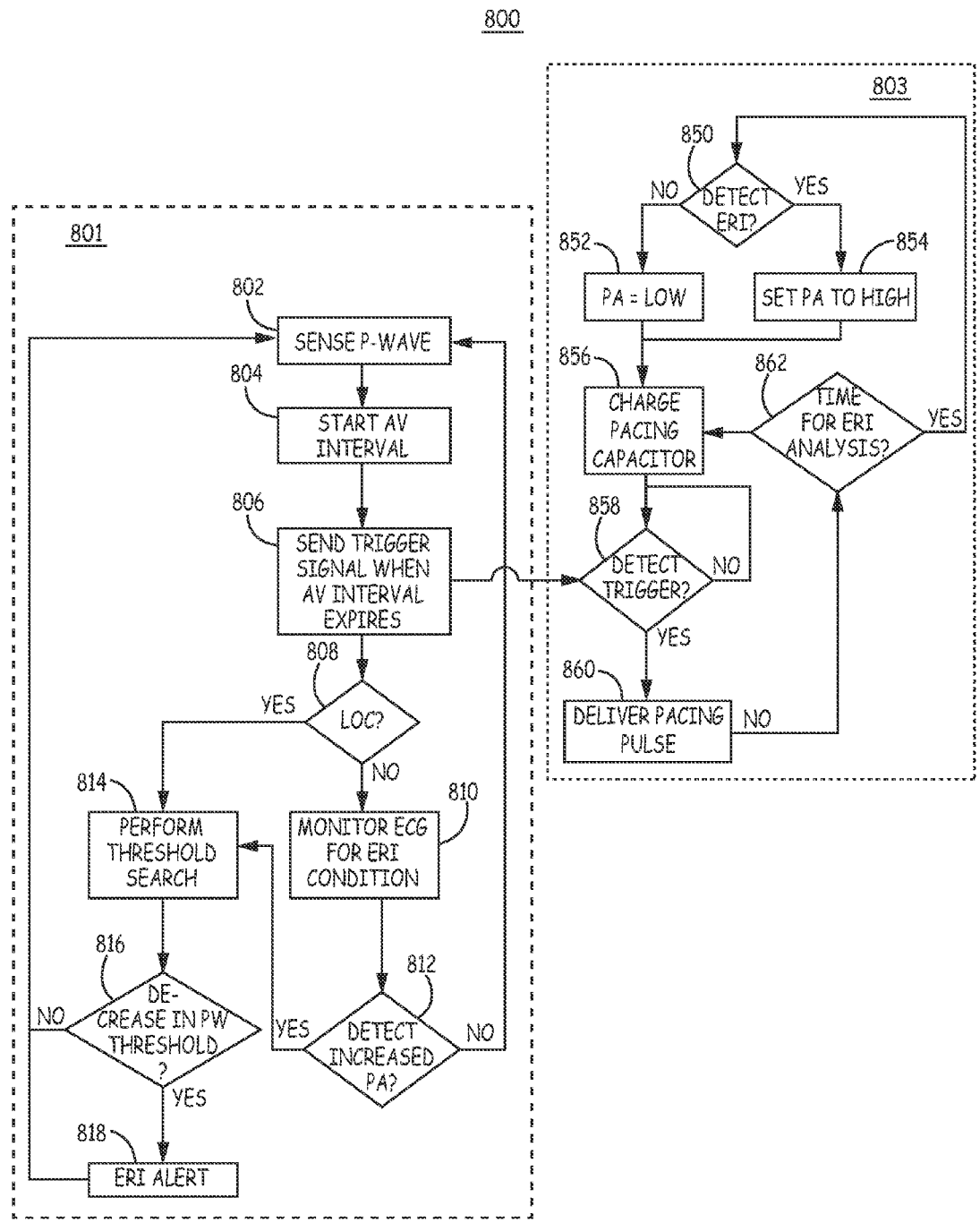
FIG. 17 is a flow chart of a method for providing a pacemaker battery alert signal when the pacemaker battery reaches a threshold voltage level.

FIG. 17 is a flow chart 800 of a method for providing a pacemaker battery alert signal when the pacemaker battery reaches a threshold voltage level. For example, an elective replacement indicator (ERI) alert signal may be generated by ICD 14 when the pacemaker battery voltage (of power source 214) falls below a predetermined level. An ERI is a flag set by pacemaker 100 when the pacemaker battery voltage falls below the predetermined level. An ERI alert signal generated by ICD 14 notifies the patient and/or clinician that pacemaker replacement is recommended to avoid the pacemaker battery reaching end of life, causing a disruption in the patient's therapy. Since pacemaker 100 may not have wireless RF telemetry capability for transmitting an ERI alert to an external programmer or other device, ICD 14 may be configured to detect an ERI condition of pacemaker 100 and transmit the ERI alert signal to an external device via telemetry module 88 to notify a clinician and/or patient of the ERI condition.

In flow chart 800, operations and decisions enclosed by dotted-line 803 represent functions performed by pacemaker 100. Operations and decisions shown enclosed by dashed line 801 represent functions performed by ICD 14. Beginning with the pacemaker operations 803, the pacemaker control module 206 determines if an ERI condition is detected at block 850. Pacemaker control module 206 includes a battery monitor 218 for detecting a battery voltage of power source 214 that is less than an ERI voltage threshold. For example, the battery monitor 218 may include a comparator for comparing the battery voltage to a predetermined ERI threshold. The ERI threshold may be a fixed value or may be based on a pacing history (e.g., frequency and PW) and an estimation of remaining battery life based on the pacing history. Reference is made to commonly-assigned U.S. Pat. No. 5,402,070 (Markowitz, et al.) and U.S. Pat. No. 6,016,448 (Busacker, et al.) for descriptions of ERI determinations, both of which patents are incorporated herein by reference in their entirety.

As long as an ERI condition is not detected at block 850, the pacing pulse amplitude (PA) remains at a fixed, initial setting that is referred to as a "LOW" setting at block 852 because it is lower than the PA that will be used when an ERI condition is detected. The fixed LOW setting may be a fixed percentage of the battery voltage, e.g., 50% of the battery voltage. Alternatively, the PA may be set at a fixed voltage, e.g. 1.5 V.

The pacemaker 100 charges the pacing capacitor between pacing pulses at block 856 and discharges the capacitor in response to detecting a trigger signal at block 858 to deliver a pacing pulse at block 860. The pacing pulse is delivered after an optional delay interval, using the LOW PA, and either a stored PW or a new PW determined from the trigger signal as described in conjunction with FIG. 16.

After delivering the pacing pulse, the pacemaker control module 206 determines if it is time to check the battery voltage at block 862 to detect an ERI condition. If not, the pulse generator 202 begins charging the capacitor(s) at block 856 to the LOW PA.

If it is time to check the battery voltage, the control module 206 performs an ERI analysis to detect an ERI condition at block 850. If an ERI condition is detected, i.e., if the battery voltage falls below an ERI voltage, the PA is set to a HIGH setting at block 854. The "HIGH" setting is a setting that is greater than the initial fixed PA setting used prior to the ERI condition. For example, the "HIGH" setting may be a fixed voltage that is greater than the LOW setting, e.g. 2.0 V. Alternatively, the HIGH setting may be an increased percentage of the battery voltage, e.g. 100% of the remaining battery voltage.

The pulse generator 202 charges the pacing capacitor(s) to the HIGH PA voltage at block 856, and pacemaker 100 continues to deliver pacing pulses in response to detected trigger signals at blocks 858 and 860 according to the methods described above. When the pacing PA is set to a HIGH setting, and the PW remains the same, the pacemaker 100 delivers pacing pulses that are highly likely to continue capturing the heart. The next time a pacing PW capture threshold search is performed, as described in conjunction with FIG. 16, the PW capture threshold will be lower due to the HIGH PA. The PW will be adjusted to the shorter PW capture threshold to avoid excessive battery drain. By increasing the PA from the LOW to the HIGH setting, however, the ICD 14 is able to detect the ERI condition and issue a pacemaker ERI alert as described next.

Now referring to ICD operations 801, the ICD 14 monitors the ECG for sensing P-waves at block 802 and starts an AV interval at block 804 in response to a sensed P-wave. At block 806, the ICD 14 controls the emitting device 18 to send a trigger signal upon expiration of the AV interval.

After sending the control signal 95 to cause trigger signal transmission, the ICD 14 may monitor the ECG signal for a loss of pacing capture (LOC) as indicated at decision block

808. LOC monitoring may be performed on every paced beat, hourly, daily, or other scheduled interval.

LOC may be detected by analyzing the ECG signal. For example, if an R-wave is not detected within an expected time interval from sending the trigger signal or after detecting the pacing pulse signal on the ECG signal, LOC may be detected. Additionally or alternatively, morphology analysis of the R-wave sensed after the trigger signal may be performed to detect an R-wave morphology that corresponds to an intrinsically conducted depolarization instead of a pacing-induced R-wave, i.e., an evoked response.

If LOC is detected, a pacing PW threshold search may be performed at block 814 to detect an increase in PW threshold. The PW stored in the pacemaker 100 is adjusted as needed based on the pacing threshold search results by sending a trigger signal containing PW information as described previously in conjunction with FIG. 16.

If LOC is not detected, the ICD 14 is configured to monitor the ECG signal at block 810 to detect a possible ERI condition of pacemaker 100. The ECG signal may be monitored for an ERI condition on a scheduled basis, for example every 24 hours or another time interval. One possible ERI condition is an increase in the pacing pulse signal amplitude present on the monitored ECG signal due to an increase in the pacing PA to the HIGH PA setting by pacemaker 100. The ICD 14 may measure the amplitude of the pacing pulse signal on the ECG signal and compare the amplitude to a previously measured amplitude, averaged amplitude, or predefined amplitude threshold. The ICD 14 can set a time window for measuring the pacing pulse signal amplitude on the ECG signal since the ICD 14 controls the timing of the pacing pulse via the trigger signal.

If a threshold increase in the pacing pulse signal amplitude on the ECG signal is detected by the ICD 14 at block 812, the pacemaker 100 may have reached an ERI condition that caused the pacemaker 100 to increase the pacing PA to the HIGH setting. The ICD 14 may advance to block 814 to perform a pacing PW threshold search as described in conjunction with FIG. 16.

If the PW capture threshold has decreased by a threshold amount compared to one or more most recently determined PW threshold(s), as determined at decision block 816, a pacemaker ERI condition is confirmed at block 818. If the pacing PA has been increased by the pacemaker 100, the PW required to achieve capture will be decreased. The increased pacing PA determined from the ECG signal (at block 812) and/or the decreased PW capture threshold (determined at block 816) provide evidence that the pacemaker 100 has changed the pacing PA due to an ERI condition. A pacemaker ERI alert signal is generated by the ICD 14 at block 818, which is transmitted by the ICD RF telemetry communication module 88 to an external device 40, such as a programmer or home monitor.

Alternatively, the ICD 14 may generate an ERI alert signal at block 818 directly in response to detecting an increase in PA at block 812 without verifying the ERI condition by performing a threshold search. The ICD 14 may be configured to detect an ERI condition by detecting a predetermined minimum number of consecutive pacing pulses on the ECG signal each having a threshold change in the pacing pulse signal amplitude compared to a previously measured pacing pulse signal amplitude. For example, if the ICD detects three consecutive pacing pulses on the ECG signal each having a signal amplitude that is 50% (or another percentage) greater than the pacing pulse signal amplitude measured on the previous day, an ERI condition is detected.

In other examples, each time a pacing threshold search is performed, the PW capture threshold may be compared to a previously determined PW capture threshold. A sudden drop in PW capture threshold is unexpected and may indicate a PA increase by the pacemaker due to an ERI condition. For example, without limitation, if a decrease in PW capture threshold of more than 25% since the previous pacing threshold search has occurred, a sudden drop in PW capture threshold is detected. If a sudden drop in PW capture threshold is detected, the pacemaker ERI alert is produced at block 818 without necessarily detecting the pacing pulse PA at block 812.

Figure 18:
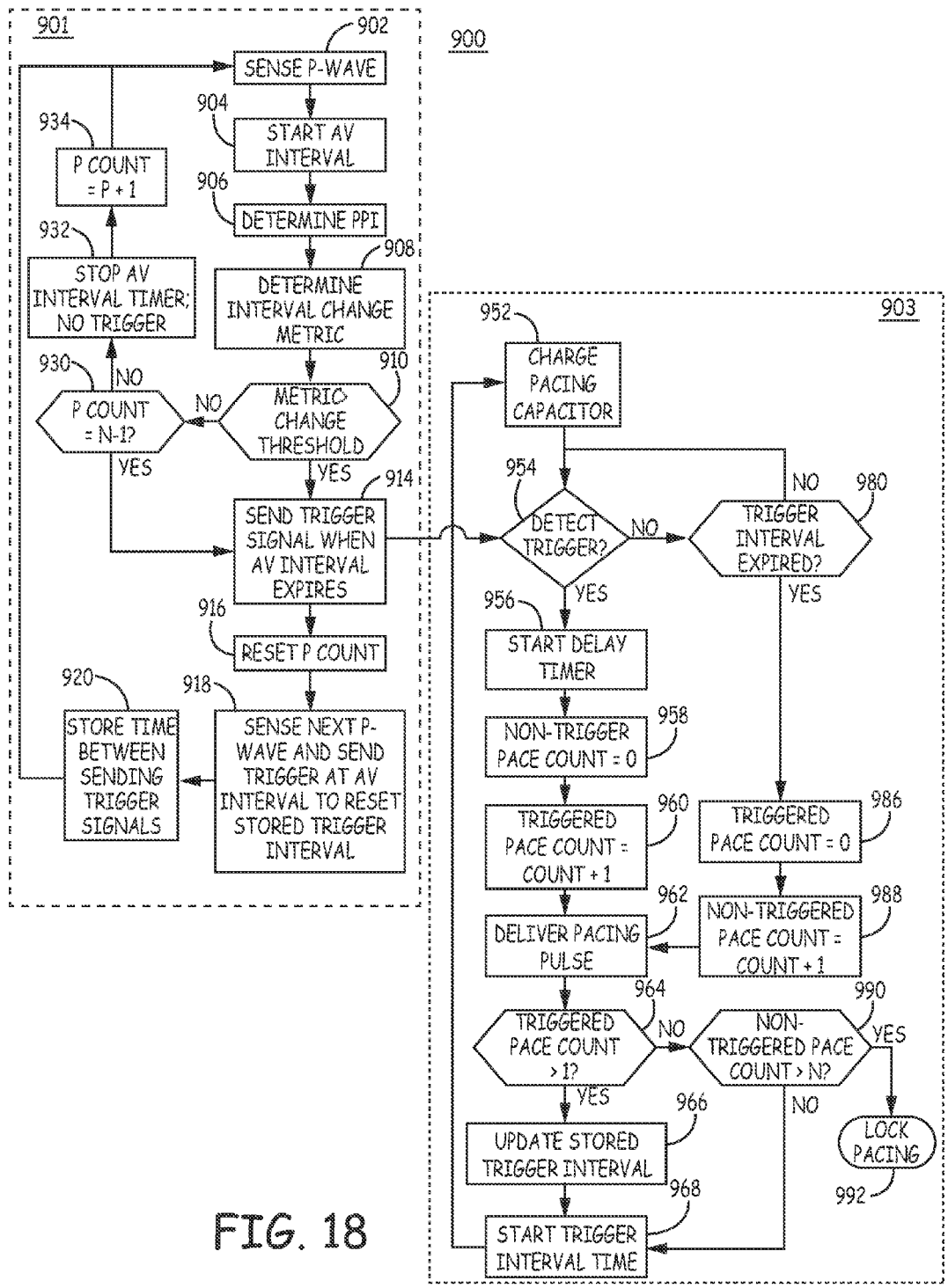
FIG. 18 is a flow chart of a method for controlling a triggered pacemaker using less than a 1:1 rate ratio of trigger signals to pacing pulses.

FIG. 18 is a flow chart 900 of a method for controlling a triggered pacemaker using less than a 1:1 rate ratio of trigger signals to pacing pulses. In some applications, a stimulation pulse may be synchronized to frequently sensed events, which would require frequent trigger signals and significant power consumption by the emitting device. For example, in CRT, an LV pacing pulse is delivered on every cardiac cycle, e.g., after every sensed P-wave, in order to improve ventricular synchrony. In order to reduce power consumption for triggering an intracardiac pacemaker on every cardiac cycle, more than one pacing pulse may be delivered in response to one trigger signal resulting in a ratio of trigger signals to pacing pulses that is less than a 1:1 ratio. In other words the trigger signal rate is less than the rate of delivered pacing pulses over the same interval of time.

In flow chart 900, the operations in dashed box 901 represent functionality of the ICD 14 (or other sensing device). Operations shown in dotted box 903 represent functionality of the pacemaker 100. The methods described in conjunction with flow chart 900 may be implemented during periods of time that the patient's heart rate is expected to remain relatively steady, for example during sleep or during low levels of activity. As such, the techniques for controlling pacing using fewer trigger signals than delivered pacing pulses may be enabled during particular times of day, in response to a patient activity signal and/or posture signal, or other indication that the heart rate is likely to remain relatively stable.

At block 902, the ICD senses a P-wave. The AV interval timer is started at block 904 in response to sensing the P-wave. A PP interval (PPI) is determined at block 906 as the interval of time between the sensed P-wave and the immediately preceding sensed P-wave. The PPI is used in determining an interval change metric at block 908. When the heart rate (HR) is stable, the pacemaker 100 may deliver pacing pulses at a repeated, fixed interval of time without requiring a new trigger signal. For example, if the HR is 60 bpm (equivalent to a stable 1000 ms PPI), two consecutive trigger signals delivered at an 80 ms AV interval from each of two consecutively sensed P-waves will be delivered 1000 ms apart. The pacemaker 100 may determine the time interval between two consecutive trigger signals and store this as a trigger interval for automatically delivering a series of pacing pulses at the trigger interval in response to the two trigger signals. If no new trigger signal is detected before the stored trigger interval expires, the pacemaker 100 may automatically deliver a pacing pulse at the stored trigger signal interval, which is 1000 ms in the current example. As long as the HR remains steady at 60 bpm, the LV pacing pulses delivered spaced apart in time by the trigger interval will be delivered at the targeted AV interval during each cardiac cycle without requiring a trigger signal during each cardiac cycle.

If the HR changes, however, a stored trigger signal interval may result in an actual AV interval to be unacceptably different than the targeted AV interval. As HR changes, therefore, a new trigger signal needs to be sent by the emitting device 18 to correct the pacemaker timing and cause the LV pacing pulse to be delivered at the target AV interval or within an acceptable range of the AV interval.

Accordingly, after sensing the P-wave at block 902 and measuring the current PPI at block 906, the ICD 14 assesses one or more recently measured PPIs. The ICD 14 determines if a change in the PPI is leading to unacceptable timing of the pacing pulse. An actual AV interval between the sensed P-wave and an imminent pacing pulse that will be delivered by the pacemaker 100 at a stored trigger interval may be outside an acceptable range of the target AV interval.

At block 908, the ICD 14 determines an interval change metric (ICM) using the current PPI. The ICM may be a difference between the current PPI and one or more previous PPIs, an accumulated (summed) difference between consecutive PPIs, a trend of PPI differences, or other index computed from the measured PPI and one or more preceding PPIs. It is recognized that in alternative embodiments, the ICD 14 may determine RR intervals and determine an interval change metric from the RR intervals.

The ICM is compared to a change threshold at block 910. If the ICM is greater than a change threshold, LV pacing at the trigger interval presently stored in the pacemaker 100 will result in a pacing pulse delivered at an actual AV interval unacceptably different than the targeted AV interval. If the ICM is greater than the change threshold, therefore, the ICD 14 controls the emitting device 18 to send a trigger signal at block 914 upon expiration of the AV interval. In some examples, the AV interval timer may be started after determining that a trigger signal is needed based upon the ICM. For example, when the ICM exceeds the change threshold, an AV interval timer may be started on the next sensed P-wave to produce a trigger signal on the next cardiac cycle.

A counter P is reset to zero at block 916 after sending a trigger signal. The counter P is used to count the number of P-waves that are sensed without sending a trigger signal. As described below, the pacemaker 100 may include a lockout safety feature that limits the number of pacing pulses delivered at a stored trigger interval without receiving a trigger signal. Pacing pulses delivered at a stored trigger interval when a trigger signal is not detected are referred to as "non-triggered" pacing pulses. If a maximum number of non-triggered pacing pulses are delivered, the pacemaker 100 stops delivering pacing pulses until a new trigger signal is detected. Non-triggered pacing pulses are therefore counted by the pacemaker 100, and the ICD 14 counts sensed P-waves for which no trigger is sent to track the number of non-triggered pacing pulses. The P counter that is reset at block 916 is therefore a counter that tracks the number of times that the pacemaker 100 has likely delivered a non-triggered pacing pulse using a stored trigger interval but no trigger signal was sent by the emitting device 18. Since a trigger signal is sent at block 914, any count stored by the P counter is cleared and reset to zero.

At block 918, the ICD controls the emitting device to send at least one more trigger signal following the next consecutive P-wave in order to deliver at least two consecutive trigger signals (at blocks 914 and 918) that are used by the pacemaker 100 to update the stored trigger interval. Two consecutive trigger signals sent at an AV interval following two consecutive sensed P-waves establish a trigger interval that matches the HR of the current cardiac cycle. This single pair of trigger signals may be used by the pacemaker 100 to update the stored trigger interval.

Alternatively, the ICD 14 may deliver trigger signals at AV intervals following more than two consecutively sensed P-waves such that two or more consecutive trigger intervals are determined by the pacemaker 100 to establish a new trigger interval matching the patient's current heart rate and storing an updated trigger interval. The number of consecutive trigger signals sent by the ICD 14 to establish an updated trigger interval in the pacemaker 100 may be a predetermined fixed number or may be automatically adjusted based on the variability of the HR.

After sending a required number of consecutive trigger signals at block 918, the time interval between the sent trigger signals is stored in the ICD memory 82 at block 920. The time interval may be a single trigger interval or an average of two or more trigger intervals. The time interval stored by the ICD 14 matches the updated trigger interval stored by the pacemaker 100 after detecting the consecutive trigger signals sent to the pacemaker 100 at blocks 914 and 918. The stored trigger interval in the ICD 14 and the stored trigger interval in the pacemaker 100 will match each other and the patient's current HR within an acceptable error. In some examples, the ICD 14 may use the stored trigger interval to determine the interval change metric and/or if the interval change metric exceeds a change threshold that would result in unacceptable timing of a non-triggered pacing pulse.

The ICD 14 returns to sensing P-waves at block 902 and monitoring the ICM for determining when a trigger signal is again needed to correct the timing of an imminent pacing pulse delivered by the pacemaker 100. If the ICM does not exceed the change threshold at decision block 910, the P counter is compared to the maximum number of allowable non-triggered pacing pulses at block 930. If the non-triggered pacing count is within a predetermined limit from the maximum allowable number of non-triggered pacing pulses, for example one less than the maximum allowable non-triggered pacing pulses, the AV interval started at block 904 is allowed to expire. The ICD 14 controls the emitting device 18 to send a trigger signal at block 914.

The trigger signal is sent even though the interval change metric has not reached the change threshold. The trigger signal is sent to prevent the pacemaker 100 from reaching a lockout number of non-triggered pacing pulses. A single trigger signal may be sent to the pacemaker 100 to reset the non-triggered pacing pulse count at block 916 and an analogous counter in the pacemaker 100, without updating the stored trigger interval. The ICD 14 may optionally advance to block 918 to send one or more additional triggers to update the stored trigger interval.

In some examples, a single trigger signal is sent when the ICM threshold has not been reached (block 910) but the number of consecutive non-triggered pacing pulses is reaching a maximum lockout number (block 930). Since the trigger interval stored by the pacemaker 100 may still be valid, the pacemaker 100 may ignore the single trigger signal for updating the stored trigger interval. The single trigger signal is more than one cardiac cycle since the last trigger signal and may be more than one cardiac cycle until the next trigger signal. The single trigger signal, therefore, is not indicative of a valid trigger interval and is not used in updating the stored trigger interval. The single trigger signal may be used to confirm that the stored trigger interval is still valid. As such, when a single trigger signal is used to prevent pacemaker lockout, the single trigger signal may have a different characteristic than trigger signals used to establish a new, updated trigger interval. The amplitude, signal width, signal frequency, pulse number, pulse interval or other aspect of the single trigger signal may be set differently than trigger signals used to update the stored trigger interval when the ICM threshold has been reached.

For example, when a series of trigger signals are being sent to update the trigger interval in response to the ICM threshold being reached, the first trigger signal sent at block 914 may be sent with a relatively longer signal width than the subsequent trigger signals sent at block 918 and longer than a single trigger signal that is sent to prevent lockout. Alternatively, the single trigger signal sent to prevent lockout may have a relatively longer signal width than the trigger signals sent for updating the trigger interval. The pacemaker 100 is configured to detect the different trigger signals to respond appropriately by either updating a stored trigger interval or leaving the stored trigger interval the same.

If the non-triggered pacing pulse count P has not reached the maximum lockout number (or is not within a predetermined range of the maximum lockout number) as determined at decision block 930, the AV interval timer is stopped at block 932 and no trigger signal is sent. The non-triggered pacing pulse count (P count) is increased by one at block 934. The ICD 14 returns to block 902 to sense the next P-wave.

Now referring to the pacemaker functions shown in dotted block 903, the pacemaker 100 charges the pacing capacitor(s) at block 952 after delivering a preceding pacing pulse, while waiting for the next trigger signal. If a trigger signal is detected at block 954, an optional delay timer is started at block 956. Pacing capacitor charging may continue during the delay time as needed.

A counter in the pacemaker control module 206 counts the number of non-triggered pacing pulses that have been delivered consecutively. At block 958, the non-triggered pace count is reset to zero in response to the detected trigger signal at block 954 since the next pacing pulse will be a triggered pacing pulse. The non-triggered pace count is used to lockout pacing as a safety feature if a maximum number of non-triggered pacing pulses have been reached as described above.

Another counter in the pacemaker control module 206 may count the number of consecutive triggered pacing pulses. The triggered pace count is increased by one at block 960. The triggered pace count may be used to determine when the trigger interval should be updated using the current trigger signal and one or more previous trigger signals.

Upon expiration of the delay timer, a pacing pulse is delivered at block 962. The pacing pulse may be delivered using a fixed PA and a PW stored in pacemaker memory 210 or determined from the trigger signal using any of the methods described above, e.g., in conjunction with FIGS. 11 through 15. If the triggered pace count is greater than one, as determined at block 964, the stored trigger interval is updated at block 966. For example, if at least two consecutive trigger signals have been received, without an intervening non-triggered pacing pulse, the time interval between the two detected trigger signals is determined by a timer in the pacemaker control module 206. The determined trigger interval is stored as an updated trigger interval at block 966. As described above, two or more consecutive trigger signals may be delivered for use by the pacemaker 100 for updating the trigger interval. When the required number of consecutive trigger signals have been detected, the pacemaker 100 uses the intervals measured between the trigger signals to determine an updated trigger interval at block 966.

As indicated above, the trigger signals that are to be used by the pacemaker 100 for updating the stored trigger interval may be designated by a different signal feature recognizable by the pacemaker 100, based on an analysis of the trigger signal by TS analysis module 220. At block 968, a timer in pacemaker control module 206 is set to the updated trigger interval and started. The process returns to block 952 to recharge the pacing capacitor during the trigger interval.

During the trigger interval, the pacemaker 100 waits for the next trigger signal at block 954. If the trigger interval expires before detecting a trigger signal, as indicated at block 980, the triggered pace count is reset to zero at block 986. The non-triggered pace count is increased by one at block 988. The non-triggered pacing pulse is delivered at block 962. Since the triggered pace count has been reset to zero (block 986), the stored trigger interval will not be updated (negative decision at block 964). The non-triggered pace count is compared to a lockout number, N, at block 990. If the lockout number N has not been reached, the control module 206 starts a timer set to the previously stored trigger interval at block 968. Up to N non-triggered pacing pulses may be delivered at the stored trigger interval if no new trigger signal is detected.

If the lockout number N is reached, pacing pulse delivery is suspended at block 992. Pacing delivery may be locked until a new trigger signal is detected (by returning to block 954) to confirm the currently stored trigger interval is still valid, or the new trigger signal is used with at least one more trigger signal for updating the stored trigger interval.

It is understood that the sequence of operations shown in flow chart 900 and other flow charts presented herein may be performed in a different order than the order of the blocks as shown. In some cases operations may be performed substantially simultaneously, such as adjusting counters and setting timers. For example, blocks 956, 958 and 960 may be performed simultaneously upon detecting the trigger signal at block 954. The operations shown in the flow charts presented herein may be combined in other combinations than those shown and in some examples some operations may be omitted or added.

Figure 19:
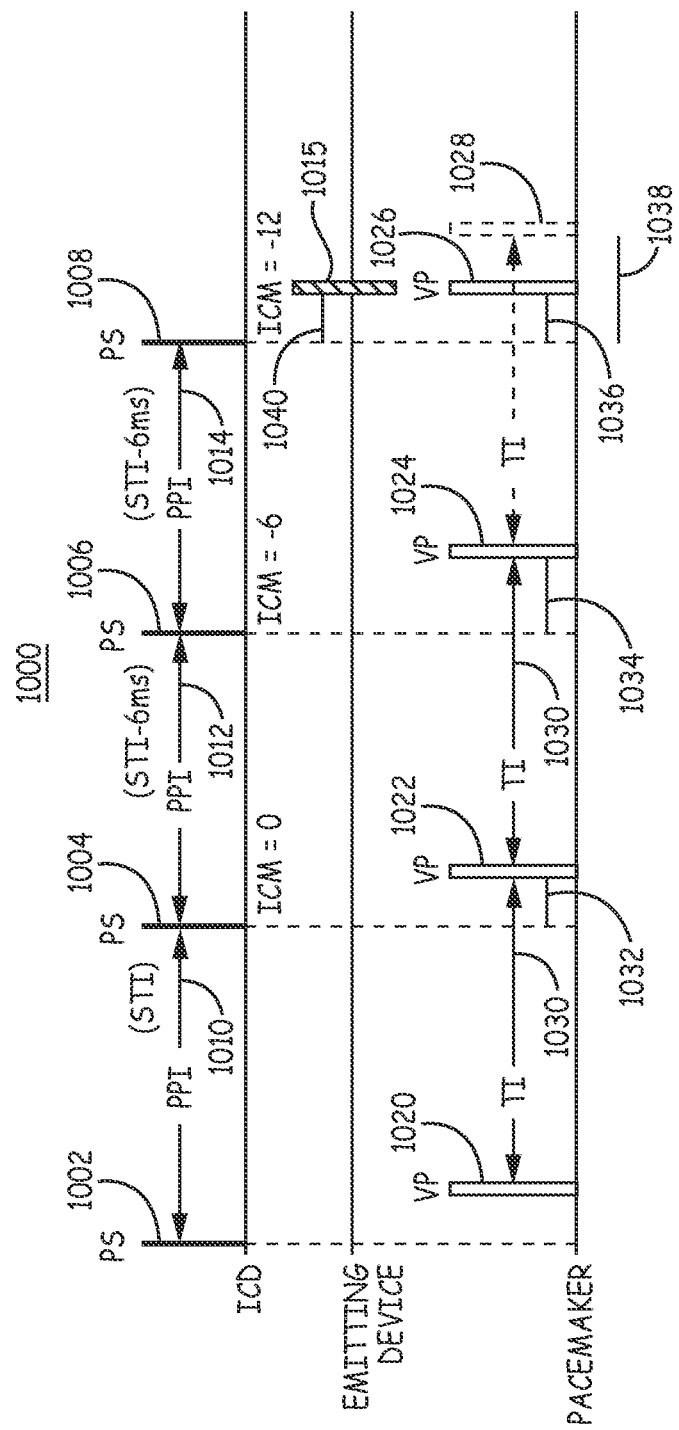
FIG. 19 is a timing diagram depicting one method for determining an interval change metric and controlling pacing pulses delivered by a triggered pacemaker.

FIG. 19 is a timing diagram 1000 depicting one method for determining an interval change metric and controlling pacing pulses delivered by a triggered pacemaker. The ICD 14 (or other sensing device) senses P-waves (PS) 1002, 1004, 1006, and 1008. The sensed P-waves 1002 and 1004 initially arrive at a steady heart rate having a PPI 1010 matching a stored trigger interval (STI). The stored trigger interval 1010 is the trigger interval stored by the ICD 14 and is expected to match the trigger interval (TI) 1030 stored by the pacemaker 100.

In one embodiment, the ICD 14 determines a difference between the STI and each of the PPIs 1010, 1012 and 1014 measured between two consecutively sensed P-waves 1002 through 1008. Consecutive differences between measured PPIs and the STI are summed to accumulate differences between the PPIs and the STI. The interval change metric (ICM) may be determined by the ICD 14 as the summation of the PPI-STI differences determined for each PPI since the last trigger signal.

In the example shown in FIG. 19, the first PPI-STI interval difference is 0 ms. The HR is initially steady. The ICM has a value of 0 ms after sensing P-wave 1004. The ICD 14 does not deliver a trigger signal. The trigger interval (TI) 1030 stored by the pacemaker 100 expires without detecting a trigger signal. An LV pacing pulse (VP) 1022 is delivered by the pacemaker 100 at the TI 1030 following the previous VP 1020. The actual AV interval 1032 between PS 1004 and VP 1022 is equal to a targeted AV interval since the sensed P-wave 1004 occurs at the STI.

The next sensed P-wave 1006 occurs at a PPI 1012 that is X ms shorter, e.g. 6 ms shorter, than the STI. The ICM is set equal to the sum of the previous ICM (0 ms) and the current PPI-STI difference. The ICM, therefore, equals −6 ms after PS 1006. The ICD 14 compares the ICM to a change threshold after each sensed P-wave 1002, 1004, 1006 and 1008. If the ICM is less than the threshold, no trigger signal is sent. In this illustrative example, the change threshold is set at ±10 ms. Since the ICM is −6 ms after PS 1006, no trigger signal is sent.

The next LV pacing pulse 1024 is delivered after the previous VP 1022 at the TI 1030 stored by the pacemaker 100. The VP 1024 delivered at the TI 1030 results in an actual AV interval 1034 that is 6 ms longer than the targeted AV interval due to the P-wave 1006 arriving 6 ms earlier than the STI. This fluctuation of the actual AV interval within ±10 ms of the targeted AV interval is considered acceptable.

The next sensed P-wave 1008 occurs at a PPI 1014 equal to the previous PPI 1012, e.g. 6 ms shorter than the STI. The ICM is updated by summing this difference with the previous ICM. As such, after PS 1008, the ICM is −12 ms (ICM=0 ms−6 ms−6 ms). The ICM now exceeds the change threshold of ±10 ms. The ICD 14 controls the emitting device to emit a trigger signal 1015 at the target AV interval 1040 (less any system delays) following the sensed P-wave 1008. The trigger signal 1015 causes the pacemaker 100 to deliver a pacing pulse 1026 at an actual AV interval 1036 equal to the target AV interval 1040.

Without this correction to the VP 1026 timing made by controlling emitting device 18 to emit trigger signal 1015, a hypothetical VP 1028 that would have been delivered at the expiration of the stored TI 1030 would occur at an unacceptably long AV interval 1038, 12 ms longer than the targeted AV interval 1040. The detected trigger signal 1015 and the next trigger signal (not shown) may be used by the pacemaker 100 to reset the TI 1030.

Figure 20:
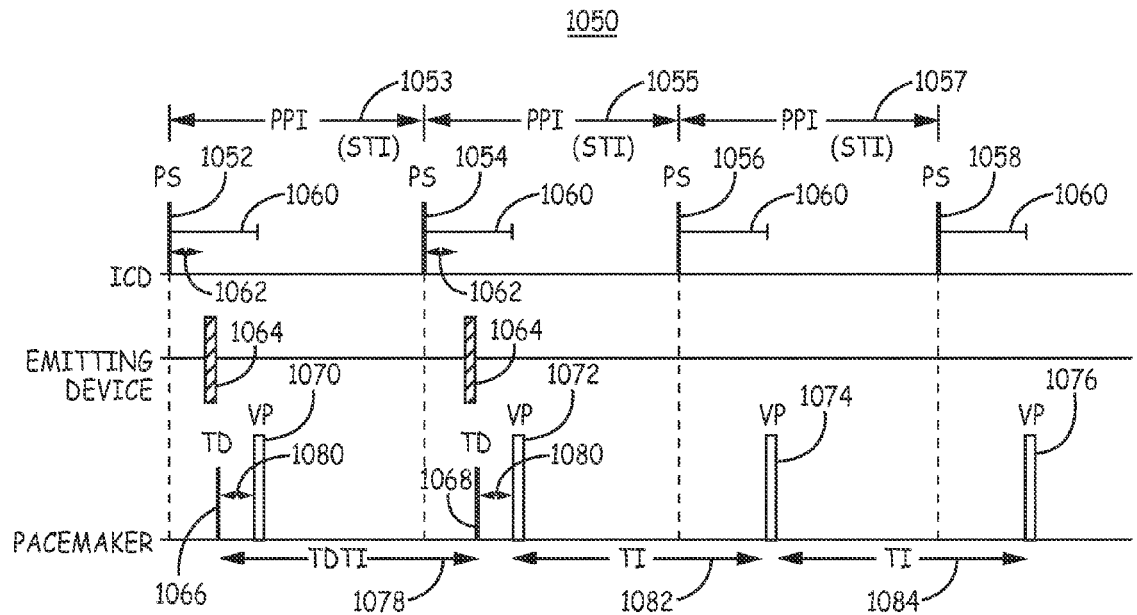
FIG. 20 is a timing diagram illustrating an example method for controlling triggered and non-triggered pacing pulses using a delay time.

FIG. 20 is a timing diagram 1050 illustrating an example method for controlling triggered and non-triggered pacing pulses using a delay time. The ICD 14 senses P-waves 1052, 1054, 1056 and 1058 occurring at respective PPIs 1053, 1055 and 1057 during a steady, stable HR. The ICD 14 controls the emitting device 18 to emit a trigger signal 1064 at a control time interval 1062 after sensing P-wave 1052. The pacemaker 100 detects the trigger signal 1064 and produces a trigger detect (TD) signal 1066. The pacemaker 100 starts a delay time 1080 upon detecting the trigger signal 1064 and delivers the triggered pacing pulse VP 1070 upon expiration of delay time 1080. The control time interval 1062 used by the ICD 14 for controlling the time of the emitted trigger signal 1064 after PS 1052 is equal to the targeted AV interval 1060 minus delay time 1080 (and any system delays).

On the next sensed P-wave 1054, the PPI 1053 is determined. The control time 1062 is started. A trigger signal 1064 is emitted at the expiration of control time 1062. A trigger detect signal 1068 is produced by the pacemaker 100, which starts delay time 1080. The triggered VP 1072 is delivered at the target AV interval 1060 upon expiration of delay time 1080.

The pacemaker 100 determines a trigger detect time interval (TDTI) 1078 between the two consecutive TD signals 1066 and 1068. The pacemaker 100 updates the trigger interval (TI) 1082 stored by the pacemaker 100 using the TDTI 1078. Assuming that the HR has been stable for a required number of PPIs to establish an updated, stored trigger interval, the updated trigger interval (TI) 1082 is started upon the next triggered VP 1072, which is delivered after the delay time 1080.

As described above, the ICD 14 determines a stored trigger interval (STI) as the interval between emitted trigger signals 1064, which is expected to match the updated trigger interval 1082 stored by the pacemaker 100. When the ICD 14 senses the next P-wave 1056, the PPI 1055 is determined and compared to the STI. PPI 1055 equals the STI. The ICD 14 determines that a trigger signal is not needed following PS 1056 since the PPI 1055 equals the STI. If no trigger signal is detected by the pacemaker 100 before expiration of the TI 1082, a VP 1074 is delivered at the expiration of the TI 1082. VP 1074 is properly delivered at the target AV interval 1060 using the TI 1082 without requiring emission and detection of a trigger signal following PS 1056.

A next TI 1084 is started upon the VP 1074. This process repeats on the next PS 1058, which occurs at a PPI 1057 equal to the STI. No trigger signal is delivered. When the TI 1084 expires without detecting a trigger signal, the next VP 1076 is delivered at the target AV interval 1060, and another TI (not shown) is started.

If a trigger signal is detected before the TI 1082 or 1084 expires, the delay time 1080 would be started, and the VP would be delivered at the end of the delay time. A newly detected trigger signal would be used to update the stored TI. However, as long as the HR remains steady, the ventricular pacing pulses can be delivered at the targeted AV interval 1060, or within a predefined acceptable range of the AV interval 1060, without requiring a trigger signal on every heartbeat. As described in conjunction with FIG. 19, the ICD 14 monitors an ICM. If the HR increases so that the ICM exceeds the ICM threshold, the ICD 14 controls the emitting device 18 to deliver a trigger signal to update the trigger interval stored by the pacemaker 100.

Figure 21:
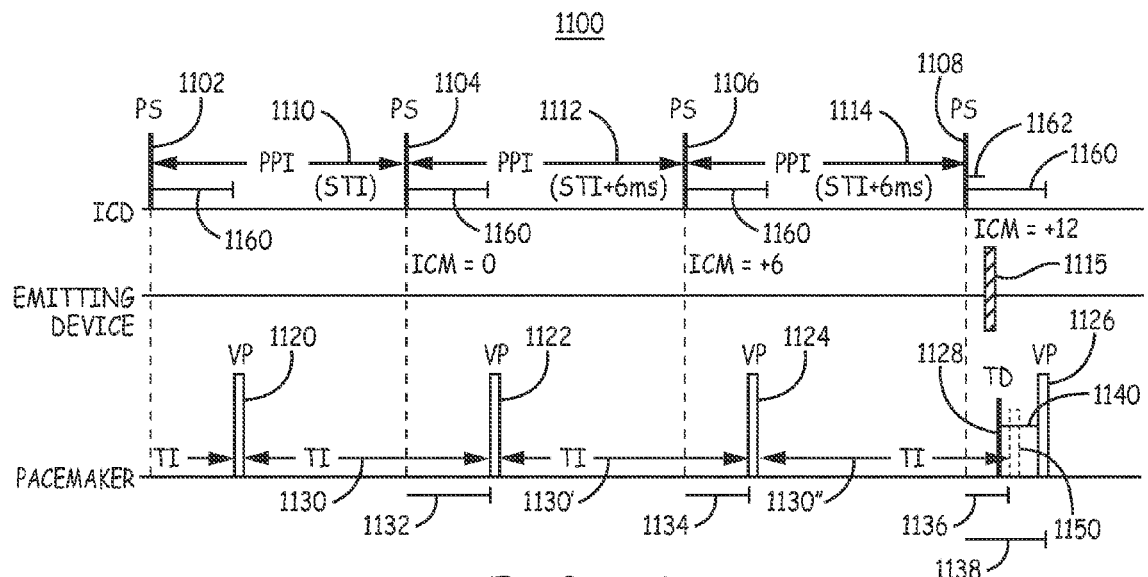
FIG. 21 is a timing diagram depicting an example method for determining an interval change metric and controlling pacing pulses delivered by a triggered pacemaker during a decreasing heart rate.

FIG. 21 is a timing diagram 1100 depicting an example method for determining an ICM and controlling pacing pulses delivered by a triggered pacemaker 100 during a decreasing HR. The time intervals shown in FIG. 21, and other timing diagrams presented herein, are illustrative in nature and are not necessarily drawn to scale. In the example shown in FIG. 19, a trigger signal can be sent to the pacemaker 100 during any cardiac cycle at a shorter interval than a previous trigger interval to cause the pacemaker 100 to deliver a pacing pulse earlier when the HR increases (PPIs shorten). When the HR slows down, however, a trigger signal may need to be delivered later than the expiration of a trigger interval that was previously updated during a relatively faster HR. By sending a trigger signal before the end of a targeted AV interval, and including a delay time 1080 as shown in FIG. 20, a trigger signal can be sent to the pacemaker 100 before the expiration of a trigger interval and a scheduled non-triggered pacing pulse to cause control module to start a delay timer to slow down the rate of the pacing pulses. An illustrative example of this situation is shown in FIG. 21.

In FIG. 21, the ICD 14 (or other sensing device) senses P-waves (PS) 1102, 1104, 1106, and 1108. The sensed P-waves 1102 and 1104 initially arrive at a steady heart rate having a PPI 1110 matching a stored trigger interval (STI). The stored trigger interval is the trigger time interval stored by the ICD 14 that is expected to match the TI 1130 stored by the pacemaker 100 as described above.

The ICD 14 determines the ICM as the summation of the consecutive PPI-STI differences when no trigger signal is delivered. The ICM represents an accumulation of cardiac cycle length differences since a most recent trigger signal was delivered to update a trigger interval stored by the pacemaker 100. In the example shown in FIG. 21, the first PPI-STI interval difference is 0 ms due to a steady HR. The ICM has a value of 0 ms after sensing P-wave 1104. The ICD 14 does not deliver a trigger signal. An LV pacing pulse (VP) 1122 is delivered by the pacemaker 100 at the expiration of the TI 1130 started upon the previous VP 1120. The actual AV interval 1132 between PS 1104 and VP 1122 matches a targeted AV interval 1160 since PS 1104 occurs at the STI. Non-triggered VP 1120 and non-triggered VP 1122 each occur at the target AV interval 1160 without requiring a trigger signal after PS 1102 and PS 1104 as long as the HR remains steady.

The next sensed P-wave 1106 occurs at a PPI 1112 that is 6 ms longer than the STI. The ICM is set equal to the sum of the previous ICM (0 ms) and the current PPI-STI difference (+6 ms). The ICM equals +6 ms after PS 1106. The ICD 14 compares the ICM to the change threshold of ±10 ms in this example. Since the ICM is less than the change threshold, no trigger signal is sent.

The TI 1130' started at the expiration of the previous VP 1122 expires and the next VP 1124 is delivered. VP 1124 is a non-triggered pacing pulse delivered at an actual AV interval 1134 based on the TI 1130 stored by the pacemaker 100. The actual AV interval 1134 is 6 ms shorter than the targeted AV interval due to the P-wave 1106 arriving 6 ms later than the STI. This fluctuation of the actual AV interval within ±10 ms of the targeted AV interval 1160 is within acceptable limits.

The next sensed P-wave 1108 occurs at a PPI 1114 equal to the previous PPI 1112, i.e. 6 ms longer than the STI. The ICM is updated by summing this difference with the previous ICM. As such, after PS 1108, the ICM is +12 ms (ICM=0 ms+6 ms+6 ms). The ICM now exceeds the change threshold of ±10 ms. The ICD 14 controls the emitting device 18 to emit a trigger signal 1115 at a control time interval 1162 following the sensed P-wave 1108. Control time interval 1162 is equal to the target AV delay 1160 minus a delay time 1140 applied by the pacemaker 100 after detecting a trigger signal (less any system delays).

The trigger signal 1115 is detected by the pacemaker 100 during TI 1130". The pacemaker 100 produces a TD signal 1128 in response to the trigger signal 1115, before a scheduled non-triggered pacing pulse 1150. The non-triggered pacing pulse 1150 is withheld. The TD signal 1128 starts delay time 1140. A scheduled non-triggered pacing pulse 1150 at the expiration of the TI 1130" would arrive at a hypothetical AV interval 1136, which is unacceptably shorter than the target AV interval 1160. By delivering trigger signal 1115 during the TI 1130" and starting a delay time 1140 in response to the trigger signal, the VP 1126 is delivered later than expiration of the TI 1130". The actual AV interval 1138 is equal to the target AV interval 1160. The control time 1162 and the delay time 1140 (plus any system delays accounted for in setting control time 1162 and delay time 1140') result in the triggered VP 1126 at the target AV interval 1160. Additional trigger signals may be delivered on subsequently sensed P-waves to reset the TI stored by the pacemaker 100.

Thus, various examples of a medical device system and associated method for controlling a triggered therapy delivery device have been described according to illustrative embodiments. However, one of ordinary skill in the art will appreciate that various modifications may be made to the described embodiments without departing from the scope of the following claims.

The invention claimed is:

1. A method for controlling automated delivery of therapeutic stimulation pulses by a medical device system, the method comprising:

sensing a plurality of physiological events by a first device;

controlling a transducer by the first device to emit a plurality of trigger signals in response to the sensed plurality of physiological events, the plurality of trigger signals having a first combined total time duration over the plurality of physiological events;

detecting the plurality of trigger signals by a second device;

delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration;

setting a stimulation pulse control parameter by the first device;

controlling the transducer by the first device to emit at least one of the plurality of trigger signals to contain stimulation pulse control parameter information;

determining by the second device a stimulation pulse control parameter from the detected plurality of trigger signals including the at least one of the plurality of trigger signals containing the stimulation pulse control parameter information; and delivering at least one of the plurality of stimulation pulses according to the stimulation pulse control parameter; and further comprising:

performing a capture threshold search to determine the stimulation pulse control parameter by:

controlling the transducer to emit a series of trigger signals to control the second device to deliver a plurality of stimulation pulses at different pulse energies;

sensing by the first device a physiological signal to detect capture by the plurality of stimulation pulses; and determining by the first device the lowest pulse energy that captures a target tissue in response to the physiological signal.

2. A method for controlling automated delivery of therapeutic stimulation pulses by a medical device system, the method comprising:

sensing a plurality of physiological events by a first device;

controlling a transducer by the first device to emit a plurality of trigger signals in response to the sensed plurality of physiological events, the plurality of trigger signals having a first combined total time duration over the plurality of physiological events;

detecting the plurality of trigger signals by a second device;

delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration; and further comprising:

determining intervals between the plurality of sensed physiological events;

determining a metric of differences between the intervals;
comparing the metric to a change threshold; and
withholding a trigger signal in response to the metric not meeting the change threshold.

3. A method for controlling automated delivery of therapeutic stimulation pulses by a medical device system, the method comprising:
sensing a plurality of physiological events by a first device;
controlling a transducer by the first device to emit a plurality of trigger signals in response to the sensed plurality of physiological events, the plurality of trigger signals having a first combined total time duration over the plurality of physiological events;
detecting the plurality of trigger signals by a second device;
delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration; and
further comprising:
determining by the second device an interval between successive ones of the plurality of trigger signals;
storing the determined interval as a trigger interval;
starting a delay time by the second device in response to detecting one of the plurality of trigger signals;
delivering a first one of the plurality of therapeutic stimulation pulses after the delay time expires;
scheduling a next one of the plurality of therapeutic stimulation pulses by starting the trigger interval upon delivering the first one of the plurality of therapeutic stimulation pulses;
adjusting the next one of the plurality of therapeutic stimulation pulses in response to detecting a next one of the plurality of trigger signals during the trigger interval; and
delivering the next one of the plurality of therapeutic stimulation pulses without adjustment upon expiration of the trigger interval if the next one of the plurality of trigger signals is not detected during the trigger interval.

4. A method for controlling automated delivery of therapeutic stimulation pulses by a medical device system, the method comprising:
sensing a plurality of physiological events by a first device;
controlling a transducer by the first device to emit a plurality of trigger signals in response to the sensed plurality of physiological events, the plurality of trigger signals having a first combined total time duration over the plurality of physiological events;
detecting the plurality of trigger signals by a second device;
delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration; and
further comprising:
controlling the transducer by the first device to emit the next one of the plurality of trigger signals at a control time interval after a sensed physiological event, the control time interval being set at a targeted therapy time interval less a delay time by the second device in response to detecting one of the plurality of trigger signals.

5. A method for controlling automated delivery of therapeutic stimulation pulses by a medical device system, the method comprising:
sensing a plurality of physiological events by a first device;
controlling a transducer by the first device to emit a plurality of trigger signals in response to the sensed plurality of physiological events, the plurality of trigger signals having a first combined total time duration over the plurality of physiological events;
detecting the plurality of trigger signals by a second device;
delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration; and
further comprising:
monitoring a remaining voltage of a battery of the second device by a control module of the second device;
in response to the remaining battery voltage reaching a threshold, adjusting an amplitude of the therapeutic stimulation pulses;
sensing a physiological signal by the first device;
determining by the first device that the amplitude of the therapeutic stimulation pulses has been adjusted in response to the physiological signal; and
generating an alert signal by the first device in response to determining that the amplitude has been adjusted.

6. A method for controlling automated delivery of therapeutic stimulation pulses by a medical device system, the method comprising:
sensing a plurality of physiological events by a first device;
controlling a transducer by the first device to emit a plurality of trigger signals in response to the sensed plurality of physiological events, the plurality of trigger signals having a first combined total time duration over the plurality of physiological events;
detecting the plurality of trigger signals by a second device;
delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration; and
further comprising:
controlling the transducer to emit each of the plurality of trigger signals comprising a plurality of pulses separated by respective pulse intervals;
setting a noise rejection interval during the pulse intervals; and
rejecting a detected trigger signal pulse if a pulse is detected during the noise rejection interval.

7. A method for controlling automated delivery of therapeutic stimulation pulses by a medical device system, the method comprising:
sensing a plurality of physiological events by a first device;
controlling a transducer by the first device to emit a plurality of trigger signals in response to the sensed plurality of physiological events, the plurality of trigger signals having a first combined total time duration over the plurality of physiological events;

detecting the plurality of trigger signals by a second device;

delivering a plurality of therapeutic stimulation pulses by the second device in response to detecting the plurality of trigger signals, the plurality of therapeutic stimulation pulses having a second combined total time duration over the plurality of physiological events that is greater than the first combined total time duration; and further comprising:

controlling the transducer to emit first ones of the plurality of trigger signals with a first trigger signal parameter and second ones of the plurality of trigger signals with a second trigger signal parameter different than the first trigger signal parameter;

detecting the first ones of the plurality of trigger signals by the second device, the second device configured to detect the first trigger signal parameter; and detecting the second ones of the plurality of trigger signals by a third device configured to detect the second trigger signal parameter and deliver therapeutic stimulation pulses in response to detecting the second ones of the plurality of trigger signals.

8. A medical device system for controlling automated delivery of therapeutic stimulation pulses, comprising:

a transducer for emitting a trigger signal;

a first device configured to:
sense a plurality of physiological events; and
control the transducer to produce a plurality of trigger signals in response to the sensed plurality of physiological events, the plurality of trigger signals having a first combined total time duration over the plurality of physiological events;

a second device configured to:
detect the plurality of trigger signals; and
deliver a plurality of therapeutic stimulation pulses in response to detecting the plurality of trigger signals, the plurality of therapeutic stimulation pulses having a second combined total time duration over the plurality of physiological events that is greater than the first combined total time duration;

wherein the first device is further configured to:
set a stimulation pulse control parameter; and
control the transducer to emit at least one of the plurality of trigger signals to contain stimulation pulse control parameter information; and the second device is further configured to:
determine a stimulation pulse control parameter from the detected plurality of trigger signals including the at least one of the plurality of trigger signals containing the stimulation pulse control parameter information; and
deliver at least one of the plurality of stimulation pulses according to the stimulation pulse control parameter; and wherein:

the first device and the second device are configured to perform a capture threshold search to determine the stimulation pulse control parameter by:

controlling the transducer by the first device to emit a series of trigger signals to control the second device to deliver a plurality of stimulation pulses at different pulse energies;

sensing by the first device a physiological signal to detect capture by the plurality of stimulation pulses; and determining by the first device the lowest pulse energy that captures a target tissue in response to the physiological signal.

9. A medical device system for controlling automated delivery of therapeutic stimulation pulses, comprising:

a transducer for emitting a trigger signal;

a first device configured to:
sense a plurality of physiological events; and
control the transducer to produce a plurality of trigger signals in response to the sensed plurality of physiological events, the plurality of trigger signals having a first combined total time duration over the plurality of physiological events;

a second device configured to:
detect the plurality of trigger signals; and
deliver a plurality of therapeutic stimulation pulses in response to detecting the plurality of trigger signals, the plurality of therapeutic stimulation pulses having a second combined total time duration over the plurality of physiological events that is greater than the first combined total time duration; and wherein:

the first device is further configured to:
determine intervals between the plurality of sensed physiological events;
determine a metric of differences between the intervals;
compare the metric to a change threshold; and
control the transducer to withhold a trigger signal in response to the metric not meeting the change threshold.

10. A medical device system for controlling automated delivery of therapeutic stimulation pulses, comprising:

a transducer for emitting a trigger signal;

a first device configured to:
sense a plurality of physiological events; and
control the transducer to produce a plurality of trigger signals in response to the sensed plurality of physiological events, the plurality of trigger signals having a first combined total time duration over the plurality of physiological events;

a second device configured to:
detect the plurality of trigger signals; and
deliver a plurality of therapeutic stimulation pulses in response to detecting the plurality of trigger signals, the plurality of therapeutic stimulation pulses having a second combined total time duration over the plurality of physiological events that is greater than the first combined total time duration; and wherein the second device is further configured to:
determine an interval between successive ones of the plurality of trigger signals;
store the determined interval as a trigger interval;
start a delay time in response to detecting one of the plurality of trigger signals;
deliver a first one of the plurality of therapeutic stimulation pulses after the delay time expires;
schedule a next one of the plurality of therapeutic stimulation pulses by starting the trigger interval upon delivering the first one of the plurality of therapeutic stimulation pulses;
adjust the next one of the plurality of therapeutic stimulation pulses in response to detecting a next one of the plurality of trigger signals during the trigger interval; and deliver the next one of the plurality of therapeutic stimulation pulses without adjustment upon expiration of the trigger interval if the next one of the plurality of trigger signals is not detected during the trigger interval.

11. The system of claim 10, wherein the first device is further configured to control the transducer to emit the next one of the plurality of trigger signals at a control time interval after a sensed physiological event, the control time interval being set at a targeted therapy time interval less the delay time.

12. A medical device system for controlling automated delivery of therapeutic stimulation pulses, comprising:
a transducer for emitting a trigger signal;
a first device configured to:
sense a plurality of physiological events; and
control the transducer to produce a plurality of trigger signals in response to the sensed plurality of physiological events, the plurality of trigger signals having a first combined total time duration over the plurality of physiological events;
a second device configured to:
detect the plurality of trigger signals; and
deliver a plurality of therapeutic stimulation pulses in response to detecting the plurality of trigger signals, the plurality of therapeutic stimulation pulses having a second combined total time duration over the plurality of physiological events that is greater than the first combined total time duration; wherein:
the second device comprises a control module and a battery coupled to the control module, the control module configured to:
monitor a remaining voltage of the battery;
adjust an amplitude of at least a portion of the therapeutic stimulation pulses in response to the remaining battery voltage reaching a threshold;
the first device configured to:
sense a physiological signal;
determine that the amplitude of the plurality of the therapeutic stimulation pulses has been adjusted in response to the physiological signal; and
generate an alert signal in response to determining that the amplitude has been adjusted.

13. A medical device system for controlling automated delivery of therapeutic stimulation pulses, comprising:
a transducer for emitting a trigger signal;
a first device configured to:
sense a plurality of physiological events; and
control the transducer to produce a plurality of trigger signals in response to the sensed plurality of physiological events, the plurality of trigger signals having a first combined total time duration over the plurality of physiological events;
a second device configured to:
detect the plurality of trigger signals; and
deliver a plurality of therapeutic stimulation pulses in response to detecting the plurality of trigger signals, the plurality of therapeutic stimulation pulses having a second combined total time duration over the plurality of physiological events that is greater than the first combined total time duration; wherein:
the first device is configured to:
control the transducer to emit each of the plurality of trigger signals comprising a plurality of pulses separated by respective pulse intervals;
the second device is configured to:
set a noise rejection interval during each of the pulse intervals; and
reject a detected trigger signal pulse if the detected trigger signal pulse is detected during the noise rejection interval.

14. A medical device system for controlling automated delivery of therapeutic stimulation pulses, comprising:
a transducer for emitting a trigger signal;
a first device configured to:
sense a plurality of physiological events; and
control the transducer to produce a plurality of trigger signals in response to the sensed plurality of physiological events, the plurality of trigger signals having a first combined total time duration over the plurality of physiological events;
a second device configured to:
detect the plurality of trigger signals; and
deliver a plurality of therapeutic stimulation pulses in response to detecting the plurality of trigger signals, the plurality of therapeutic stimulation pulses having a second combined total time duration over the plurality of physiological events that is greater than the first combined total time duration; and
further comprising a third device, wherein:
the first device is configured to:
control the transducer to emit first ones of the plurality of trigger signals with a first trigger signal parameter and second ones of the plurality of trigger signals with a second trigger signal parameter different than the first trigger signal parameter;
the second device is configured to detect the first ones of the plurality of trigger signals by detecting trigger signals of the plurality of trigger signals having the first trigger signal parameter: and
the third device is configured to:
detect the second ones of the plurality of trigger signals by detecting trigger signals of the plurality of trigger signals having the second trigger signal parameter; and
deliver therapeutic stimulation pulses in response to detecting the second ones of the plurality of trigger signals.

* * * * *